(12) United States Patent
Shiotsuka et al.

(10) Patent No.: US 7,833,731 B2
(45) Date of Patent: Nov. 16, 2010

(54) GOLD-BINDING PROTEIN AND USE THEREOF

(75) Inventors: Hidenori Shiotsuka, Kawasaki (JP);
Takeshi Imamura, Chigasaki (JP);
Izumi Kumagai, Sendai (JP)

(73) Assignee: Canon Kabushiki Kaisha, Tokyo (JP)

( * ) Notice: Subject to any disclaimer, the term of this patent is extended or adjusted under 35 U.S.C. 154(b) by 773 days.

(21) Appl. No.: 10/592,791

(22) PCT Filed: Mar. 31, 2005

(86) PCT No.: PCT/JP2005/006815
§ 371 (c)(1),
(2), (4) Date: Sep. 14, 2006

(87) PCT Pub. No.: WO2005/095461
PCT Pub. Date: Oct. 13, 2005

(65) Prior Publication Data
US 2007/0178522 A1    Aug. 2, 2007

(30) Foreign Application Priority Data
Mar. 31, 2004  (JP)  .............................. 2004-108388

(51) Int. Cl.
*G01N 33/53* (2006.01)
*A61K 39/395* (2006.01)

(52) U.S. Cl. .................. 435/7.21; 435/7.1; 436/501; 436/512; 436/518; 436/543; 436/547; 424/130.1

(58) Field of Classification Search ...................... None
See application file for complete search history.

(56) References Cited

U.S. PATENT DOCUMENTS

| | | | |
|---|---|---|---|
| 4,732,864 A | 3/1988 | Tolman | 436/547 |
| 4,769,223 A | 9/1988 | Volesky et al. | 423/27 |
| 5,503,987 A | 4/1996 | Wagner et al. | 435/7.94 |
| 5,639,624 A | 6/1997 | Wagner et al. | |
| 5,665,597 A | 9/1997 | Imamura et al. | 435/253.3 |
| 5,670,645 A | 9/1997 | Johnson | |
| 5,679,568 A | 10/1997 | Imamura et al. | 435/262.5 |
| 5,693,527 A | 12/1997 | Imamura | 435/262 |
| 5,803,664 A | 9/1998 | Kawabata et al. | 405/128 |
| 5,807,736 A | 9/1998 | Kozaki et al. | 435/262.5 |
| 5,837,242 A | 11/1998 | Holliger et al. | 424/136.1 |
| 5,854,059 A | 12/1998 | Kozaki et al. | 435/262 |
| 5,863,789 A | 1/1999 | Komatsu et al. | 435/262 |
| 5,945,331 A | 8/1999 | Kozaki et al. | 435/262 |
| 5,962,305 A | 10/1999 | Mihara et al. | 435/262.5 |
| 5,993,658 A | 11/1999 | Kato et al. | 210/611 |
| 6,004,772 A | 12/1999 | Imamura et al. | 435/34 |
| 6,017,746 A | 1/2000 | Imamura et al. | 435/252.1 |
| 6,096,530 A | 8/2000 | Kato et al. | 435/253.3 |
| 6,319,706 B1 | 11/2001 | Kawaguchi et al. | 435/293.1 |
| 6,472,191 B1 | 10/2002 | Yano et al. | 435/189 |
| 6,479,621 B2 | 11/2002 | Honma et al. | 528/361 |
| 6,586,562 B2 | 7/2003 | Honma et al. | 528/361 |
| 6,649,381 B1 | 11/2003 | Honma et al. | 435/135 |
| 6,660,516 B1 | 12/2003 | Imamura et al. | 435/252.8 |
| 6,686,439 B2 | 2/2004 | Kenmoku et al. | 528/272 |
| 6,803,444 B2 | 10/2004 | Suzuki et al. | 528/361 |
| 6,808,854 B2 | 10/2004 | Imamura et al. | 430/110 |
| 6,828,074 B2 | 12/2004 | Yano et al. | 430/109.1 |
| 6,855,472 B2 | 2/2005 | Imamura et al. | 430/109.4 |
| 6,858,367 B2 | 2/2005 | Yano et al. | 430/109 |
| 6,858,417 B2 | 2/2005 | Yano et al. | 435/189 |
| 6,861,496 B2 | 3/2005 | Kenmoku et al. | 528/272 |
| 6,861,550 B2 | 3/2005 | Honma et al. | 560/53 |
| 6,864,074 B2 | 3/2005 | Yano et al. | 435/189 |
| 6,867,023 B2 | 3/2005 | Honma et al. | 435/135 |
| 6,869,782 B2 | 3/2005 | Kenmoku et al. | 435/130 |
| 6,908,720 B2 | 6/2005 | Kenmoku et al. | 430/97 |
| 7,169,598 B2 | 1/2007 | Honma et al. | 435/253.3 |
| 7,220,840 B2 * | 5/2007 | Ruben et al. | 530/388.23 |
| 2003/0049800 A1 | 3/2003 | Saravis et al. | 435/70.21 |
| 2006/0063715 A1 | 3/2006 | Whitlow et al. | 514/12 |
| 2006/0115861 A1 | 6/2006 | Shiotsuka et al. | 435/7.9 |
| 2006/0183235 A1 | 8/2006 | Hashimoto et al. | 436/86 |
| 2006/0275811 A1 | 12/2006 | Hatakeyama et al. | 435/6 |
| 2007/0054315 A1 | 3/2007 | Imamura et al. | 435/7.1 |

FOREIGN PATENT DOCUMENTS

| | | |
|---|---|---|
| EP | 0 235 457 | 9/1987 |
| JP | 60-166625 | 8/1985 |
| JP | 5-55534 | 3/1993 |
| JP | 7-501451 | 2/1995 |
| JP | 8-504100 | 5/1996 |
| WO | 95/00845 | 1/1995 |
| WO | 99/27356 A1 | 6/1999 |
| WO | 99/45110 | 9/1999 |
| WO | 02/02641 | 1/2002 |
| WO | 03/029431 | 4/2003 |
| WO | 03/055979 | 7/2003 |
| WO | WO 03/055979 * | 7/2003 |

(Continued)

OTHER PUBLICATIONS

Stanley Brown (Nature Biotechnology, vol. 15, Mar. 1997, pp. 269-272).*

Carlos R. Barbas III, et al., "Molecular Profile of an Antibody Response to HIV-1 as Probed by Combinatorial Libraries", Journal of Molecular Biology, vol. 230, 1993, pp. 812-823.

(Continued)

*Primary Examiner*—Lisa V Cook
(74) *Attorney, Agent, or Firm*—Fitzpatrick, Cella, Harper & Scinto

(57) ABSTRACT

A protein utilizing an anti-gold antibody and a gold-binding side which is a part of the anti-gold antibody is constructed. This protein is capable of specifically binding to gold. This protein or a complex protein containing such a protein can be used for the detection of a target substance.

5 Claims, 16 Drawing Sheets

OTHER PUBLICATIONS

Stanley Brown, "Metal-recognition by repeating polypeptides", Nature Biotechnology, vol. 15, Mar. 1997, pp. 269-272.
Seung-Wuk Lee, et al., "Ordering of Quantum Dots Using Genetically Engineered Viruses", Science, vol. 296, May 3, 2002, pp. 892-895.
Marc Better, et al., *Escherichia coli* Secretion of an Active Chimeric Antibody Fragment, Science, vol. 240, No. 4855, May 20, 1988, pp. 1041-1043.
Pedro Cuatrecasas, et al., "Adsorbents for Affinity Chromatography. Use Of *N*-Hydroxysuccinimide Esters of Agarose", Biochemistry, vol. 11, No. 12, 1972, pp. 2291-2299.
G. Galfre, et al., "Antibodies to major histocompatibility antigens produced by hybrid cell lines", Nature, vol. 266, Apr. 7, 1977, pp. 550-552.
Akiko Koide, et al., "The Fibronectin Type III Domain as a Scaffold for Novel Binding Proteins", J. Mol. Biol., vol. 284, 1998, pp. 1141-1151.
Brian Kuhlman, et al., "Design of a Novel Globular Protein Fold with Atomic-Level Accuracy", Science, vol. 302, Nov. 21, 2003, pp. 1364-1368. (with pp. S1-S15).
Wlad Kusnezow, et al., "Antibody microarrays: An evaluation of production parameters", Proteomics, vol. 3, 2003, pp. 254-264.
Katsumi Maenaka, et al., "A Stable Phage-Display System Using a Phagemid Vector: Phage Display of Hen Egg-White Lysozyme (HEL), *Escherichia coli* Alkaline, Phosphatase, and Anti-HEL Monoclonal Antibody, HyHEL10", Biochemical and Biophysical Research Communications, vol. 218, No. 0122, 1996, pp. 682-687.
Ganesh K. Ramachandran, et al., "A Bond-Fluctuation Mechanism for Stochastic Switching in Wired Molecules", Science, vol. 300, May 20, 2003, pp. 1413-1416. (with pp. S1-S5).
Arne Skerra, "'Anticalins': a new class of engineered ligand-binding proteins with antibody-like properties", Reviews in Molecular Biotechnology, vol. 74, 2001, pp. 257-275.
Arne Skerra, et al., "Assembly of a Functional Immunoglobulin Fv Fragment in *Escherichia coli*", Science, vol. 240, No. 4855, May 20, 1988, pp. 1038-1041.
Silvia Spinelli, et al., "Lateral Recognition of a Dye Hapten by a Llama VHH Domain", J. Mol. Biol., vol. 311, 2001, pp. 123-129.
Mitsuo Umetsu, et al., "How Additives Influence the Refolding of Immunoglobulin-folded Proteins in a Stepwise Dialysis System", The Journal of Biological Chemistry, vol. 278, No. 11, Mar. 14, 2003, pp. 8979-8987.
Sandra R. Whaley, et al., "Selection of peptides with semiconductor binding specificity for directed nanocrystal assembly", Nature, vol. 405, Jun. 8, 2000, pp. 665-668.
Babacan, et al., "Evaluation of antibody immobilization methods for piezoelectric biosensor application", Biosensors & Bioelectronics, vol. 15, 2000, pp. 615-621.
Official Action dated Apr. 3, 2009 in Chinese Application No. 2005800105197.
Official Action dated Aug. 6, 2009 in European Official Action 05 728 901.9.
Search Report dated Jun. 10, 2009 in European Application No. 05728901.9.

* cited by examiner

SEQUENCE LISTING

```
<160> NUMBER OF SEQ ID NOS: 152

<210> SEQ ID NO 1
<211> LENGTH: 5
<212> TYPE: PRT
<213> ORGANISM: human

<400> SEQUENCE: 1

Asp Tyr Tyr Met Asp
1               5

<210> SEQ ID NO 2
<211> LENGTH: 17
<212> TYPE: PRT
```

```
<213> ORGANISM: human

<400> SEQUENCE: 2

Ser Ile Lys Gln Asp Gly Ser Glu Thr Arg Tyr Gly Asp Ser Val Arg Gly
1               5                   10                  15

<210> SEQ ID NO 3
<211> LENGTH: 9
<212> TYPE: PRT
<213> ORGANISM: human

<400> SEQUENCE: 3

Glu Leu Asp Gly Gly Phe Phe Asp Phe
1               5

<210> SEQ ID NO 4
<211> LENGTH: 5
<212> TYPE: PRT
<213> ORGANISM: human

<400> SEQUENCE: 4

Gly His Trp Met His
1

<210> SEQ ID NO 5
<211> LENGTH: 17
<212> TYPE: PRT
<213> ORGANISM: human

<400> SEQUENCE: 5

Arg Ile Asp Glu His Gly Ser Ser Ala Tyr Tyr Ala Asp Ser Val Asn Gly
1               5                   10                  15

<210> SEQ ID NO 6
<211> LENGTH: 15
<212> TYPE: PRT
<213> ORGANISM: human

<400> SEQUENCE: 6

Leu Gly Phe Ile Thr Pro Glu Val Val His Trp Ser Ser Asp Ile
1               5                   10                  15

<210> SEQ ID NO 7
<211> LENGTH: 5
<212> TYPE: PRT
<213> ORGANISM: human

<400> SEQUENCE: 7

Arg Phe Tyr Trp Asn
1               5

<210> SEQ ID NO 8
<211> LENGTH: 16
<212> TYPE: PRT
<213> ORGANISM: human

<400> SEQUENCE: 8

Arg Ile Phe Thr Asn Gly Thr Thr Asn Tyr Asn Pro Ser Leu Gly Ser
1               5                   10                  15

<210> SEQ ID NO 9
<211> LENGTH: 13
<212> TYPE: PRT
<213> ORGANISM: human
```

```
<400> SEQUENCE: 9

Gly Gly Asp Tyr Gly Pro Ala Leu Ala Trp Phe Asp Pro
1               5                   10

<210> SEQ ID NO 10
<211> LENGTH: 10
<212> TYPE: PRT
<213> ORGANISM: human

<400> SEQUENCE: 10

Glu Ser Met Val Arg Asp Gly Met Asp Val
1               5                   10

<210> SEQ ID NO 11
<211> LENGTH: 5
<212> TYPE: PRT
<213> ORGANISM: human

<400> SEQUENCE: 11

Gly Tyr Tyr Trp Thr
1               5

<210> SEQ ID NO 12
<211> LENGTH: 16
<212> TYPE: PRT
<213> ORGANISM: human

<400> SEQUENCE: 12

Asp Ser Ser His Ser Gly Arg Thr Asn Tyr Asn Pro Ser Leu Lys Ser
1               5                   10                  15

<210> SEQ ID NO 13
<211> LENGTH: 9
<212> TYPE: PRT
<213> ORGANISM: human

<400> SEQUENCE: 13

Ala Glu Glu Thr Val Thr Ile Val Pro
1               5

<210> SEQ ID NO 14
<211> LENGTH: 5
<212> TYPE: PRT
<213> ORGANISM: human

<400> SEQUENCE: 14

Ser His Tyr Ile His
1               5

<210> SEQ ID NO 15
<211> LENGTH: 17
<212> TYPE: PRT
<213> ORGANISM: human

<400> SEQUENCE: 15

Gly Phe Ile Pro Ile Phe Gly Thr Ser Asn Tyr Ala Glu Lys Phe Lys Gly
1               5                   10                  15

<210> SEQ ID NO 16
<211> LENGTH: 15
<212> TYPE: PRT
<213> ORGANISM: human

<400> SEQUENCE: 16
```

```
Pro Arg Arg Ser Ser Ser Lys Thr Phe Ser Ala Leu Asp Tyr
1               5                   10                  15
```

<210> SEQ ID NO 17
<211> LENGTH: 5
<212> TYPE: PRT
<213> ORGANISM: human

<400> SEQUENCE: 17

```
Asp Tyr Ala Met Asn
1               5
```

<210> SEQ ID NO 18
<211> LENGTH: 15
<212> TYPE: PRT
<213> ORGANISM: human

<400> SEQUENCE: 18

```
Phe Ile Arg Ser Arg Gly Phe Gly Gly Thr Pro Glu Tyr Ala Ala
1               5                   10                  15
```

<210> SEQ ID NO 19
<211> LENGTH: 18
<212> TYPE: PRT
<213> ORGANISM: human

<400> SEQUENCE: 19

```
Asp Tyr Arg Pro Leu Gln Phe Trp Pro Gly Arg Gln Met Asp Ala Phe Asp Ile
1               5                   10                  15
```

<210> SEQ ID NO 20
<211> LENGTH: 5
<212> TYPE: PRT
<213> ORGANISM: human

<400> SEQUENCE: 20

```
Ser Tyr Trp Ile Asn
1               5
```

<210> SEQ ID NO 21
<211> LENGTH: 17
<212> TYPE: PRT
<213> ORGANISM: human

<400> SEQUENCE: 21

```
Met Ile Tyr Pro Ala Asp Ser Asp Thr Arg Tyr Ser Pro Ser Phe Gln Gly
1               5                   10                  15
```

<210> SEQ ID NO 22
<211> LENGTH: 10
<212> TYPE: PRT
<213> ORGANISM: human

<400> SEQUENCE: 22

```
Leu Gly Ile Gly Gly Arg Tyr Met Ser Arg
1               5                   10
```

<210> SEQ ID NO 23
<211> LENGTH: 5
<212> TYPE: PRT
<213> ORGANISM: human

<400> SEQUENCE: 23

```
Arg Tyr Tyr Ile His
1               5
```

```
<210> SEQ ID NO 24
<211> LENGTH: 17
<212> TYPE: PRT
<213> ORGANISM: human

<400> SEQUENCE: 24

Met Ile Asn Pro Arg Gly Gly Ser Thr Thr Tyr Ala Gln Lys Phe Gln Gly
1               5                   10                  15

<210> SEQ ID NO 25
<211> LENGTH: 14
<212> TYPE: PRT
<213> ORGANISM: human

<400> SEQUENCE: 25

Glu Ser Met Pro Gly Arg Asp Val Arg Asp Gly Met Asp Val
1               5                   10

<210> SEQ ID NO 26
<211> LENGTH: 5
<212> TYPE: PRT
<213> ORGANISM: human

<400> SEQUENCE: 26

Asp His Tyr Ile His
1               5

<210> SEQ ID NO 27
<211> LENGTH: 14
<212> TYPE: PRT
<213> ORGANISM: human

<400> SEQUENCE: 27

Pro Asn Ser Gly Ala Thr Lys Tyr Ala Gln Lys Phe His Gly
1               5                   10

<210> SEQ ID NO 28
<211> LENGTH: 9
<212> TYPE: PRT
<213> ORGANISM: human

<400> SEQUENCE: 28

Gly Ile Leu Leu Ala Arg Leu Asp Val
1               5

<210> SEQ ID NO 29
<211> LENGTH: 5
<212> TYPE: PRT
<213> ORGANISM: human

<400> SEQUENCE: 29

Asn Tyr Ala Ile Ser
1               5

<210> SEQ ID NO 30
<211> LENGTH: 17
<212> TYPE: PRT
<213> ORGANISM: human

<400> SEQUENCE: 30

Gly Thr Leu Leu Met Leu Arg Ile Ile Asn Ser Ala Gln Lys Phe Gln Gly
1               5                   10                  15
```

```
<210> SEQ ID NO 31
<211> LENGTH: 14
<212> TYPE: PRT
<213> ORGANISM: human

<400> SEQUENCE: 31

Ala Leu Pro Thr Ser Leu Gly Pro Ile Gly Tyr Leu His His
1               5                   10

<210> SEQ ID NO 32
<211> LENGTH: 5
<212> TYPE: PRT
<213> ORGANISM: human

<400> SEQUENCE: 32

Asp Tyr Tyr Met His
1               5

<210> SEQ ID NO 33
<211> LENGTH: 17
<212> TYPE: PRT
<213> ORGANISM: human

<400> SEQUENCE: 33

Trp Ile Asn Pro Asn Ile Gly Ala Thr Asn His Ala Gln Arg Phe Gln Gly
1               5                   10                  15

<210> SEQ ID NO 34
<211> LENGTH: 9
<212> TYPE: PRT
<213> ORGANISM: human

<400> SEQUENCE: 34

Asp Leu Gly Ile Ser Ala Phe Glu Asn
1               5

<210> SEQ ID NO 35
<211> LENGTH: 5
<212> TYPE: PRT
<213> ORGANISM: human

<400> SEQUENCE: 35

Asp Tyr Phe Met His
1               5

<210> SEQ ID NO 36
<211> LENGTH: 17
<212> TYPE: PRT
<213> ORGANISM: human

<400> SEQUENCE: 36

Trp Ile Asn Pro Asn Ser Gly Val Thr His Tyr Ala Gln Lys Phe Gln Gly
1               5                   10                  15

<210> SEQ ID NO 37
<211> LENGTH: 12
<212> TYPE: PRT
<213> ORGANISM: human

<400> SEQUENCE: 37

Glu Leu Ile Thr Gly Arg Leu Pro Thr Asp Asn Asp
1               5                   10

<210> SEQ ID NO 38
<211> LENGTH: 5
```

```
<212> TYPE: PRT
<213> ORGANISM: human

<400> SEQUENCE: 38

Gly Tyr Tyr Ile His
1               5

<210> SEQ ID NO 39
<211> LENGTH: 17
<212> TYPE: PRT
<213> ORGANISM: human

<400> SEQUENCE: 39

Trp Ile Asn Pro Asn Thr Gly Gly Thr Asn Tyr Ala Gln Lys Phe Gln Gly
1               5                   10                  15

<210> SEQ ID NO 40
<211> LENGTH: 18
<212> TYPE: PRT
<213> ORGANISM: human

<400> SEQUENCE: 40

Arg Ser Gly Gly Ser Gly Arg Tyr Trp Gly Ile Lys Asn Asn Trp Phe Asp Pro
1               5                   10                  15

<210> SEQ ID NO 41
<211> LENGTH: 17
<212> TYPE: PRT
<213> ORGANISM: human

<400> SEQUENCE: 41

Trp Ile Asn Pro Asn Ser Gly Val Thr His Tyr Ala Gln Lys Phe Gln Gly
1               5                   10                  15

<210> SEQ ID NO 42
<211> LENGTH: 12
<212> TYPE: PRT
<213> ORGANISM: human

<400> SEQUENCE: 42

Glu Leu Ile Ala Gly Arg Leu Pro Thr Asp Asn Asp
1               5                   10

<210> SEQ ID NO 43
<211> LENGTH: 5
<212> TYPE: PRT
<213> ORGANISM: human

<400> SEQUENCE: 43

Asp Tyr Tyr Phe His
1               5

<210> SEQ ID NO 44
<211> LENGTH: 17
<212> TYPE: PRT
<213> ORGANISM: human

<400> SEQUENCE: 44

Trp Ile Asn Phe Asp Ser Gly Gly Thr Asn Tyr Ala Gln Lys Phe Gln Gly
1               5                   10                  15

<210> SEQ ID NO 45
<211> LENGTH: 13
<212> TYPE: PRT
<213> ORGANISM: human
```

```
<400> SEQUENCE: 45

Gly Ser Arg Tyr Asn Ser Gly Trp Tyr Tyr Phe Asp Tyr
1               5                   10

<210> SEQ ID NO 46
<211> LENGTH: 5
<212> TYPE: PRT
<213> ORGANISM: human

<400> SEQUENCE: 46

Ile Ser Ser Pro Thr
1               5

<210> SEQ ID NO 47
<211> LENGTH: 16
<212> TYPE: PRT
<213> ORGANISM: human

<400> SEQUENCE: 47

Glu Ile Tyr His Ser Gly Thr Ser His His Asn Pro Ser Leu Lys Asn
1               5                   10                  15

<210> SEQ ID NO 48
<211> LENGTH: 11
<212> TYPE: PRT
<213> ORGANISM: human

<400> SEQUENCE: 48

Leu Asp Phe Asp Ser Pro Leu Gly Met Asp Ala
1               5                   10

<210> SEQ ID NO 49
<211> LENGTH: 11
<212> TYPE: PRT
<213> ORGANISM: human

<400> SEQUENCE: 49

Arg Ala Ser Gln Ser Ile Ser Thr Tyr Leu Asn
1               5                   10

<210> SEQ ID NO 50
<211> LENGTH: 7
<212> TYPE: PRT
<213> ORGANISM: human

<400> SEQUENCE: 50

Ala Ala Ser Ser Leu Gln Ser
1               5

<210> SEQ ID NO 51
<211> LENGTH: 9
<212> TYPE: PRT
<213> ORGANISM: human

<400> SEQUENCE: 51

Gln Gln Ser Tyr Ser Thr Pro Arg Thr
1               5

<210> SEQ ID NO 52
<211> LENGTH: 11
<212> TYPE: PRT
<213> ORGANISM: human

<400> SEQUENCE: 52
```

```
Arg Ala Ser Glu Asp Val Asn Ser Trp Leu Ala
1               5                   10

<210> SEQ ID NO 53
<211> LENGTH: 7
<212> TYPE: PRT
<213> ORGANISM: human

<400> SEQUENCE: 53

Gly Ser Thr Asn Leu Gln Gly
1               5

<210> SEQ ID NO 54
<211> LENGTH: 10
<212> TYPE: PRT
<213> ORGANISM: human

<400> SEQUENCE: 54

Lys Tyr Phe Asp Ala Leu Pro Pro Val Thr
1               5                   10

<210> SEQ ID NO 55
<211> LENGTH: 17
<212> TYPE: PRT
<213> ORGANISM: human

<400> SEQUENCE: 55

Thr Ser Ser Gln Ser Leu Leu Tyr Thr Ser Asn Asn Lys Asn Tyr Leu
1               5                   10                  15

Thr

<210> SEQ ID NO 56
<211> LENGTH: 7
<212> TYPE: PRT
<213> ORGANISM: human

<400> SEQUENCE: 56

Trp Ala Ser Thr Arg Glu Phe
1               5

<210> SEQ ID NO 57
<211> LENGTH: 9
<212> TYPE: PRT
<213> ORGANISM: human

<400> SEQUENCE: 57

Gln Gln Tyr Ser Asp Pro Pro Pro Thr
1               5

<210> SEQ ID NO 58
<211> LENGTH: 124
<212> TYPE: PRT
<213> ORGANISM: human
<220> FEATURE:
<223> OTHER INFORMATION: 7s1

<400> SEQUENCE: 58

Glu Val Gln Val Val Glu Ser Gly Ala Glu Val Lys Lys Pro Gly Ala
1               5                   10                  15

Ser Val Lys Val Ser Cys Lys Ala Ser Gly Tyr Thr Phe Asn Ser His
            20                  25                  30

Tyr Ile His Trp Val Arg Gln Ala Pro Gly Gln Gly Leu Glu Trp Met
        35                  40                  45
```

```
Gly Gly Phe Ile Pro Ile Phe Gly Thr Ser Asn Tyr Ala Glu Lys Phe
        50                  55                  60

Lys Gly Arg Val Thr Phe Thr Val Asp Thr Ser Thr Asn Thr Ala His
65                  70                  75                  80

Met Glu Leu Thr Arg Leu Arg Ser Glu Asp Thr Ala Ile Tyr Tyr Cys
                85                  90                  95

Ala Leu Pro Arg Arg Ser Ser Ser Lys Thr Phe Ser Ala Leu Asp
                100                 105                 110

Tyr Trp Gly Gln Gly Thr Leu Val Thr Val Ser Ser
            115                 120
```

<210> SEQ ID NO 59
<211> LENGTH: 129
<212> TYPE: PRT
<213> ORGANISM: human
<220> FEATURE:
<223> OTHER INFORMATION: 7s2

<400> SEQUENCE: 59

```
Gln Val Gln Leu Thr Glu Ser Gly Gly Leu Val Gln Pro Gly Arg
1               5                   10                  15

Ser Leu Arg Leu Ser Cys Thr Ala Ser Gly Phe Thr Leu Gly Asp Tyr
                20                  25                  30

Ala Met Asn Trp Val Arg Gln Ala Pro Gly Lys Gly Leu Glu Trp Val
            35                  40                  45

Gly Phe Ile Arg Ser Arg Gly Phe Gly Gly Thr Pro Glu Tyr Ala Ala
        50                  55                  60

Ser Val Lys Gly Arg Phe Thr Ile Ser Arg Asp Asn Ser Lys Gly Ile
65                  70                  75                  80

Ala Tyr Leu Glu Met Asn Ser Leu Lys Thr Glu Asp Thr Ala Met Tyr
                85                  90                  95

Tyr Cys Thr Arg Asp Tyr Arg Pro Leu Gln Phe Trp Pro Gly Arg Gln
                100                 105                 110

Met Asp Ala Phe Asp Ile Trp Gly Gln Gly Thr Met Val Thr Val Ser
            115                 120                 125

Ser
```

<210> SEQ ID NO 60
<211> LENGTH: 120
<212> TYPE: PRT
<213> ORGANISM: human
<220> FEATURE:
<223> OTHER INFORMATION: 7s4

<400> SEQUENCE: 60

```
Gln Val Gln Leu Val Glu Ser Gly Ala Glu Val Lys Lys Ala Gly Glu
1               5                   10                  15

Ser Leu Lys Ile Ser Cys Lys Gly Ser Gly Tyr Ser Phe Pro Ser Tyr
                20                  25                  30

Trp Ile Asn Trp Val Arg Gln Met Pro Gly Lys Gly Leu Glu Trp Met
            35                  40                  45

Gly Met Ile Tyr Pro Ala Asp Ser Asp Thr Arg Tyr Ser Pro Ser Phe
        50                  55                  60

Gln Gly His Val Thr Ile Ser Ala Asp Lys Ser Ile Asn Thr Ala Tyr
65                  70                  75                  80

Leu Gln Trp Ala Gly Leu Lys Ala Ser Asp Thr Ala Ile Tyr Tyr Cys
                85                  90                  95
```

```
Ala Arg Leu Gly Ile Gly Gly Arg Tyr Met Ser Arg Trp Gly Gln Gly
                100                 105                 110

Thr Leu Val Thr Val Ser Ser Ala
        115                 120

<210> SEQ ID NO 61
<211> LENGTH: 119
<212> TYPE: PRT
<213> ORGANISM: human
<220> FEATURE:
<223> OTHER INFORMATION: 7s7

<400> SEQUENCE: 61

Gln Val Gln Leu Val Gln Ser Gly Ala Glu Val Lys Lys Pro Gly Ala
1               5                   10                  15

Ser Val Lys Val Ser Cys Glu Ala Ser Gly Tyr Thr Phe Thr Arg Tyr
            20                  25                  30

Tyr Ile His Trp Val Arg Gln Ala Pro Gly Gln Gly Leu Glu Trp Met
        35                  40                  45

Gly Met Ile Asn Pro Arg Gly Gly Ser Thr Thr Tyr Ala Gln Lys Phe
    50                  55                  60

Gln Gly Arg Val Thr Met Thr Arg Asp Arg Ser Thr Ser Thr Val His
65                  70                  75                  80

Met Glu Val Ser Ser Leu Arg Ser Asp Asp Thr Ala Val Tyr Tyr Cys
                85                  90                  95

Ala Arg Glu Ser Met Val Arg Asp Gly Met Asp Val Trp Gly Gln Gly
                100                 105                 110

Thr Thr Val Thr Val Ser Ser
        115

<210> SEQ ID NO 62
<211> LENGTH: 118
<212> TYPE: PRT
<213> ORGANISM: human
<220> FEATURE:
<223> OTHER INFORMATION: 7s8

<400> SEQUENCE: 62

Glu Val Gln Leu Val Glu Ser Gly Ser Glu Val Lys Lys Pro Gly Ala
1               5                   10                  15

Ser Leu Lys Val Ser Cys Lys Ala Ser Gly Tyr Ser Phe Val Asp His
            20                  25                  30

Tyr Ile His Trp Val Arg Gln Ala Pro Gly Gln Gly Leu Glu Trp Met
        35                  40                  45

Gly Trp Leu Asn Pro Asn Ser Gly Ala Thr Lys Tyr Ala Gln Lys Phe
    50                  55                  60

His Gly Arg Val Thr Leu Thr Arg Asp Thr Ser Ile Ser Thr Val Tyr
65                  70                  75                  80

Met Glu Leu Ser Arg Leu Ile Ser Asp Asp Thr Ala Val Tyr Phe Cys
                85                  90                  95

Ala Arg Gly Ile Leu Leu Ala Arg Leu Asp Val Trp Gly Gln Gly Thr
                100                 105                 110

Leu Val Thr Val Ser Ser
        115

<210> SEQ ID NO 63
<211> LENGTH: 118
<212> TYPE: PRT
```

```
<213> ORGANISM: human
<220> FEATURE:
<223> OTHER INFORMATION: 7p2

<400> SEQUENCE: 63

Gln Val Gln Leu Val Gln Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
            20                  25                  30

Tyr Met Asp Trp Val Arg Gln Ala Pro Gly Lys Gly Leu Gln Trp Val
        35                  40                  45

Ala Ser Ile Lys Gln Asp Gly Ser Glu Thr Arg Tyr Gly Asp Ser Val
    50                  55                  60

Arg Gly Arg Phe Ile Ile Ser Arg Asp Asn Thr Lys Asn Ser Ala Tyr
65                  70                  75                  80

Leu Gln Met Asn Thr Leu Ser Ala Glu Asp Arg Ala Val Tyr His Cys
                85                  90                  95

Val Arg Glu Leu Asp Gly Gly Phe Phe Asp Phe Trp Gly Gln Gly Thr
            100                 105                 110

Leu Val Thr Val Ser Ser
        115

<210> SEQ ID NO 64
<211> LENGTH: 121
<212> TYPE: PRT
<213> ORGANISM: human
<220> FEATURE:
<223> OTHER INFORMATION: 7p3

<400> SEQUENCE: 64

Gln Val Gln Leu Gln Glu Ser Gly Pro Gly Leu Val Lys Pro Ser Glu
 1               5                  10                  15

Thr Leu Ser Leu Thr Cys Ser Val Ser Gly Ala Ser Met Ser Arg Phe
            20                  25                  30

Tyr Trp Asn Trp Ile Arg His Ser Ala Gly Lys Gly Leu Glu Trp Ile
        35                  40                  45

Gly Arg Ile Phe Thr Asn Gly Thr Thr Asn Tyr Asn Pro Ser Leu Gly
    50                  55                  60

Ser Arg Val Thr Met Ser Val Asp Thr Ala Lys Asn Gln Phe Ser Leu
65                  70                  75                  80

Arg Val Thr Ser Val Thr Ala Ala Asp Ala Ala Val Tyr Tyr Cys Ala
                85                  90                  95

Arg Gly Gly Asp Tyr Gly Pro Ala Leu Ala Trp Phe Asp Pro Trp Gly
            100                 105                 110

Gln Gly Thr Leu Val Thr Val Ser Ser
        115                 120

<210> SEQ ID NO 65
<211> LENGTH: 124
<212> TYPE: PRT
<213> ORGANISM: human
<220> FEATURE:
<223> OTHER INFORMATION: 7p4

<400> SEQUENCE: 65

Gln Val Gln Leu Gln Glu Trp Gly Gly Gly Val Val Gln Pro Gly Arg
 1               5                  10                  15

Ser Leu Arg Leu Ser Cys Val Ala Ser Gly Phe Thr Phe Ser Gly His
            20                  25                  30
```

```
Trp Met His Trp Val Arg Gln Ala Pro Gly Lys Gly Leu Val Trp Val
            35                  40                  45

Ser Arg Ile Asp Glu His Gly Ser Ser Ala Tyr Tyr Ala Asp Ser Val
 50                  55                  60

Asn Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Phe Ile Thr Pro Glu Val Val His Trp Ser Ser Asp
            100                 105                 110

Ile Trp Gly Gln Gly Thr Met Val Thr Val Ser Ser
            115                 120
```

<210> SEQ ID NO 66
<211> LENGTH: 119
<212> TYPE: PRT
<213> ORGANISM: human
<220> FEATURE:
<223> OTHER INFORMATION: 7p7

<400> SEQUENCE: 66

```
Gln Val Gln Leu Val Gln Ser Gly Ala Glu Val Lys Lys Pro Gly Ala
1               5                   10                  15

Ser Val Lys Val Ser Cys Glu Ala Ser Gly Tyr Thr Phe Thr Arg Tyr
            20                  25                  30

Tyr Ile His Trp Val Arg Gln Ala Pro Gly Gln Gly Leu Glu Trp Met
            35                  40                  45

Gly Met Ile Asn Pro Arg Gly Gly Ser Thr Thr Tyr Ala Gln Lys Phe
 50                  55                  60

Gln Gly Arg Val Thr Met Thr Arg Asp Arg Ser Thr Ser Thr Val His
65                  70                  75                  80

Met Glu Val Ser Ser Leu Arg Ser Asp Asp Thr Ala Val Tyr Tyr Cys
                85                  90                  95

Ala Arg Glu Ser Met Val Arg Asp Gly Met Asp Val Trp Gly Gln Gly
            100                 105                 110

Thr Thr Val Thr Val Ser Ser
            115
```

<210> SEQ ID NO 67
<211> LENGTH: 128
<212> TYPE: PRT
<213> ORGANISM: human
<220> FEATURE:
<223> OTHER INFORMATION: 7p8

<400> SEQUENCE: 67

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Thr Trp Ile Arg Gln Pro Pro Gly Lys Gly Leu Glu Trp Ile
            35                  40                  45

Gly Asp Ser Ser His Ser Gly Arg Thr Asn Tyr Asn Pro Ser Leu Lys
 50                  55                  60

Ser Arg Val Thr Ile Ser Val Asp Ala Ser Lys Lys Gln Phe Ser Leu
65                  70                  75                  80

Lys Leu Ile Ser Val Thr Ala Ala Glu Pro Phe Arg Ser Ser Ser Glu
```

```
                    85                  90                  95
Met Ser Phe Cys Ser Leu Ala Glu Glu Thr Val Thr Ile Val Pro Trp
                100                 105                 110

Pro Gln Thr Ser Lys Ala Pro Pro Asn Arg Pro Arg Cys Phe Val Ser
            115                 120                 125

<210> SEQ ID NO 68
<211> LENGTH: 125
<212> TYPE: PRT
<213> ORGANISM: human
<220> FEATURE:
<223> OTHER INFORMATION: 10s1

<400> SEQUENCE: 68

Gly Ala Ala Gly Glu Ser Gly Ala Glu Val Arg Lys Pro Gly Ser Ser
1               5                   10                  15

Val Lys Val Ser Cys Lys Ala Ser Gly Gly Ser Ile Asn Asn Tyr Ala
            20                  25                  30

Ile Ser Trp Val Arg Gln Ala Pro Gly Gln Gly Leu Glu Trp Ile Gly
        35                  40                  45

Gly Thr Leu Leu Met Leu Arg Ile Ile Asn Ser Ala Gln Lys Phe Gln
    50                  55                  60

Gly Arg Val Ser Ile Thr Ala Asp Thr Ser Thr Asn Thr Ala Tyr Met
65                  70                  75                  80

Glu Leu Ser Ser Leu Arg Ser Glu Asp Thr Ala Met Tyr Tyr Cys Ala
                85                  90                  95

Ser Ser Val Ala Ala Leu Pro Thr Ser Leu Gly Pro Ile Gly Tyr Leu
            100                 105                 110

His His Trp Gly Gln Gly Thr Leu Val Thr Val Ser Ser
        115                 120                 125

<210> SEQ ID NO 69
<211> LENGTH: 117
<212> TYPE: PRT
<213> ORGANISM: human
<220> FEATURE:
<223> OTHER INFORMATION: 10s2

<400> SEQUENCE: 69

Gly Ala Gly Gly Glu Ser Gly Ala Asp Val Lys Lys Pro Gly Ala Ser
1               5                   10                  15

Val Lys Val Ser Cys Lys Ala Ser Gly Tyr Thr Phe Thr Asp Tyr Tyr
            20                  25                  30

Met His Trp Val Arg Gln Ala Pro Gly Gln Gly Leu Glu Trp Met Gly
        35                  40                  45

Trp Ile Asn Pro Asn Ile Gly Ala Thr Asn His Ala Gln Arg Phe Gln
    50                  55                  60

Gly Arg Leu Thr Val Ser Arg Asp Thr Ser Ile Thr Thr Val Tyr Met
65                  70                  75                  80

Glu Leu Ser Arg Leu Gln Ser Asp Asp Thr Ala Val Tyr Phe Cys Ala
                85                  90                  95

Arg Asp Leu Gly Ile Ser Ala Phe Glu Asn Trp Gly Gln Gly Thr Met
            100                 105                 110

Val Thr Val Ser Ser
        115

<210> SEQ ID NO 70
<211> LENGTH: 120
```

```
<212> TYPE: PRT
<213> ORGANISM: human
<220> FEATURE:
<223> OTHER INFORMATION: 10s3

<400> SEQUENCE: 70

Gly Asp Gly Gly Glu Ser Gly Ala Glu Val Arg Lys Pro Gly Ala Ser
1               5                   10                  15

Val Lys Val Ser Cys Lys Ala Ser Arg Tyr Ser Phe Thr Asp Tyr Phe
            20                  25                  30

Met His Trp Val Arg Gln Ala Pro Gly Gln Gly Leu Glu Trp Met Gly
        35                  40                  45

Trp Ile Asn Pro Asn Ser Gly Val Thr His Tyr Ala Gln Lys Phe Gln
    50                  55                  60

Gly Arg Val Thr Met Thr Arg Asp Thr Ser Ile Asn Thr Ala Tyr Met
65                  70                  75                  80

Glu Val Ser Arg Leu Arg Tyr Asp Asp Thr Ala Val Tyr Tyr Cys Thr
                85                  90                  95

Arg Glu Leu Ile Thr Gly Arg Leu Pro Thr Asp Asn Asp Trp Gly Gln
            100                 105                 110

Gly Thr Leu Val Thr Val Ser Ser
        115                 120

<210> SEQ ID NO 71
<211> LENGTH: 126
<212> TYPE: PRT
<213> ORGANISM: human
<220> FEATURE:
<223> OTHER INFORMATION: 10s4

<400> SEQUENCE: 71

Gly Ala Ala Gly Glu Ser Gly Ala Glu Val Arg Lys Pro Gly Ala Ser
1               5                   10                  15

Val Lys Val Ser Cys Lys Thr Ser Gly Tyr Asn Phe Arg Gly Tyr Tyr
            20                  25                  30

Ile His Trp Val Arg Gln Ala Pro Gly Gln Gly Leu Glu Trp Met Gly
        35                  40                  45

Trp Ile Asn Pro Asn Thr Gly Thr Asn Tyr Ala Gln Lys Phe Gln
    50                  55                  60

Gly Arg Val Thr Met Thr Arg Asp Thr Ser Ile Asn Thr Ala Tyr Met
65                  70                  75                  80

Glu Val Ser Lys Leu Arg Ser Asp Asp Thr Ala Val Tyr Tyr Cys Ala
                85                  90                  95

Arg Arg Ser Gly Gly Ser Gly Arg Tyr Trp Gly Ile Lys Asn Asn Trp
            100                 105                 110

Phe Asp Pro Trp Gly Gln Gly Thr Leu Val Thr Val Ser Ser
        115                 120                 125

<210> SEQ ID NO 72
<211> LENGTH: 120
<212> TYPE: PRT
<213> ORGANISM: human
<220> FEATURE:
<223> OTHER INFORMATION: 10s5

<400> SEQUENCE: 72

Gly Asp Gly Gly Glu Ser Gly Ala Glu Val Arg Lys Pro Gly Ala Ser
1               5                   10                  15

Val Lys Val Ser Cys Lys Ala Ser Arg Tyr Ser Phe Thr Asp Tyr Phe
```

```
                    20                  25                  30
Met His Trp Val Arg Gln Ala Pro Gly Gln Gly Leu Glu Trp Met Gly
            35                  40                  45

Trp Ile Asn Pro Asn Ser Gly Val Thr His Tyr Ala Gln Lys Phe Gln
        50                  55                  60

Gly Arg Val Thr Met Thr Arg Asp Thr Ser Ile Asn Thr Ala Tyr Met
65                  70                  75                  80

Glu Val Ser Arg Leu Arg Tyr Asp Asp Thr Ala Val Tyr Tyr Cys Thr
                85                  90                  95

Arg Glu Leu Ile Ala Gly Arg Leu Pro Thr Asp Asn Asp Trp Gly Gln
            100                 105                 110

Gly Thr Leu Val Thr Val Ser Ser
        115                 120

<210> SEQ ID NO 73
<211> LENGTH: 122
<212> TYPE: PRT
<213> ORGANISM: human
<220> FEATURE:
<223> OTHER INFORMATION: 10p1

<400> SEQUENCE: 73

Gln Val Gln Leu Val Gln Ser Gly Ala Glu Val Lys Lys Pro Gly Ala
1               5                   10                  15

Ser Val Lys Val Ser Cys Lys Ala Ala Gly Tyr Thr Phe Thr Asp Tyr
            20                  25                  30

Tyr Phe His Trp Val Arg Gln Ala Pro Gly Gln Gly Leu Glu Trp Met
        35                  40                  45

Gly Trp Ile Asn Pro Asp Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Asp Leu Ser Arg Leu Arg Ser Asp Asp Thr Ala Val Cys Tyr Cys
                85                  90                  95

Ala Arg Gly Ser Arg Tyr Asn Ser Gly Trp Tyr Tyr Phe Asp Tyr Trp
            100                 105                 110

Ser Arg Gly Thr Leu Val Thr Val Ser Ser
        115                 120

<210> SEQ ID NO 74
<211> LENGTH: 120
<212> TYPE: PRT
<213> ORGANISM: human
<220> FEATURE:
<223> OTHER INFORMATION: 10p2

<400> SEQUENCE: 74

Gln Val Gln Leu Gln Glu Trp Gly Pro Gly Leu Val Lys Pro Ser Gly
1               5                   10                  15

Thr Leu Ser Leu Thr Cys Ala Val Ser Gly Gly Thr Ile Ser Ser Pro
            20                  25                  30

Thr Trp Trp Asn Trp Val Arg Gln Pro Pro Gly Lys Gly Leu Glu Trp
        35                  40                  45

Ile Gly Glu Ile Tyr His Ser Gly Thr Ser His Asn Pro Ser Leu
    50                  55                  60

Lys Asn Arg Val Thr Leu Ser Val Asp Lys Ser Lys Asn Gln Phe Ser
65                  70                  75                  80
```

```
Leu Lys Leu Asn Ser Met Thr Ala Ala Asp Thr Ala Val Tyr Phe Cys
                85                  90                  95

Thr Arg Leu Asp Phe Asp Ser Pro Leu Gly Met Asp Ala Trp Gly Gln
            100                 105                 110

Gly Thr Thr Val Thr Val Ser Ser
            115             120
```

<210> SEQ ID NO 75
<211> LENGTH: 109
<212> TYPE: PRT
<213> ORGANISM: human
<220> FEATURE:
<223> OTHER INFORMATION: No. 4

<400> SEQUENCE: 75

```
Asp Ile Val Met Thr Arg Ser Pro Ser Ser Leu Ser Ala Ser Val Gly
1               5                   10                  15

Asp Arg Val Thr Ile Thr Cys Arg Ala Ser Gln Ser Ile Ser Thr Tyr
            20                  25                  30

Leu Asn Trp Tyr Gln Gln Lys Ala Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Arg
                85                  90                  95

Thr Phe Gly Gln Gly Thr Lys Val Glu Ile Lys Arg Ala
            100                 105
```

<210> SEQ ID NO 76
<211> LENGTH: 110
<212> TYPE: PRT
<213> ORGANISM: human
<220> FEATURE:
<223> OTHER INFORMATION: No.7

<400> SEQUENCE: 76

```
Glu Ile Val Leu Thr Gln Ser Pro Ser Ser Val Ser Ala Ser Val Gly
1               5                   10                  15

Asp Arg Val Thr Ile Thr Cys Arg Ala Ser Glu Asp Val Asn Ser Trp
            20                  25                  30

Leu Ala Trp Tyr Gln Gln Lys Pro Gly Lys Ala Pro Lys Leu Leu Ile
        35                  40                  45

Tyr Gly Ser Thr Asn Leu Gln Gly Gly Val Pro Ser Arg Phe Ser Gly
    50                  55                  60

Arg Gly Ser Gly Thr His Phe Thr Phe Thr Ile Asn Gly Leu Gln Pro
65                  70                  75                  80

Glu Asp Ile Ala Thr Tyr Tyr Cys Lys Tyr Phe Asp Ala Leu Pro Pro
                85                  90                  95

Val Thr Phe Gly Gln Gly Thr Arg Leu Glu Ile Lys Arg Ala
            100                 105                 110
```

<210> SEQ ID NO 77
<211> LENGTH: 115
<212> TYPE: PRT
<213> ORGANISM: human
<220> FEATURE:
<223> OTHER INFORMATION: No.10

<400> SEQUENCE: 77

Asp Ile Val Leu Thr Gln Ser Pro Asp Ser Leu Ala Val Ser Leu Gly
1               5                   10                  15

Glu Arg Ala Thr Ile Asn Cys Thr Ser Ser Gln Ser Leu Leu Tyr Thr
            20                  25                  30

Ser Asn Asn Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Phe Gly Val
    50                  55                  60

Pro Asp Arg Phe Ser Gly Ser Gly Ser Gly Thr Asp Phe Thr Leu Thr
65                  70                  75                  80

Ile Asn Ser Leu Gln Ala Glu Asp Val Ala Thr Tyr Tyr Cys Gln Gln
                85                  90                  95

Tyr Ser Asp Pro Pro Thr Phe Gly Gly Thr Lys Leu Glu Ile
            100                 105                 110

Lys Arg Ala
        115

<210> SEQ ID NO 78
<211> LENGTH: 52
<212> TYPE: DNA
<213> ORGANISM: artificial sequence
<220> FEATURE:
<223> OTHER INFORMATION: synthesized DNA

<400> SEQUENCE: 78
tcgcaactgc ggcccagccg gccatggccc aggtgcagct ggtgcagtct gg          52

<210> SEQ ID NO 79
<211> LENGTH: 52
<212> TYPE: DNA
<213> ORGANISM: artificial sequence
<220> FEATURE:
<223> OTHER INFORMATION: synthesized DNA

<400> SEQUENCE: 79
tcgcaactgc ggcccagccg gccatggccc agrtycagct ggtgcagtct gg          52

<210> SEQ ID NO 80
<211> LENGTH: 52
<212> TYPE: DNA
<213> ORGANISM: artificial sequence
<220> FEATURE:
<223> OTHER INFORMATION: synthesized DNA

<400> SEQUENCE: 80
tcgcaactgc ggcccagccg gccatggccc agstrcagct gcagsagtcr gg          52

<210> SEQ ID NO 81
<211> LENGTH: 52
<212> TYPE: DNA
<213> ORGANISM: artificial sequence
<220> FEATURE:
<223> OTHER INFORMATION: synthesized DNA

<400> SEQUENCE: 81
tcgcaactgc ggcccagccg gccatggccs argtgcagkt ggtggagtct gg          52

<210> SEQ ID NO 82
<211> LENGTH: 52
<212> TYPE: DNA
<213> ORGANISM: artificial sequence
<220> FEATURE:
<223> OTHER INFORMATION: synthesized DNA

<400> SEQUENCE: 82
tcgcaactgc ggcccagccg gccatggccc cagtgtgagg tgcagctggt gg    52

<210> SEQ ID NO 83
<211> LENGTH: 52
<212> TYPE: DNA
<213> ORGANISM: artificial sequence
<220> FEATURE:
<223> OTHER INFORMATION: synthesized DNA

<400> SEQUENCE: 83
tcgcaactgc ggcccagccg gccatggccc aggtgcagct acagsagtgg gg    52

<210> SEQ ID NO 84
<211> LENGTH: 40
<212> TYPE: DNA
<213> ORGANISM: artificial sequence
<220> FEATURE:
<223> OTHER INFORMATION: synthesized DNA

<400> SEQUENCE: 84
attctcgact gctagctgag gagacggtga ccagggtgcc    40

<210> SEQ ID NO 85
<211> LENGTH: 40
<212> TYPE: DNA
<213> ORGANISM: artificial sequence
<220> FEATURE:
<223> OTHER INFORMATION: synthesized DNA

<400> SEQUENCE: 85
attctcgact gctagctgaa gagacggtga ccattgtccc    40

<210> SEQ ID NO 86
<211> LENGTH: 40
<212> TYPE: DNA
<213> ORGANISM: artificial sequence
<220> FEATURE:
<223> OTHER INFORMATION: synthesized DNA

<400> SEQUENCE: 86
attctcgact gctagctgag gagacggtga ccagggttcc    40

<210> SEQ ID NO 87
<211> LENGTH: 40
<212> TYPE: DNA
<213> ORGANISM: artificial sequence
<220> FEATURE:
<223> OTHER INFORMATION: synthesized DNA

<400> SEQUENCE: 87
attctcgact gctagctgag gagacggtga ccgtggtccc    40

<210> SEQ ID NO 88
<211> LENGTH: 22
<212> TYPE: DNA
<213> ORGANISM: artificial sequence
<220> FEATURE:
<223> OTHER INFORMATION: synthesized DNA

<400> SEQUENCE: 88
ccgctggatt gttattactc gc    22

<210> SEQ ID NO 89
<211> LENGTH: 52
<212> TYPE: DNA
<213> ORGANISM: artificial sequence
<220> FEATURE:
<223> OTHER INFORMATION: synthesized DNA

<400> SEQUENCE: 89
tcgcaactgc ggcccagccg gccatggccg mcatycagwt gacccagtct cc            52

<210> SEQ ID NO 90
<211> LENGTH: 52
<212> TYPE: DNA
<213> ORGANISM: artificial sequence
<220> FEATURE:
<223> OTHER INFORMATION: synthesized DNA

<400> SEQUENCE: 90
tcgcaactgc ggcccagccg gccatggccg atrttgtgat gacycagwct cc            52

<210> SEQ ID NO 91
<211> LENGTH: 52
<212> TYPE: DNA
<213> ORGANISM: artificial sequence
<220> FEATURE:
<223> OTHER INFORMATION: synthesized DNA

<400> SEQUENCE: 91
tcgcaactgc ggcccagccg gccatggccg aaattgtgwt gacgcagtct cc            52

<210> SEQ ID NO 92
<211> LENGTH: 52
<212> TYPE: DNA
<213> ORGANISM: artificial sequence
<220> FEATURE:
<223> OTHER INFORMATION: synthesized DNA

<400> SEQUENCE: 92
tcgcaactgc ggcccagccg gccatggccg acatcgwght gacccagtct cc            52

<210> SEQ ID NO 93
<211> LENGTH: 42
<212> TYPE: DNA
<213> ORGANISM: artificial sequence
<220> FEATURE:
<223> OTHER INFORMATION: synthesized DNA

<400> SEQUENCE: 93
ttctcgactt gcggccgcac gtttgatttc caccttggtc cc                      42

<210> SEQ ID NO 94
<211> LENGTH: 42
<212> TYPE: DNA
<213> ORGANISM: artificial sequence
<220> FEATURE:
<223> OTHER INFORMATION: synthesized DNA

<400> SEQUENCE: 94
ttctcgactt gcggccgcac gtttgatctc cagcttggtc cc                      42

<210> SEQ ID NO 95
<211> LENGTH: 42
<212> TYPE: DNA
<213> ORGANISM: artificial sequence
<220> FEATURE:
<223> OTHER INFORMATION: synthesized DNA

```
<400> SEQUENCE: 95
ttctcgactt gcggccgcac gtttgatatc cactttggtc cc                              42

<210> SEQ ID NO 96
<211> LENGTH: 42
<212> TYPE: DNA
<213> ORGANISM: artificial sequence
<220> FEATURE:
<223> OTHER INFORMATION: synthesized DNA

<400> SEQUENCE: 96
ttctcgactt gcggccgcac gtttgatctcc accttggtc cc                              42

<210> SEQ ID NO 97
<211> LENGTH: 42
<212> TYPE: DNA
<213> ORGANISM: artificial sequence
<220> FEATURE:
<223> OTHER INFORMATION: synthesized DNA

<400> SEQUENCE: 97
ttctcgactt gcggccgcac gtttaatctc cagtcgtgtc cc                              42

<210> SEQ ID NO 98
<211> LENGTH: 372
<212> TYPE: DNA
<213> ORGANISM: human
<220> FEATURE:
<223> OTHER INFORMATION: d7s1

<400> SEQUENCE: 98
gaggtgcagg tggtggagtc tgggctgag gtgaagaagc ctggggcctc agtgaaggtt            60
tcgtgcaagg cttccggata caccttcaac agtcactata tccactgggt gcgacaggcc          120
cctggacaag gcttgagtg gatgggggg ttcatccta tctttggcac atcaaattac             180
gcagagaagt tcaagggcag agtcaccttt accgtggaca cgtccacgaa tacagcgcac          240
atggaactga ccagactgag atctgaggac acggccatat attactgtgc actacccgg           300 aggagcagct cgtccaagac tttctcggcc cttgactact ggggccaggg caccctggtc          360
accgtctcct ca                                                              372

<210> SEQ ID NO 99
<211> LENGTH: 387
<212> TYPE: DNA
<213> ORGANISM: human
<220> FEATURE:
<223> OTHER INFORMATION: d7s2

<400> SEQUENCE: 99
caggtgcagc tgacggagtc ggggggaggc ttggtacagc cagggcggtc cctaagactc           60
tcctgtacag cctctggatt caccccttggt gattatgcta tgaactgggt ccgccaggct         120
ccagggaagg ggctggagtg gtaggtttc attcgaagca gaggtttcgg tgggactcca          180
gaatacgccg cgtctgtaaa aggcagattc accatctcaa gagataattc caaaggcatc         240
gcctatctgg aaatgaacag cctgaaaacc gaggacacag ccatgtatta ctgtactaga         300
gattatcgcc cattacaatt ttggcccgga cgacaaatgg atgcttttga tatttggggc         360
caagggacaa tggtcaccgt ctcttca                                              387

<210> SEQ ID NO 100
```

<211> LENGTH: 357
<212> TYPE: DNA
<213> ORGANISM: human
<220> FEATURE:
<223> OTHER INFORMATION: d7s4

<400> SEQUENCE: 100

| caggtgcagt tggtggagtc tggagcagag gtgaaaaagg ccggggagtc tctgaagatc | 60 |
| tcctgtaagg gatctggata cagctttccc agttactgga tcaactgggt gcgccagatg | 120 |
| cccggcaaag gcctggaatg gatggggatg atctatcctg ctgactctga taccagatat | 180 |
| agcccgtcct tccaaggcca cgtcaccatc tcagccgaca gtccatcaa caccgcctac | 240 |
| ctgcaatggg ccggcctgaa ggcctcggac accgccatat attactgtgc gagacttgga | 300 |
| attggtggga ggtacatgtc tagatggggc cagggaaccc tggtcaccgt ctcctca | 357 |

<210> SEQ ID NO 101
<211> LENGTH: 357
<212> TYPE: DNA
<213> ORGANISM: human
<220> FEATURE:
<223> OTHER INFORMATION: d7s7

<400> SEQUENCE: 101

| caggtgcagc tggtgcagtc tggggctgag gtgaagaagc ctggggcctc agtgaaggtt | 60 |
| tcctgcgagg catctggata cactttcacc aggtactata tacactgggt gcgacaggcc | 120 |
| cctggacaag gcttgagtg gatgggaatg attaaccctc gtggtggtag cacaacctac | 180 |
| gcacagaagt tccagggcag agtcaccatg accagggaca ggtccacgag cacagtccac | 240 |
| atggaagtga gcagcctgag atctgacgac acggccgtat attactgtgc gagggagagc | 300 |
| atggttcggg acggtatgga cgtctggggc caagggacca cggtcaccgt ctcctca | 357 |

<210> SEQ ID NO 102
<211> LENGTH: 354
<212> TYPE: DNA
<213> ORGANISM: human
<220> FEATURE:
<223> OTHER INFORMATION: d7s8

<400> SEQUENCE: 102

| gaagtgcagt tggtggagtc tgggtctgag gtgaagaagc ctggggcctc actgaaagtc | 60 |
| tcctgcaagg cctctggata cagcttcgtc gaccactaca tccactgggt gcgacaggcc | 120 |
| cctggacaag gcttgagtg gatggatgg ctcaatccta atagtggtgc cacaaaatat | 180 |
| gcacagaaat ttcatggcag ggtcaccctg accagggaca cgtccatcag cacagtctac | 240 |
| atggaactga gcagactgat atctgacgac acggccgtat atttctgtgc gaggggaatt | 300 |
| ttactagccc gtttggacgt ctggggccaa ggcaccctgg tcaccgtctc ctca | 354 |

<210> SEQ ID NO 103
<211> LENGTH: 354
<212> TYPE: DNA
<213> ORGANISM: human
<220> FEATURE:
<223> OTHER INFORMATION: d7p2

<400> SEQUENCE: 103

| caggtccagc tggtgcagtc tggggaggc ttggtccagc ctggagggtc cctgagactc | 60 |
| tcctgtgcag cctctggatt caccttcagt gattactaca tggactgggt ccgccaggct | 120 |
| ccagggaaag gcctgcagtg ggtggccagt ataaagcagg atggaagtga gacacgttat | 180 |

| | |
|---|---|
| gggggactctg tgagggggccg cttcatcata tccagagaca acaccaagaa ctcggcgtat | 240 |
| ctgcaaatga acaccctgag cgccgaagac agggccgtgt atcactgtgt gagagaactt | 300 |
| gatgggggat tctttgactt ctggggccag ggaaccctgg tcaccgtctc ctca | 354 |

<210> SEQ ID NO 104
<211> LENGTH: 363
<212> TYPE: DNA
<213> ORGANISM: human
<220> FEATURE:
<223> OTHER INFORMATION: d7p3

<400> SEQUENCE: 104

| | |
|---|---|
| caggtgcagc tgcaggagtc gggcccagga ctggtgaagc cttcggagac cctgtccctc | 60 |
| acctgcagtg tctctggtgc ctccatgagt cgtttctact ggaattggat ccgacactcc | 120 |
| gccgggaagg gactggaatg gattggacga atctttacta atgggaccac caactacaac | 180 |
| ccctccctgg ggagtcgagt caccatgtca gttgacacgg ccaaaaacca gttctccctc | 240 |
| agagtgacct ctgtgaccgc cgcggacgcg gccgtctatt actgtgcgag aggaggcgac | 300 |
| tacggtcctg cgttggcctg gttcgacccc tggggccaag caccctggt caccgtctcc | 360 |
| tca | 363 |

<210> SEQ ID NO 105
<211> LENGTH: 372
<212> TYPE: DNA
<213> ORGANISM: human
<220> FEATURE:
<223> OTHER INFORMATION: d7p4

<400> SEQUENCE: 105

| | |
|---|---|
| caggtgcagc tacaggagtg gggggggaggc gtggtccagc ctggcaggtc cctgagactc | 60 |
| tcctgtgtcg cctctggatt caccttcagt ggccactgga tgcactgggt ccgccaagct | 120 |
| ccagggaagg ggctggtgtg ggtctcgcgt attgatgaac atgggagcag cgcatactac | 180 |
| gcggactccg tgaacggccg attcaccatc tccagagaca cgccaagaa cacgctgtat | 240 |
| ttgcaaatga acagtctgag agccgaggat acggctgtgt attactgtgc aagattaggg | 300 |
| tttattaccc ccgaagtggt ccactggtcc tccgatatct ggggccaagg gacaatggtc | 360 |
| accgtctctt ca | 372 |

<210> SEQ ID NO 106
<211> LENGTH: 357
<212> TYPE: DNA
<213> ORGANISM: human
<220> FEATURE:
<223> OTHER INFORMATION: d7p7

<400> SEQUENCE: 106

| | |
|---|---|
| caggtgcagc tggtgcagtc tggggctgag gtgaagaagc ctggggcctc agtgaaggtt | 60 |
| tcctgcgagg catctggata cactttcacc aggtactata tacactgggt gcgacaggcc | 120 |
| cctggacaag gcttgagtg gatgggaatg attaaccctc gtggtggtag cacaacctac | 180 |
| gcacagaagt tccagggcag agtcaccatg accagggaca ggtccacgag cacagtccac | 240 |
| atggaagtga gcagcctgag atctgacgac acggccgtat attactgtgc gagggagagc | 300 |
| atggttcggg acggtatgga cgtctggggc caagggacca cggtcaccgt ctcctca | 357 |

<210> SEQ ID NO 107

```
<211> LENGTH: 375
<212> TYPE: DNA
<213> ORGANISM: human
<220> FEATURE:
<223> OTHER INFORMATION: d10s1

<400> SEQUENCE: 107
ggtgcagctg gtgagtctgg ggctgaggtg aggaagcctg ggtcctcggt gaaggtctcc      60
tgcaaggctt ctggaggcag catcaacaac tatgctatca gctgggtgcg acaggcccct     120
ggacaagggc ttgagtggat tggagggacc ctcctcatgc tccgtattat aaactccgca     180
cagaagttcc agggcagagt ctcgattacc gcggacacat ccacgaacac ggcctacatg     240
gaactgagca gcctgagatc tgaggacacg gccatgtatt attgtgcgag cagtgtcgca     300
gcacttccaa cttctcttgg cccaatcgga tacctccacc attggggcca gggcaccctg     360
gtcaccgtct cctca                                                      375

<210> SEQ ID NO 108
<211> LENGTH: 351
<212> TYPE: DNA
<213> ORGANISM: human
<220> FEATURE:
<223> OTHER INFORMATION: d10s2

<400> SEQUENCE: 108
ggtgcaggtg gtgagtctgg ggctgacgtg aagaagcctg gggcctcagt aaaggtctcc      60
tgcaaggctt ccggatacac cttcaccgac tactatatgc actgggtgcg acaggcccct     120
ggacaagggc ttgagtggat ggggtggatc aaccctaaca ttggtgccac aaaccatgca     180
cagaggtttc agggcaggct caccgtgagt agggacacgt ccatcaccac agtctacatg     240
gagctgagca ggctacagtc tgacgacacg gccgtctatt tttgtgcgag agatctgggg     300
atctctgctt ttgagaactg gggccaaggg acaatggtca ccgtctcttc a              351

<210> SEQ ID NO 109
<211> LENGTH: 360
<212> TYPE: DNA
<213> ORGANISM: human
<220> FEATURE:
<223> OTHER INFORMATION: d10s3

<400> SEQUENCE: 109
ggtgacggtg gtgagtctgg ggctgaggtg aggaagcctg gggcctcagt gaaggtctcc      60
tgcaaggcct ctagatacag cttcaccgac tactttatgc actgggtgcg acaggcccct     120
ggacaagggc ttgagtggat gggatggatc aaccctaaca gtggtgtcac acactatgca     180
cagaagtttc agggcagggt caccatgacc agggacacgt ccatcaacac agcctacatg     240
gaagtgagca ggctgagata tgacgacacg gccgtgtatt actgtacgag agaactgata     300
acaggtcgtc tgccaactga caacgactgg ggccagggaa ccctggtcac cgtctcctca     360

<210> SEQ ID NO 110
<211> LENGTH: 378
<212> TYPE: DNA
<213> ORGANISM: human
<220> FEATURE:
<223> OTHER INFORMATION: d10s4

<400> SEQUENCE: 110
ggtgcagctg gtgagtctgg ggctgaggtg aggaagcctg gggcctcagt gaaggtctcc      60
tgcaagactt ccggatataa cttcagggc tactacatac attgggtgcg acaggcccct     120
```

```
ggacaagggc ttgagtggat gggatggatc aacccgaaca ctggtggcac aaactatgca    180
cagaagtttc agggcagggt caccatgacc agggacacgt ccatcaacac agcctacatg    240
gaggtgagca agctgagatc tgacgacacg gccgtgtatt actgtgcgag acgatctgga    300
ggctcgggac gttattgggg aattaagaac aattggttcg acccctgggg ccagggcacc    360
ctggtcaccg tctcctca                                                  378
```

```
<210> SEQ ID NO 111
<211> LENGTH: 360
<212> TYPE: DNA
<213> ORGANISM: human
<220> FEATURE:
<223> OTHER INFORMATION: d10s5

<400> SEQUENCE: 111
ggtgacggtg gtgagtctgg ggctgaggtg aggaagcctg ggcctcagt gaaggtctcc     60 tgcaaggcct ctagatacag cttcaccgac tactttatgc actgggtgcg acaggcccct   120
ggacaagggc ttgagtggat gggatggatc aaccctaaca gtggtgtcac acactatgca   180
cagaagtttc agggcagggt caccatgacc agggacacgt ccatcaacac agcctacatg   240
gaagtgagca ggctgagata tgacgacacg gccgtgtatt actgtacgag agaactgata   300
gcaggtcgtc tgccaactga caacgactgg ggccagggaa ccctggtcac cgtctcctca   360
```

```
<210> SEQ ID NO 112
<211> LENGTH: 366
<212> TYPE: DNA
<213> ORGANISM: human
<220> FEATURE:
<223> OTHER INFORMATION: d10p1

<400> SEQUENCE: 112
caggtccagc tggtgcagtc tggggctgag gtgaagaagc ctggggcctc agtgaaggtc    60
tcctgtaagg ctgctggata caccttcacc gactactatt tcactgggt gcgacaggcc    120 cctggacaag gcttgagtg gatgggatgg atcaatcctg acagtggtgg aacaaactat    180
gcacagaagt tcagggcag gtcaccatg accagggaca cgtccatcag cacagcctac    240
atggacctga gcaggctgag atctgacgac acggccgtat gttactgtgc gagagggtcc    300
cgatataaca gtggctggta ttactttgac tactggagcc ggggaaccct ggtcaccgtc    360
tcctca                                                              366
```

```
<210> SEQ ID NO 113
<211> LENGTH: 360
<212> TYPE: DNA
<213> ORGANISM: human
<220> FEATURE:
<223> OTHER INFORMATION: d10p2

<400> SEQUENCE: 113
caggtgcagc tacaggagtg ggcccagga ctggtgaagc cttcggggac cctgtccctc     60
acctgcgctg tctctggtgg caccatcagc agtcctacct ggtggaattg ggtccgccag   120
ccccagggaa aggggctgga gtggattggc gaaatctatc atagtggaac ctcccaccac   180
aacccgtccc tcaagaatcg agtcaccta tcagtagaca agtccaagaa ccagttctcc    240
ctgaagctga actctatgac cgccgcggac acggccgtgt atttctgtac gagactggat   300
ttcgattccc cactcggtat ggacgcctgg ggccaaggga ccacggtcac cgtctcctca   360
```

<210> SEQ ID NO 114
<211> LENGTH: 327
<212> TYPE: DNA
<213> ORGANISM: human
<220> FEATURE:
<223> OTHER INFORMATION: dVL4

<400> SEQUENCE: 114

| | | | | | |
|---|---|---|---|---|---|
| gacatcgtga | tgacccggtc | tccatcctcc | ctgtctgcat | ctgtaggaga | cagagtcacc | 60 |
| atcacttgcc | gggcaagtca | gagcattagc | acctatttaa | attggtatca | gcagaaagca | 120 |
| gggaaagccc | ctaaactcct | gatctatgct | gcatccagtt | tgcaaagtgg | ggtcccctca | 180 |
| aggttcagtg | gcagtggatc | tgggacagat | ttcactctca | ccatcagcag | tctgcaacct | 240 |
| gaagattttg | caacttacta | ctgtcaacag | agttacagta | cccctcgaac | gttcggccaa | 300 |
| gggaccaagg | tggaaatcaa | acgtgcg | | | | 327 |

<210> SEQ ID NO 115
<211> LENGTH: 330
<212> TYPE: DNA
<213> ORGANISM: human
<220> FEATURE:
<223> OTHER INFORMATION: dVL7

<400> SEQUENCE: 115

| | | | | | |
|---|---|---|---|---|---|
| gaaattgtgt | tgacgcagtc | tccatcttct | gtgtctgcat | ctgtgggaga | cagagtcacc | 60 |
| atcacttgtc | gggcgagtga | ggatgttaac | agctggttag | cctggtatca | gcagaagcca | 120 |
| gggaaagccc | ctaagctcct | gatctatggt | tcaaccaatt | tgcaaggtgg | ggtcccatca | 180 |
| aggttcagcg | gacgtggatc | tgggacacac | tttactttca | ccatcaacgg | cctgcagcct | 240 |
| gaagatattg | caacatatta | ctgtaaatat | tttgatgctc | tccctccggt | caccttcggc | 300 |
| caagggacac | gactggagat | taaacgtgcg | | | | 330 |

<210> SEQ ID NO 116
<211> LENGTH: 345
<212> TYPE: DNA
<213> ORGANISM: human
<220> FEATURE:
<223> OTHER INFORMATION: dVL10

<400> SEQUENCE: 116

| | | | | | |
|---|---|---|---|---|---|
| gacatcgtgc | tgacccagtc | tccagactcc | ctggctgtgt | ctctgggcga | gagggccacc | 60 |
| atcaactgca | cgtccagcca | gagtctttta | tacacctcca | caataagaa | ctacttaact | 120 |
| tggtaccaac | agaaaccagg | gcagcctcct | aaactcctca | tttactgggc | atctacccgg | 180 |
| gaattcggcg | tccctgaccg | attcagtggc | agcgggtctg | ggacagattt | cactctcacc | 240 |
| atcaacagcc | tgcaggctga | agatgtggcg | acttattact | gtcagcaata | ttctgatcct | 300 |
| cctcccactt | tcggcggagg | gaccaagctg | gagatcaaac | gtgcg | | 345 |

<210> SEQ ID NO 117
<211> LENGTH: 79
<212> TYPE: DNA
<213> ORGANISM: artificial sequence
<220> FEATURE:
<223> OTHER INFORMATION: scFv-B
<220> FEATURE:
<221> NAME/KEY: misc_feature
<222> LOCATION: (1)..(5)
<223> OTHER INFORMATION: n is a, c, g, or t

<400> SEQUENCE: 117
nnnnnccatg gccgggggcg ggggcagcgg gggcggggc agcggggcg ggggcagcca    60 ggtgcagttg gtggagtct    79

<210> SEQ ID NO 118
<211> LENGTH: 31
<212> TYPE: DNA
<213> ORGANISM: artificial sequence
<220> FEATURE:
<223> OTHER INFORMATION: scFv-F
<220> FEATURE:
<221> NAME/KEY: misc_feature
<222> LOCATION: (1)..(5)
<223> OTHER INFORMATION: n is a, c, g, or t

<400> SEQUENCE: 118
nnnnnccgcg gaaccattca gatcctcttc t    31

<210> SEQ ID NO 119
<211> LENGTH: 32
<212> TYPE: DNA
<213> ORGANISM: artificial sequence
<220> FEATURE:
<223> OTHER INFORMATION: SiscFv-B
<220> FEATURE:
<221> NAME/KEY: misc_feature
<222> LOCATION: (1)..(5)
<223> OTHER INFORMATION: n is a, c, g, or t

<400> SEQUENCE: 119
nnnnnccatg gcccaggtgc agttggtgga gt    32

<210> SEQ ID NO 120
<211> LENGTH: 67
<212> TYPE: DNA
<213> ORGANISM: artificial sequence
<220> FEATURE:
<223> OTHER INFORMATION: SiscFv-F
<220> FEATURE:
<221> NAME/KEY: misc_feature
<222> LOCATION: (1)..(5)
<223> OTHER INFORMATION: n is a, c, g, or t

<400> SEQUENCE: 120
nnnnnccgcg gcacgtgggg gtgcttgtgg tgcacgtgca tggggataac cattcagatc    60
ctcttct    67

<210> SEQ ID NO 121
<211> LENGTH: 37
<212> TYPE: DNA
<213> ORGANISM: artificial sequence
<220> FEATURE:
<223> OTHER INFORMATION: gVH-B
<220> FEATURE:
<221> NAME/KEY: misc_feature
<222> LOCATION: (1)..(5)
<223> OTHER INFORMATION: n is a, c, g, or t

<400> SEQUENCE: 121
nnnnnccatg gccgaccagg tgcagttggt ggagtct    37

<210> SEQ ID NO 122
<211> LENGTH: 30
<212> TYPE: DNA
<213> ORGANISM: artificial sequence
<220> FEATURE:
<223> OTHER INFORMATION: gVH-Phe
<220> FEATURE:

-continued

```
<221> NAME/KEY: misc_feature
<222> LOCATION: (1)..(5)
<223> OTHER INFORMATION: n is a, c, g, or t

<400> SEQUENCE: 122
nnnnncggcc gtgacggtga ccagggtgcc                                      30

<210> SEQ ID NO 123
<211> LENGTH: 47
<212> TYPE: DNA
<213> ORGANISM: artificial sequence
<220> FEATURE:
<223> OTHER INFORMATION: gVL-B
<220> FEATURE:
<221> NAME/KEY: misc_feature
<222> LOCATION: (1)..(5)
<223> OTHER INFORMATION: n is a, c, g, or t

<400> SEQUENCE: 123
nnnnngctag cggtggcggt ggctctgaaa ttgtgttgac gcagtct                   47

<210> SEQ ID NO 124
<211> LENGTH: 33
<212> TYPE: DNA
<213> ORGANISM: artificial sequence
<220> FEATURE:
<223> OTHER INFORMATION: gVL-Phe
<220> FEATURE:
<221> NAME/KEY: misc_feature
<222> LOCATION: (1)..(5)
<223> OTHER INFORMATION: n is a, c, g, or t

<400> SEQUENCE: 124
nnnnnccgcg gcacgtttaa tctccagtcg tgt                                  33

<210> SEQ ID NO 125
<211> LENGTH: 112
<212> TYPE: PRT
<213> ORGANISM: chicken

<400> SEQUENCE: 125

Asp Val Gln Leu Gln Glu Ser Gly Pro Ser Leu Val Lys Pro Ser Gln
1               5                   10                  15

Thr Leu Ser Leu Thr Cys Ser Val Thr Gly Asp Ser Thr Thr Ser Asp
                20                  25                  30

Tyr Trp Ser Trp Ile Arg Lys Phe Pro Gly Asn Arg Leu Glu Tyr Met
            35                  40                  45

Gly Tyr Val Ser Tyr Ser Gly Ser Thr Tyr Tyr Asn Pro Ser Leu Lys
        50                  55                  60

Ser Arg Ile Ser Ile Thr Arg Asp Thr Ser Lys Asn Gln Tyr Tyr Leu
65                  70                  75                  80

Asp Leu Asn Ser Val Thr Thr Glu Asp Thr Ala Thr Tyr Tyr Cys Ala
                85                  90                  95

Asn Trp Asp Gly Asp Tyr Trp Gly Gln Gly Thr Leu Val Thr Val Ser
            100                 105                 110

<210> SEQ ID NO 126
<211> LENGTH: 42
<212> TYPE: DNA
<213> ORGANISM: artificial sequence
<220> FEATURE:
<223> OTHER INFORMATION: hVH-B
<220> FEATURE:
<221> NAME/KEY: misc_feature
<222> LOCATION: (1)..(5)
```

```
<223> OTHER INFORMATION: n is a, c, g, or t

<400> SEQUENCE: 126
nnnnnccatg gccgacgata tccagctgca ggagtcgggc cc          42

<210> SEQ ID NO 127
<211> LENGTH: 29
<212> TYPE: DNA
<213> ORGANISM: artificial sequence
<220> FEATURE:
<223> OTHER INFORMATION: hVH-Phe
<220> FEATURE:
<221> NAME/KEY: misc_feature
<222> LOCATION: (1)..(5)
<223> OTHER INFORMATION: n is a, c, g, or t

<400> SEQUENCE: 127
nnnnngctag cggagacggt gacgtctgt                         29

<210> SEQ ID NO 128
<211> LENGTH: 108
<212> TYPE: PRT
<213> ORGANISM: chiken

<400> SEQUENCE: 128
```

Asp Ile Val Leu Thr Gln Ser Pro Ala Thr Leu Ser Val Thr Pro Gly
1               5                   10                  15

Asn Ser Val Ser Leu Ser Cys Arg Ala Ser Gln Ser Ile Gly Asn Asn
            20                  25                  30

Leu His Trp Tyr Gln Gln Lys Ser His Glu Ser Pro Arg Leu Leu Thr
        35                  40                  45

Lys Tyr Ala Ser Gln Ser Ile Ser Gly Thr Pro Ser Arg Phe Ser Gly
    50                  55                  60

Ser Gly Ser Gly Thr Asp Phe Thr Leu Ser Ile Asn Ser Val Glu Thr
65                  70                  75                  80

Glu Asp Phe Gly Met Tyr Phe Cys Gln Gln Ser Asn Ser Trp Pro Tyr
                85                  90                  95

Thr Phe Gly Gly Gly Thr Lys Leu Glu Ile Thr Ala
            100                 105

```
<210> SEQ ID NO 129
<211> LENGTH: 46
<212> TYPE: DNA
<213> ORGANISM: artificial sequence
<220> FEATURE:
<223> OTHER INFORMATION: hVL-B
<220> FEATURE:
<221> NAME/KEY: misc_feature
<222> LOCATION: (1)..(5)
<223> OTHER INFORMATION: n is a, c, g, or t

<400> SEQUENCE: 129
nnnnngctag cggtggcggt ggctctgata tcgtcctgac ccagag      46

<210> SEQ ID NO 130
<211> LENGTH: 32
<212> TYPE: DNA
<213> ORGANISM: artificial sequence
<220> FEATURE:
<223> OTHER INFORMATION: hVL-Phe
<220> FEATURE:
<221> NAME/KEY: misc_feature
<222> LOCATION: (1)..(5)
<223> OTHER INFORMATION: n is a, c, g, or t
```

<400> SEQUENCE: 130
nnnnnccgcg gccttgatct ccagcttggt gc                          32

<210> SEQ ID NO 131
<211> LENGTH: 32
<212> TYPE: DNA
<213> ORGANISM: artificial sequence
<220> FEATURE:
<223> OTHER INFORMATION: NheI-VHh_f
<220> FEATURE:
<221> NAME/KEY: misc_feature
<222> LOCATION: (1)..(5)
<223> OTHER INFORMATION: n is a, c, g, or t

<400> SEQUENCE: 131
nnnnngctag ccaggtgcag ttggtggagt ct                          32

<210> SEQ ID NO 132
<211> LENGTH: 35
<212> TYPE: DNA
<213> ORGANISM: artificial sequence
<220> FEATURE:
<223> OTHER INFORMATION: VHh-SacII_r
<220> FEATURE:
<221> NAME/KEY: misc_feature
<222> LOCATION: (1)..(5)
<223> OTHER INFORMATION: n is a, c, g, or t

<400> SEQUENCE: 132 nnnnnccgc ggatgaggag acggtgacca gggtt                        35

<210> SEQ ID NO 133
<211> LENGTH: 32
<212> TYPE: DNA
<213> ORGANISM: artificial sequence
<220> FEATURE:
<223> OTHER INFORMATION: 7s4-fw-EcoR1s

<400> SEQUENCE: 133
aagctgaatt ccaggtgcag ttggtggagt ct                          32

<210> SEQ ID NO 134
<211> LENGTH: 27
<212> TYPE: DNA
<213> ORGANISM: artificial sequence
<220> FEATURE:
<223> OTHER INFORMATION: HELVH-SacII-r
<220> FEATURE:
<221> NAME/KEY: misc_feature
<222> LOCATION: (1)..(5)
<223> OTHER INFORMATION: n is a, c, g, or t

<400> SEQUENCE: 134
nnnnnccgcg gagacggtga cgagggt                                27

<210> SEQ ID NO 135
<211> LENGTH: 357
<212> TYPE: DNA
<213> ORGANISM: artificial sequence
<220> FEATURE:
<223> OTHER INFORMATION: FER-7s4 coding DNA

<400> SEQUENCE: 135
caggtgcagt tggtggagtc tggagcagag gtgaaaaagg ccggggagtc tctgaagatc    60
tcctgtaagg gatctggata cagctttccc agttactgga tcaactggtt ccgccagatg   120
cccggcaaag aaagggaatg gatggggatg atctatcctg ctgactctga taccagatat   180

```
agcccgtcct tccaaggcca cgtcaccatc tcagccgaca gtccatcaa caccgcctac      240 ctgcaatggg ccggcctgaa ggcctcggac accgccatat attactgtgc gagacttgga      300
attggtggga ggtacatgtc tagatggggc cagggaaccc tggtcaccgt ctcctca         357

<210> SEQ ID NO 136
<211> LENGTH: 119
<212> TYPE: PRT
<213> ORGANISM: recombinant protein
<220> FEATURE:
<223> OTHER INFORMATION: FER-7s4

<400> SEQUENCE: 136

Gln Val Gln Leu Val Glu Ser Gly Ala Glu Val Lys Lys Ala Gly Glu
1               5                   10                  15

Ser Leu Lys Ile Ser Cys Lys Gly Ser Gly Tyr Ser Phe Pro Ser Tyr
                20                  25                  30

Trp Ile Asn Trp Phe Arg Gln Met Pro Gly Lys Glu Arg Glu Trp Met
            35                  40                  45

Gly Met Ile Tyr Pro Ala Asp Ser Asp Thr Arg Tyr Ser Pro Ser Phe
    50                  55                  60

Gln Gly His Val Thr Ile Ser Ala Asp Lys Ser Ile Asn Thr Ala Tyr
65                  70                  75                  80

Leu Gln Trp Ala Gly Leu Lys Ala Ser Asp Thr Ala Ile Tyr Tyr Cys
                85                  90                  95

Ala Arg Leu Gly Ile Gly Gly Arg Tyr Met Ser Arg Trp Gly Gln Gly
            100                 105                 110

Thr Leu Val Thr Val Ser Ser
        115

<210> SEQ ID NO 137
<211> LENGTH: 33
<212> TYPE: DNA
<213> ORGANISM: artificial sequence
<220> FEATURE:
<223> OTHER INFORMATION: V37F-f

<400> SEQUENCE: 137
ttactggatc aactggttcc gccagatgcc cgg                                    33

<210> SEQ ID NO 138
<211> LENGTH: 33
<212> TYPE: DNA
<213> ORGANISM: artificial sequence
<220> FEATURE:
<223> OTHER INFORMATION: V37F-r

<400> SEQUENCE: 138
ccgggcatct ggcggaacca gttgatccag taa                                    33

<210> SEQ ID NO 139
<211> LENGTH: 33
<212> TYPE: DNA
<213> ORGANISM: artificial sequence
<220> FEATURE:
<223> OTHER INFORMATION: G44E-f

<400> SEQUENCE: 139
cagatgcccg gcaaagaact ggaatggatg ggg                                    33

<210> SEQ ID NO 140
```

-continued

```
<211> LENGTH: 33
<212> TYPE: DNA
<213> ORGANISM: artificial sequence
<220> FEATURE:
<223> OTHER INFORMATION: G44E-r

<400> SEQUENCE: 140
ccccatccat tccagttctt tgccgggcat ctg                                    33

<210> SEQ ID NO 141
<211> LENGTH: 31
<212> TYPE: DNA
<213> ORGANISM: artificial sequence
<220> FEATURE:
<223> OTHER INFORMATION: 45F-f

<400> SEQUENCE: 141
gcccggcaaa gaaagggaat ggatggggat g                                      31

<210> SEQ ID NO 142
<211> LENGTH: 31
<212> TYPE: DNA
<213> ORGANISM: artificial sequence
<220> FEATURE:
<223> OTHER INFORMATION: 45F-r

<400> SEQUENCE: 142
catccccatc cattcccttt ctttgccggg c                                      31

<210> SEQ ID NO 143
<211> LENGTH: 708
<212> TYPE: DNA
<213> ORGANISM: artificial sequence
<220> FEATURE:
<223> OTHER INFORMATION: HEL binding single chain-Fv coding DNA

<400> SEQUENCE: 143
gatatcgtcc tgacccagag cccggcgacc ctctcggtca cccccggcaa ctcggtgtcc        60
ctctcgtgcc gcgcctcgca gtcgatcggc aacaacctcc actggtatca gcagaagtcg       120
cacgagagcc cgcgcctcct gatcaagtac gccagccagt cgatctcggg gatcccgtcg       180
cgcttcagcg gctcgggctc gggcaccgac ttcaccctgt cgatcaacag cgtcgagacg       240
gaggacttcg gcatgtactt ctgccagcag tcgaacagct ggccgtacac cttcggcggc       300
ggtaccaagc tgatcatcac ggccggcggg ggcggtagcg gcggtggcgg gtcgggcggt       360
ggcggatcgg atatccagct gcaggagtcg ggcccgagcc tcgtcaagcc gtcgcagacc       420
ctgtcgctca cctgcagcgt caccggcgac tcgatcacct cggactactg gtcgtggatc       480
cgcaagttcc ccggcaaccg cctcgagtac atgggctacg tcagctactc gggcagcacc       540
tactacaacc cctcgctgaa gagccgcatc tcgatcaccc gcgacacctc caagaaccag       600
tactacctgg acctcaactc ggtcaccacc gaggacaccc ccacctacta ctgcgcgaac       660
tgggacggcg actactgggg ccagggcacc ctcgtcaccg tctccgcg                    708

<210> SEQ ID NO 144
<211> LENGTH: 236
<212> TYPE: PRT
<213> ORGANISM: recombinant protein
<220> FEATURE:
<223> OTHER INFORMATION: HEL binding single chain-Fv coding DNA

<400> SEQUENCE: 144

Asp Ile Val Leu Thr Gln Ser Pro Ala Thr Leu Ser Val Thr Pro Gly
```

```
                1               5                   10                  15
Asn Ser Val Ser Leu Ser Cys Arg Ala Ser Gln Ser Ile Gly Asn Asn
                        20                  25                  30

Leu His Trp Tyr Gln Gln Lys Ser His Glu Ser Pro Arg Leu Leu Ile
                35                  40                      45

Lys Tyr Ala Ser Gln Ser Ile Ser Gly Ile Pro Ser Arg Phe Ser Gly
            50                  55                  60

Ser Gly Ser Gly Thr Asp Phe Thr Leu Ser Ile Asn Ser Val Glu Thr
65                      70                  75                  80

Glu Asp Phe Gly Met Tyr Phe Cys Gln Gln Ser Asn Ser Trp Pro Tyr
                        85                  90                  95

Thr Phe Gly Gly Gly Thr Lys Leu Ile Ile Thr Ala Gly Gly Gly Gly
                    100                 105                 110

Ser Gly Gly Gly Gly Ser Gly Gly Gly Ser Asp Ile Gln Leu Gln
                115                 120                 125

Glu Ser Gly Pro Ser Leu Val Lys Pro Ser Gln Thr Leu Ser Leu Thr
            130                 135                     140

Cys Ser Val Thr Gly Asp Ser Ile Thr Ser Asp Tyr Trp Ser Trp Ile
145                 150                 155                 160

Arg Lys Phe Pro Gly Asn Arg Leu Glu Tyr Met Gly Tyr Val Ser Tyr
                    165                 170                 175

Ser Gly Ser Thr Tyr Tyr Asn Pro Ser Leu Lys Ser Arg Ile Ser Ile
                180                 185                 190

Thr Arg Asp Thr Ser Lys Asn Gln Tyr Tyr Leu Asp Leu Asn Ser Val
                    195                 200                 205

Thr Thr Glu Asp Thr Ala Thr Tyr Tyr Cys Ala Asn Trp Asp Gly Asp
                210                 215                 220

Tyr Trp Gly Gln Gly Thr Leu Val Thr Val Ser Ala
225                     230                 235

<210> SEQ ID NO 145
<211> LENGTH: 30
<212> TYPE: DNA
<213> ORGANISM: artificial sequence
<220> FEATURE:
<223> OTHER INFORMATION: scFv-f
<220> FEATURE:
<221> NAME/KEY: misc_feature
<222> LOCATION: (1)..(4)
<223> OTHER INFORMATION: n is a, c, g, or t

<400> SEQUENCE: 145
nnnnccatgc cgatatcgt cctgacccag                                     30

<210> SEQ ID NO 146
<211> LENGTH: 27
<212> TYPE: DNA
<213> ORGANISM: artificial sequence
<220> FEATURE:
<223> OTHER INFORMATION: scFv-f

<400> SEQUENCE: 146
agctaccgcg gagacggtga cgagggt                                       27

<210> SEQ ID NO 147
<211> LENGTH: 35
<212> TYPE: DNA
<213> ORGANISM: artificial sequence
<220> FEATURE:
<223> OTHER INFORMATION: A14P-f
```

<400> SEQUENCE: 147
gagcagaggt gaaaaagcca ggggagtctc tgaag         35

<210> SEQ ID NO 148
<211> LENGTH: 35
<212> TYPE: DNA
<213> ORGANISM: artificial sequence
<220> FEATURE:
<223> OTHER INFORMATION: A14P-r

<400> SEQUENCE: 148
cttcagagac tcccctggct ttttcacctc tgctc         35

<210> SEQ ID NO 149
<211> LENGTH: 47
<212> TYPE: DNA
<213> ORGANISM: artificial sequence
<220> FEATURE:
<223> OTHER INFORMATION: VHg-f
<220> FEATURE:
<221> NAME/KEY: misc_feature
<222> LOCATION: (1)..(5)
<223> OTHER INFORMATION: n is a, c, g, or t

<400> SEQUENCE: 149
nnnnngctag cggcggggc ggtagccagg tgcagttggt ggagtct         47

<210> SEQ ID NO 150
<211> LENGTH: 34
<212> TYPE: DNA
<213> ORGANISM: artificial sequence
<220> FEATURE:
<223> OTHER INFORMATION: VHg-r
<220> FEATURE:
<221> NAME/KEY: misc_feature
<222> LOCATION: (1)..(5)
<223> OTHER INFORMATION: n is a, c, g, or t

<400> SEQUENCE: 150
nnnnnccgcg gatgaggaga cggtgaccag ggtt         34

<210> SEQ ID NO 151
<211> LENGTH: 38
<212> TYPE: DNA
<213> ORGANISM: artificial sequence
<220> FEATURE:
<223> OTHER INFORMATION: VHg4-f
<220> FEATURE:
<221> NAME/KEY: misc_feature
<222> LOCATION: (1)..(5)
<223> OTHER INFORMATION: n is a, c, g, or t

<400> SEQUENCE: 151
nnnnngctag cggcagccag gtgcagttgg tggagtct         38

<210> SEQ ID NO 152
<211> LENGTH: 34
<212> TYPE: DNA
<213> ORGANISM: artificial sequence
<220> FEATURE:
<223> OTHER INFORMATION: VHg4-r
<220> FEATURE:
<221> NAME/KEY: misc_feature -continued

```
<222> LOCATION: (1)..(5)
<223> OTHER INFORMATION: n is a, c, g, or t

<400> SEQUENCE: 152
nnnnnccgcg gatgaggaga cggtgaccag ggtt                                    34
```

GOLD-BINDING PROTEIN AND USE THEREOF

TECHNICAL FIELD

The present invention relates to a gold-binding protein, a complex protein containing the gold-binding protein, and uses thereof for detecting their target substances.

BACKGROUND ART

Semiconductor industry has been developed markedly by miniaturizing devices with an improvement in recent semiconductor microprocessing technology. The microprocessing technology typified by lithography has recently achieved an accuracy of finishing of several hundred nanometers. Materials and devices applied with the above technology can participate actively in many scenes and have been expected to be applied in a wide variety of fields of optical communication, electric communication, and so on as well as of biotechnology and energy. However, when consideration is given to processing on the scale of 100 nanometers or less as an extension of current microprocessing technology, there remain many challenges for industrial use including the time and expense involved in processing in addition to technical challenges. With a growing number of applicable fields, novel technology of manufacturing refined structures as an alternative to the above has been strongly demanded.

Under the circumstances, research and development have been actively conducted on novel materials by means of a bottom-up approach that produces desired structures and properties controlled at the atomic or molecular level, instead of conventional top-down processing technology. An example of bottom-up technology of producing refined structures includes the development of a molecular device in which a molecular arrangement is controlled on a metal surface, and the use of methods of utilizing the self-assembly of substances has been studied as one of such technologies of molecular arrangement control. As a recent example of the study, Lindsay et al., (Science, 300: p. 1413, 2003) has examined a molecular switching function by the use of a self-assembled monolayer where alkanethiol and alkanedithiol having thiol groups at their respective molecular ends are oriented on a gold substrate.

It has been known that biomolecules typified by nucleic acids and proteins are constructed as precise structures under control at the atomic level for exerting their functions. The uses of the properties of such biomolecules have been also under investigation to apply the biomolecules to a variety of devices in which the biomolecules are arranged on a substrate of metal, metal oxide, or semiconductor. Technology of producing a fine structure where the biomolecule is arranged on a substrate becomes important for a first step of developing such devices. For example, when consideration is given to the immobilization of a deoxyribonucleic acid (DNA) on a gold substrate or the immobilization of a peptide having an amino acid sequence with various functions thereon, it has been widely known that the DNA or the peptide can be chemically synthesized and the ends of these substances are chemically modified with thiol groups (—SH) to thereby coordinate these substances on a gold substrate with the use of S—Au surface absorption. Using this fact, study has been conducted on experimental systems and conversion into devices in which DNA or peptide is immobilized on gold.

On the other hand, proteins that function as enzymes, antibodies, or the like have high molecular weights. Thus, it is very difficult to chemically synthesize such compounds having high molecular weights to form higher order structures while keeping abilities to exert their functions. Although a variety of studies have been currently conducted, the situation is that functional proteins that combine their higher order structures with desired functions have not been synthesized yet in most cases (Science, 302: p. 1364, 2003). When the functional protein is immobilized on a substrate material, binding with the substrate is generally performed by treating the substrate with a variety of surface treatment agents typified by a silane coupling agent, and introducing into the protein a functional group capable of binding to the surface of the substrate that was subjected to surface treatment (Proteomics, 3: p. 254, 2003). However, it has been pointed out that such introduction of a reactive functional group into the functional protein is generally performed by chemical modification and an introduction site is nonselectively determined. Therefore, the functional protein is immobilized in a less functionable shape on the substrate and may be reduced in the resulting activity due to the modification of the functional expression site of the functional protein.

It is also possible to introduce a binding site into a protein by a genetic engineering procedure to produce a fusion protein. As an example, there is known a method in which all sites or the biotin-binding site of (strept) avidin which is known to bind to a low molecular compound, biotine, is introduced into the N- or C-terminal of a desired protein by genetic engineering and the desired protein is then expressed as a fusion protein that is in turn immobilized via biotin arranged on the surface of a desired substrate.

Furthermore, another technique has been recently disclosed. In this case, a peptide composed of five or more amino acids capable of binding to a substrate material for immobilization. The peptide may be fused to a desired protein to produce a fusion protein, thereby binding and immobilizing the desired protein on the substrate. Belcher et al., has disclosed a peptide composed of 12 amino acids capable of specifically recognizing a certain crystal surface containing GaAs by the phage display method (Nature, 405: p. 665, 2000), creating the new possibilities for studying devices with the use of the ability of biomaterials to self-assemble. Moreover, Belcher et al., discloses the amino acid sequence of a peptide composed of 7 to 14 amino acids for other semiconductors (PbS, CdS) (WO 03/029431). Brown et al., discloses some examples of a peptide with a repetitive structure having the unit of an amino acid sequence composed of 14 residues, showing affinity for gold (Nature Biotechnology, 15: p. 269, 1997). Heretofore, a number of other peptides having affinity for metals (Au, Pt, Pd, Ag), metal oxides ($SiO_2$, ZnO, $Cr_2O_3$, $Fe_2O_3$), or semiconductors have been obtained by the above-described phage display method.

By immobilizing a desired biomolecule on a substrate via such a peptide having affinity for the substrate material, a structure cyclically having a desired function and shape can be also constructed in a self-assembly manner due to the interaction between biomolecules or with a different substance. For example, Belcher et al., discloses technique in which M13 phage displaying ZnS-affinity peptide bound with ZnS particles is coordinated by self-assembly to thereby produce a liquid crystal-like film (Science, 296: 892, 2002).

In addition, some examples show a desired functional protein to which a substrate-binding site is fused is produced by genetic engineering as described above to thereby allow the functional protein to be immobilized at a desired site other than the functional site on the substrate. However, when peptide having affinity for a substrate material is lined to the end of a functional protein directly or via a linker composed of a few amino acids and then bound to a solid phase (e.g., substrate) to achieve the immobilization of the protein, the active site of the functional protein (e.g., several amino acid residues constituting the antigen-binding site of an antibody) is close to the substrate and undergoes some interaction (e.g., electrostatic effect) from the surface of the substrate to cause structural changes and the like, resulting in a fear of incapable of sufficiently exerting a desired function. Even when a linker is designed to be still longer, peptide as the linker, which has a high degree of freedom in the motion of the molecules, may be arranged close to a functional site and its function may be inhibited.

From the above problems, the inventors of the present invention have arrived at the idea that a substrate-binding site on which functional polymeric materials including a functional protein linker are immobilized needs to have a structural portion (scaffold) given as a spacer that keeps a certain distance from a substrate without inhibiting desired activity of an immobilized protein, and a site that binds to the substrate.

As a molecule-recognizing molecule having such a scaffold, the most well known is antibody. The antibody is one of the proteins functioning in a self defense mechanism to specifically recognize and bind to a variety of structures on the surface of a foreign substance invading animals body fluid that is subsequently detoxicated by the immune system. The diversity of antibodies (the number of antibodies having different amino acid sequences for binding to a variety of foreign substances) is estimated to be $10^7$ to $10^8$ different varieties per animal. The structure is formed of polypeptide chains having two longer chains and two shorter chains and the longer polypeptide chain (heavy chain) and the shorter polypeptide chain (light chain) are referred to as a heavy chain and a light chain, respectively.

Those heavy and light chains each have a variable region and a constant region. The light chain is a polypeptide chain composed of two domains of one variable region (VL) and one constant region (CL), while the heavy chain is a polypeptide chain composed of four domains of one variable region (VH) and three constant regions (CH1-CH3). Each of the above-described domains assumes a cylindrical structure composed of approximately 110 amino acids, and forms the layer structure of β sheets antiparallely arranged, and this layer structure is bound with one SS bond to form a highly stable structure. Moreover, it is known that the binding of the antibody to a variety of antigen species results from the diversity of amino acid sequences in three complementarity determining regions (CDF) of each of the above-described variable regions (VH or VL). The CDRs, three for VH and three for VL, are separately arranged by framework regions and recognizes the spatial configuration of functional groups in a recognition site of interest to allow highly specific molecular recognition.

The diversity of the above-described CDR is attributed to DNA rearrangement that takes place in the antibody locus when a myeloid stem cell is differentiated into a B lymphocyte as an antibody-producing cell. It is known that a portion composed of VH, D, and JH gene fragments in the heavy chain, and a portion composed of Vλ or Vκ and Jλ or Jκ gene fragments in the light chain undergo DNA rearrangement to thereby produce antibodies. Such DNA rearrangement independently takes place in each B cell, one B cell produces only one kind of antibody. However, the whole B cells in an individual can produce diverse antibodies.

Antibody capable of binding to a specific substance as described above has been artificially produced heretofore using an antibody-forming mechanism in the immune system of an animal, and utilized in a variety of industrial fields. An example of production methods is a method in which an animal to be immunized (e.g., rabbit, goat, or mouse) is immunized at constant intervals with an antigenic substance of interest along with an adjuvant, and antibodies present in its serum are collected. The antibodies obtained as above are a mixture of several antibodies recognizing a variety of structures in the surface of the antigenic substance used in the immunization. Serum containing several antibodies binding to one antigen is referred to as a polyclonal antibody.

On the other hand, a variety of B lymphocytes that produce antibodies binding to an antigen of interest are present in the spleen of an animal to be immunized. Such an antibody-forming B lymphocyte is fused to an established tumor cell to thereby allow the production of a hybridoma cell. As described above, one B lymphocyte produces one kind of antibody, and a system that can subculture the B lymphocyte producing one kind of antibody as a hybridoma has been established. The antibody produced as above is referred to as a monoclonal antibody.

As a molecular recognition structure using the above-described structure of the antibody as an anchorage, JP 05-055534 A discloses a multibinding antibody recognizing two different antigens and a method of forming a multilayer using the same. According to this technique, a fusion antibody recognizing a first antigen and a second antigen can be obtained. In addition, the first antigen, the fusion antigen, and the second antigen are successively arranged on the surface of a substrate to thereby allow the formation of a multilayer without chemical modification. However, for obtaining the disclosed fusion protein, it is necessary to use an animal cell, turning into a problem in terms of cost efficiency and operational complication. Besides, when the multilayer is formed, a step of arranging an antibody recognizable by the fusion protein on the surface of the substrate must be provided.

An antibody fragment, Fab, Fab', or $F(ab')_2$, obtained by treating the above-described antibody with a certain proteolytic enzyme, is known to have the ability to bind to an antigen similar to that of the parent antibody.

Likewise, for the above-described VH, VL, or Fv as a complex thereof, or even for a complex composed of the VH or the VL, single chain Fv (scFv) having the carboxy terminal of one region and the amino terminal of another region linked via peptide composed of several amino acids, or the like, is known to have the ability to bind to an antigen similar to that of the parent antibody.

Skerra and Better disclose a method in which Fab-type and Fv-type antibody fragments, the N terminals of which are added with a secretion signal sequence by a genetic engineering method, are produced as the expression of antibody genes by *E. coli* (Science, 240: P. 1038, 1988; Science, 240: p. 1041, 1988). Alternatively, JP 07-501451 A discloses a multivalent antigen-binding antibody and a method of producing the same, and JP 08-504100 A discloses a multivalent and multi-binding antibody and a method of producing the same. Those two techniques disclose that a binding protein is a protein containing an antibody variable region portion (VH and/or VL) binding to one or more antigens. JP 07-501451 discloses the structures and amino acid sequences of binding proteins each recognizing pancarcinoma antigen TAG-72 and fluorescein and a bispecific antibody recognizing both, as well as base sequences encoding them. JP 08-504100 A discloses, in Examples, a divalent and bispecific binding protein composed of an antibody fragment complex for known proteins (cell membrane protein, cancer antigen CEA, FcRγ1, etc.,) or low molecular compounds.

However, in the above-described disclosures, no technique concerning a binding protein that directly recognizes and binds to the surface of a substrate material typified by an inorganic substance is disclosed. Therefore, when a structure in which the binding protein is arranged on the substrate is produced, the arrangement must be performed by a conventionally known method, for example, a method involving chemically modifying the substrate or the above-described binding protein to arrange the binding protein on the substrate through a covalent bond. Similarly, when the binding protein is bound to a fine particle of a metal or a semiconductor substance, it is also necessary to chemically modify the particle to be bound or binding protein. Such chemical modification often targets amino residues or carboxyl groups contained in large numbers in the molecule of a protein, and a site involved in the reaction is nonselective. Therefore, a site exerting desired activity may be a substrate-binding or labeling site and, as a result, the desired activity of the protein may be reduced. Moreover, such a problem is likely to arise in not only the technique of conversion into microdevices but the production of sensing elements such as biosensors. Thus, it is important to immobilize a molecule capturing a target substance such as an antibody on a substrate while molecular orientation that sufficiently exerts its capturing function is maintained.

Studies are being conducted, in which a protein having a scaffold similar to that of the above-described antibody is added with the ability to recognize diverse molecules. Examples thereof include anticolin (Review in Molecular Biotechnology, 74: p. 257, 2001) and a fibronectin type III domain (J. Mol. Biol, 284: p. 1141, 1998). Anticolin is a capture protein altered on the basis of lipocalin. Lipocalin is a protein composed of 160 to 180 amino residues, which functions in transporting and storing substances with a low degree of solubility in water. Regarding constitution, lipocalin is a barrel structure composed of 8 β sheets. Lipocalin can recognize and bind to a substance of interest through 4 loop structures connecting the 8 β sheets. Fibronectin is generally a protein composed of amino acids not more than 100 residues, which plays a key role in the junction of cells with extracellular matrix or cell junction. Like the two proteins described above, fibronectin is a protein that has β sheet structures and recognizes a target substance through loop structures among the β sheets. A novel binding protein has been constructed by introducing random amino acid sequences into the loop structures among the β sheets of anticolin or fibronectin described above. Because those molecules have a strong molecular structure composed of β sheets in addition to a molecular recognition site, the molecules specifically recognize and bind to a substrate by the fusion to a desired functional polymeric material to thereby allow the polymeric material to be immobilized on the substrate. Moreover, the molecules are also expected to have a spacer function that keeps a certain distance from the substrate without inhibiting the desired activity of the immobilized polymeric material. However, there has been no reported case that molecule-recognizing proteins with constitutively stable scaffolds typified by the above-described antibody specifically recognize and bind to inorganic substances typified by metals or semiconductor materials.

On the other hand, in the field of detection of a variety of substances (target substances), several methods of the detection and/or quantification and the like of the target substances have been established so far, particularly for proteins such as antigens and antibodies, and sugar, lectin, and nucleic acids. For example, it is known that a labeling agent is bound to an antibody specifically recognizing and binding to a sugar or a lectin as target substances to thereby allow the detection or quantification of the target substance via the labeling agent. In general, a fine particle composed of a metal such as gold or an organic material such as latex, a fluorescent substance emitting fluorescence by excitation light in a certain wavelength region, or an enzyme having the fluorescent substance as a reaction product (e.g., HRP) is used as a labeling agent. Methods of labeling proteins such as antibodies include a method by physical absorption and a chemical bond method in which a reactive functional group is introduced into a labeling agent or a substance to be labeled and is used as a crosslinking point to form a chemical bond.

Hereinafter, prior arts will be described by taking antibodies used in detection as an example. JP 03-108115 B discloses an example of a method of labeling an antibody with gold by physically absorbing a gold fine particle onto the antibody. According to this method, a monoclonal antibody is added to a dispersion of gold colloid that has been previously adjusted, and the whole is subjected to centrifugal sedimentation to remove a supernatant liquid, and the resulting solution undergoes washing processes several times to allow the production of an antibody labeled with gold.

Next, a method of labeling antibodies by a chemical bond method will be described. Antibodies have the amino groups or SH groups of proteins. A functional group reactive with those groups is previously provided in a labeling agent to thereby allow the chemical bond between a labeling agent such as a fluorescent substance and a substance to be labeled such as an antibody. An example of the method includes a method involving introducing a labeling agent having an N-hydroxysuccinimide group, an isothiocyanate group, a nitroaryl halide group, or an acid chloride group, which reacts with an amino group. N-hydroxysuccininide that is widely used as a crosslinking agent for labeling proteins is known to efficiently react with an amino group under a pH atmosphere of 7 or more and form a highly stable amide bond (Biochemistry, Vol. 11, pp. 2291, 1972). The amino groups of the α position and of the ε position of lysine side chain on a protein can be targeted by a succinimide group in reaction. In particular, an amino group at the ε position is considered to be the general target of succinimide. For example, when a gold fine particle as a labeling agent is chemically bound to a protein such as an antibody, the gold fine particle is first modified with a compound having at least a SH group at one end and a functional group highly reactive with the above-described side chain residue of a protein at another end. Next, the protein can be crosslinked with the reactive functional group to bind them. However, because a residue having lysine or a free α-amino group nonselectively becomes a subject of interest in reaction in those methods, a protein to be labeled such as an antibody may be inhibited in its function. Although FITC is also known as a fluorescent substance having an isothiocyanate group, like succinimide, the desired property of a protein to be labeled may be reduced due to nonspecific reaction to an amino group.

Alternatively, a —SH group can be given as a crosslinking point. Methods with the use of a SH group can be broadly divided into a maleimide method and a pyridyl disulfide method. The maleimide method is a method with the use of a crosslinking agent having maleimide as a group selectively reactive with a SH group, which is known to allow selective crosslinkage under a mild condition. For example, when a subject to be bound is an antibody, a SH group that cleaved disulfide in the hinge portion of the antibody molecule is unrelated to the antigen-recognizing portion, so that the specificity of the antibody is expected not to be impaired even though the SH group is modified. This SH group is used as a crosslinking point to thereby allow the binding of a labeling agent without impairing a desired function. However, an antibody has 16 SS bonds within the whole molecule, including SS bonds for retaining the structures of a heavy chain variable region (VH) and a light chain variable region (VL) having a complementarity determining region (CDR) as the antigen-recognizing portion. Thus its function may be impaired if the reduction of the SS bond is not site-specifically performed.

JP 04-070320 B discloses a protein-labeling technique with the use of metallothionein or a fragment thereof, which is a low-molecular-weight protein capable of chelation with high affinity for a wide variety of metal ions. In this application, a technique is disclosed, in which metallothionein binds at the sulfhydryl moiety to a metal ion as a labeling agent and is bound to an antibody or the like at the other functional group given as a crosslinking point such as an amine group, a hydroxyl group, or a carboxyl group. Although sites binding to a metal ion and to a substance to be labeled are distinguished in metallothionein and can be bound with the respective substances to be bound, the binding site of the substance to be labeled is uncertain as in other crosslinking methods and problems as described above is likely to still remain.

Furthermore, means of resolving nonselective modification due to the immobilization method on a labeling agent through chemical crosslinking as described above includes a modification method by genetic engineering. It is also possible to produce a fusion protein in which a binding site is introduced into a protein by a genetic engineering approach. Known as an example is a method in which a low molecular compound biotin is chemically introduced into the end of a labeling agent such as a fluorescent substance, and the whole (strept) avidin known to bind to the above-described biotin or a biotin-binding site is introduced into the N terminal or C terminal of a desired protein by genetic engineering, which is in turn expressed as a fusion protein and bound to the labeling agent via the biotin-avidin bond. Thus, a low molecular compound is introduced into a labeling agent such as a fluorescent substance and a fusion protein in which a protein capable recognizing and binding to the low molecular compound is introduced into a desired protein is produced by genetic engineering to allow the introduction of a selective binding site.

However, the disclosed technique described above does not disclose any technique concerning a binding protein molecule-selectively recognizing and binding to the surface of a substrate material typified by an inorganic substance or a labeling agent. Therefore, when a structure in which the binding protein or a complex protein is arranged on a substrate is produced, the arrangement must be performed by a conventionally known method, for example, a method involving chemically modifying the substrate or the above-described binding protein to arrange the binding protein on the substrate through a covalent bond. Similarly, when the binding protein is bound to a fine particle of a metal or a semiconductor substance, and a labeling agent, it is also necessary to chemically modify the fine particle to be bound or the binding protein. Such chemical modification often targets amino residues or carboxyl groups contained in large numbers in the molecule of a protein, and a site involved in the reaction is nonselective. Therefore, a site exerting desired activity may be a substrate-binding or labeling site and, as a result, the desired activity of the protein may be reduced.

Moreover, such a problem is likely to arise in not only the technique of conversion into microdevices but the production of sensing elements such as biosensors. Thus, it is important to immobilize a molecule capturing a target substance such as an antibody on a substrate while molecular orientation that sufficiently exerts its capturing function is maintained.

DISCLOSURE OF THE INVENTION

A protein capable of binding to gold according to the present invention is a protein having affinity for gold, and is characterized by including a gold-binding site containing at least a portion of an antibody to gold.

According to one aspect of the present invention, there is provided a gold-binding complex protein, including:

(1) a first domain containing a protein having affinity for gold; and (2) a second domain containing a protein having a binding site to a certain substance.

According to another aspect of the present invention, there is provided a structure, including a substrate and a protein, in which the substrate contains gold in at least a portion of its surface and the protein is a gold-binding complex protein having the above configuration.

According to another aspect of the present invention, there is provided a nucleic acid encoding a gold-binding complex protein having the above configuration. According to another aspect of the present invention, there is provided a vector including the nucleic acid.

According to another aspect of the present invention, there is provided a method of producing a structure having the above configuration, including the step of:

(1) preparing the substrate;
(2) producing the gold-binding complex protein; and
(3) arranging the gold-binding complex protein on the substrate.

According to another aspect of the present invention, there is provided a kit for detecting a target substance, including a substrate and a gold-binding complex protein for forming a structure having the above configuration, and detection means for detecting the binding of the target substance to the structure.

According to another aspect of the present invention, there is provided a connecting member for labeling a target substance with a labeling agent, including:

one or more sites binding to the target substance and one or more sites binding to the labeling agent, in which:

the site binding to the target substance and the site binding to the labeling agent each independently bind to a substance to be bound; and at least one of the site binding to the labeling agent and the site binding the target substance contains a protein having the above configuration.

According to another aspect of the present invention, there is provided a method of detecting a target substance, in which the target substance is bound and labeled with a labeling agent to detect the target substance bound with the labeling agent, including the step of:

binding the labeling agent to the target substance via a connecting member having the above configuration.

According to another aspect of the present invention, there is provided a kit for detecting a target substance, including: a labeling agent; a connecting member having the above configuration; and detection means for detecting a state in which the labeling agent is bound to the target substance via the connecting member.

The gold-binding complex protein according to the present invention includes a gold-binding site and a structure portion. Therefore, when a functional substance linking and binding to the gold-binding protein is immobilized on the surface of a gold substrate, the immobilization does not affect the original function of the functional substance. Moreover, because no reagent is used in the immobilization, the functional substance does not suffer from any chemical reaction that affects its function. Furthermore, by keeping a distance from the gold substrate, the functional substance does not undergo interaction from the substrate that affects its function.

In addition, the gold-binding complex protein of the present invention includes several binding sites to at least gold and a certain substance. This allows a structure forming a layered body composed of at least (i) a substrate having gold in at least a portion of its surface, (ii) the gold-binding complex protein of the present invention, and (iii) a certain substance capable of binding to the gold-binding complex protein of the present invention. In this case, because the gold-binding complex protein of the present invention has a sterically stable β sheet structure of an antibody variable region domain, space can be kept between the gold substrate and the certain substance, and the domain (e.g., the second domain) of the gold-binding protein, which is bounded with gold or a substance other than gold (e.g., a labeling agent) does not undergo some interaction from the substrate containing gold and can retain the binding ability. Moreover, this allows the formation of a very thin and fine layered structure. Using those properties of the gold-binding protein of the present invention, a detection device can be obtained. For example, the gold-binding complex protein of the present invention capable of binding to a desired substance is provided in a thin gold layer, a sensing element for the desired substance car be made. A detection method thereof can provide optical means, for example, means with the use of surface plasmon resonance.

On the other hand, when a substance containing gold is given as a labeling agent, the gold-binding protein of the present invention can be used as a connecting member for binding the labeling agent containing gold to a target substance. According to this form as the connecting member, representative effects described below can be obtained.

As a first effect, the gold-binding protein has one or more of each of sites binding to a target substance and a labeling agent and each of the binding sites binds to a substance to be bound independently from each other to thereby provide an excellent connecting member capable of labeling the target substance and not showing the reduction in the ability of a substance to be labeled to bind to the target substance, which is perceived as a problem caused by the binding of the labeling agent in conventional labeling method. As a second effect, the connecting member is a biopolymer, more particularly, a protein, and is thereby expected to have high affinity resulting from the interaction of the surface of the target substance with several amino residues of the protein. As a third effect, the connecting member is an antibody variable region and is expected to have binding specificity because the binding site is defined in the configuration determined by the higher order structure. As a fourth effect, the labeling agent is a substance containing gold to thereby allow not only the measurement of the quantity of scattered light for a sample, but electric measurement with the use of its electric properties, in addition to optical measurement to which the principles of enhanced Raman or localized plasmon are applied. As a fifth effect, using the connecting member according to the present invention, a detection method and a detection kit added simultaneously or optionally with the target substance/connecting member/labeling agent can be provided.

BEST MODES FOR CARRYING OUT THE INVENTION

Figure 1:
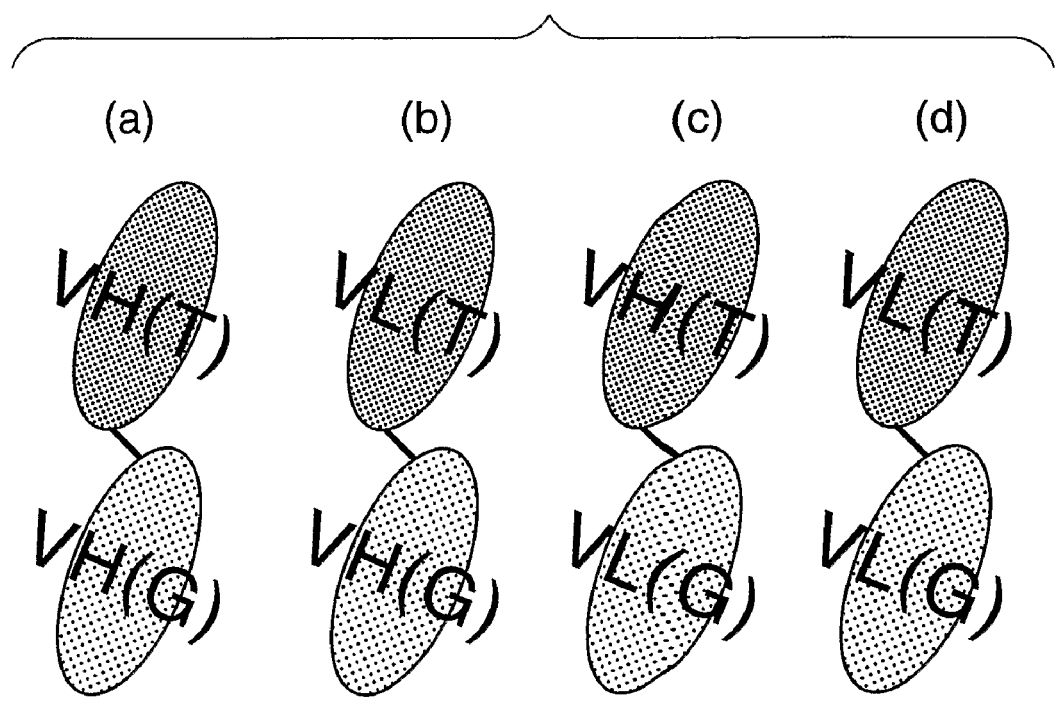
FIG. 1 is a diagram schematically showing the constitution of a structure in an example of a complex protein according to the present invention.

Hereinafter, a gold-binding protein according to the present invention, a complex protein by the use of the same, and uses thereof will be described.

(1) Gold-Binding Protein

Antibody

The gold-binding protein of the present invention includes at least a portion of an antibody. Examples of an antibody used for the binding with gold as shown in the present invention includes antibodies having an affinity for gold that are produced by lymphoid cells in all vertebrates, and a protein having an amino acid sequence with the deletion, substitution, or addition of one or several amino acids in the amino acid sequence of the antibodies and having relationship with the antibodies in the structure and the function, that is, maintaining a desired affinity for gold. Although antibodies are categorized according to the classification of their properties (immunological or physical) into IgG, IgM, IgA, IgD, and IgE, any of antibodies in the classification may be used in the present invention. Moreover, those antibodies may form a multimer. For example, IgA forms a dimer and IgM forms a pentamer, presenting no problem as long as they are in a shape capable of binding to gold. Procurement of gold-binding antibody. Moreover, antibodies may be IgW and IgY as long as they are for in vitro use.

As a method of obtaining the gold-binding antibody of the present invention, a technique of preparing anti-serum and a technique of producing a monoclonal antibody by cell fusion, which have been conventionally performed, can be appropriately selected and performed. For example, an appropriate animal for immunization is immunized with a gold fine particle to be bound in the present invention, and an antibody is collected from serum after the confirmation of increase in the antibody titer. The above-described immunization is generally performed by a method in which a gold fine particle as an antigen is diluted to an appropriate concentration with an appropriate solvent, for example, a physiological saline solution, and this solution is intravenously or intraperitoneally administered together with, if necessary, the Freund complete adjuvant, to an animal 3 to 4 times at intervals of 1 to 2 weeks. The animal thus immunized is anatomized at the 3 day post-final immunization and a splenocyte obtained from the excised spleen is used as an immunocyte. An immunizing gold fine particle has a size of preferably 10 nm or smaller, more preferably 2 nm or smaller. In addition, it is more preferred that the gold fine particle be covalently attached to a protein such as serum albumin and be rendered hapten. Heretofore, it has been expected that an antigen hard to produce immune reaction is also recognized as a portion of a certain protein antigen and its production is induced by the formation of a complex between the antigen and the protein antigen.

The obtained antibody may be polyclonal and is, however, given as a monoclonal antibody to thereby allow the selection of a clone having high specificity for gold. The monoclonal antibody can be obtained by cloning a cell producing it. In general, an immunoglobulin-forming cell such as the splenocyte collected from an immunized animal is fused to a tumor cell to thereby allow the formation of a hybridoma (Gulfre G., Nature 266. 550-552, 1977). For example, tumor cells include myeloma cells such as a mouse-derived myeloma P3/X63-AG8. 653 (ATCC No. CRL-1580), P3/NSI/1-Ag4-1 (NS-1), P3/X63-Ag8. U1 (P3U1), SP2/0-Ag14 (Sp2/0, Sp2), NS0, PAI, F0, or BW5147, a rat-derived myeloma 210RCY3-Ag. 2. 3., and a human-derived myeloma U-266AR1, GM1500-6TG-A1-2, UC729-6, CEM-AGR, DIR11, or CEM-T15.

In the screening of a cell producing the monoclonal antibody, the cell is cultured in a titer plate and the reactivity of a culture supernatant in a well where proliferation is observed to the above-described gold fine particle can be measured by, for example, enzyme immunoassay such as radio immunoassay (RIA) or enzyme-linked immuno-solvent assay (ELISA), or immunoprecipitation. Alternatively, affinity for gold can be also quantitatively measured with a surface plasmon resonance (SPR) device.

Antibody Fragment

An antibody fragment described in the present invention refers to the region of a portion of a monoclonal antibody, and specific examples thereof include F(ab')2, Fab', Fab, Fd, a variable fragment of antibody (Fv), single chain Fv (scFv), disulphide stabilized Fv (dsFv), and a single domain antibody (dAv) composed of a heavy chain variable region (VH) or a light chain variable region (VL).

"F(ab')2" and "Fab'" as used herein can be obtained by treating an antibody with, for example, pepsin or papain as a proteolytic enzyme. They refer to antibody fragments produced by digestion in the vicinity of a disulfide bond present between two heavy chains (H chains) in a hinge region of an antibody. For example, when IgG is treated with papain, the IgG is cleaved upstream of a disulfide bond present between two H chains in the hinge region to give two homologous fragments in which a light chain (L chain) composed of a light chain variable region (VL) and a light chain constant region (CL) and a heavy chain (H chain) composed of a heavy chain variable region (VH) and a heavy chain constant region 1 (CH1) are bound through a disulfide bond at the C-terminal region. Each of those two homologous antibody fragments is referred to as Fab'. Alternatively, when IgG is treated with pepsin, the IgG is cleaved downstream of a disulfide bond present between two H chains in the hinge region to allow the production of an antibody fragment slightly larger than the above-described two Fab' linked in the hinge region. This antibody fragment is referred to as F(ab')2.

The gold-binding protein of the present invention may be Fab' or F(ab')2 described above. The gold-binding protein may also be an Fd fragment in which VH and the above-described CH1 are bound.

Moreover, the gold-binding protein may be a variable fragment of antibody (Fv) or a portion thereof, for example, a heavy chain variable region (VH) or a light chain variable region (VL) constituting Fv or a portion thereof. On the other hand, for a complex composed of the above-described VH or VL, a single chain Fv (scFv) having the carboxy terminal of one region and the amino terminal of another region linked via peptide composed of several amino acids can be used. It is preferred that VH/VL (not in particular order) formed of the above-described scFv be provided with a linker composed of, one or more amino acids. It is important that the residue length of the amino acid linker be designed not to have such a binding force that inhibits the formation of a structure necessary for the binding of the antigen with VH or VL. As a specific example, the amino acid linker generally has 5 to 18 resides in length, with 15 residues more widely used and studied. Those fragments can be obtained by a genetic engineering approach.

Moreover, although either of VH and VL may be single domain dAb, the single domain structure is often unstable in general and may be therefore stabilized by chemical modification such as PEG modification. Moreover, variable region, VHH of camelid heavy chains (J. Mol. Biol, 311: p 123, 2001) and variable region of immunoglobulin-like molecules of Nurse Shark, IgNAR that exist and can function as heavy chain only antibodies in vivo can be used. Moreover, interface of VH/VL or alike may be introduced by drawing upon equivalents of heavy chain only antibodies to increase stability when VH or VL of antibodies that are composed of heavy chain and light chain represented by those of humans and mice are used as domain units as shown in FIGS. 1 to 4.

A gold-binding site can include at least one selected from (1) antibody heavy chain variable region (VH), a variant, and a portion thereof, and (2) antibody light chain variable region (VL), a variant, and a portion thereof. Preferable examples of the antibody heavy chain variable region (VH) include a protein including at least one of amino acid sequences of SEQ ID NOs.: 1 to 48, and preferable examples of the antibody light chain variable region (VL) include a protein including at least one of amino acid sequences of SEQ ID NOs.: 49 to 57. A protein having affinity for gold and containing one or more amino acid sequences with the deletion, substitution, or addition of one or several amino acids in each of these amino acid sequences of SEQ ID NOs.: 1 to 57 can be similarly utilized.

Procurement of Antibody Fragment Having Affinity for Gold

Procurement by Enzyme Treatment

The above-described antibody is treated with some enzyme to allow the procurement of an antibody fragment having the antigen-binding site and the antigen-binding ability of the antibody to some extent. For example, a Fab fragment or an analogue thereof can be obtained by treating the obtained antibody with papain. A F(ab')$_2$ fragment or an analogue thereof can be obtained by treating the obtained antibody with pepsin. The above-described antibody fragment is also produced by a chemical degradation method in addition to the above-described enzymatic approach. This antibody fragment can be used without a problem as long as it has the ability to bind to gold.

A method of obtaining the above-described Fab', Fv, or dAb of VH or VL according to the present invention may also be procurement by the use of a genetic engineering approach. An example thereof is a method in which a gene library of the VH or VL is produced and comprehensively expressed as a protein to select a corresponding gene based on affinity for gold or a target substance. The gene library can be obtained from, for example, cord blood, tonsil, bone marrow, or peripheral blood cells or splenocytes. For example, mRNA is extracted from a human peripheral blood cell and cDNA is synthesized. Next, a sequence encoding human VH or VL is used as a probe to produce a cDNA library of the human VH or VL. For example, primers capable of extensively amplifying human VH family (VH1 to 7) per family and primers capable of amplifying human VL are known in the art. RT-PCR is performed by combining a primer with each of such VH or VL to give a gene encoding the VH or VL. Alternatively, it is also possible to use a phage display method. In the phage display method, a gene library encoding VH, VL, or a complex containing them (e.g., Fab, scFv) is bound to a gene encoding a coat protein of the phage to produce a phagemid library that is in turn transformed into *E. coli* and expressed as phages having a variety of VHs or VLs as a portion of the coat protein. Those phages are used to allow selection based on affinity for gold or a target substance, as described above. A gene encoding VH or VL that is displayed as a fusion protein by the phage is encoded by the phagemid in the phage and can be therefore identified by DNA sequencing.

The present invention also includes a nucleic acid encoding the above-described gold-binding protein. The present invention further includes a constituent composed of a nucleic acid that is given as a gene vector to be expressed as a protein for transforming a host cell (e.g., a conventionally known protein-expressing cell derived from *E. coli*, yeasts, mice, or humans) to allow the expression of the above-described gold-binding protein. The gold-binding protein of the present invention that can be expressed by one expression vector can be selected and designed from the whole molecules of an antibody or an antibody fragment thereof F(ab')2, Fab, Fv(scFV), VH, or VL, or a complex thereof. When a plurality of the above-described antibody fragments are encoded by one expression vector, each of the antibody fragments can be independently expressed as an individual polypeptide chain. It is also possible to construct a vector that expresses the antibody fragments as one polypeptide chain in which the domains are linked successively or via an amino acid.

In the constitution of the vector for expressing the gold-binding protein of the present invention, the vector can be designed and constructed by integration into constitution or the like necessary for expressing a transgene, such as a known promoter, depending on a selected host cell. The vector can be constructed with reference to the constitution of a known promoter or the like depending on a selected host cell. When *E. coli* or the like is used as a host cell, the gold-binding protein of the present invention or a constituent thereof as a foreign gene product is immediately removed into the outside of the cytoplasm to thereby allow reduction in degradation by protease. Moreover, it is known that, even if this foreign gene product is toxic for a bacterium, its effect can be reduced by secreting the foreign gene product to the outside of the bacterium. Most proteins secreted through a known cytoplasmic membrane or inner membrane usually have signal peptides at the N terminals of their precursors, which are cleaved by signal peptidase in the secretion process to turn the precursors into mature proteins. Most signal peptides have basic amino acids, hydrophobic amino acids, and cleavage sites by signal peptidase, which are located at their N terminals.

The gold-binding protein of the present invention can be secreted and expressed by locating a nucleic acid encoding a conventionally known signal peptide typified by pelB on the 5' side of a nucleic acid encoding the gold-binding protein.

Several gold-binding proteins of the present invention or several polypeptide chains each composed of plural antibody fragments can be also inserted each independently into one vector. In this case, a nucleic acid encoding pelB can be located on the 5' side of each domain or a nucleic acid encoding the polypeptide chain to facilitate secretion. Alternatively, when the gold-binding protein is expressed as a polypeptide chain composed of one or more domains, a nucleic acid encoding pelB can be located on the 5' side of the polypeptide chain to thereby facilitate secretion, as described above. The gold-binding protein of the present invention in which a signal peptide is fused at its N terminal as described above can be purified from a periplasm fraction and a medium supernatant.

In consideration of convenience in procedures of purifying the expressed protein, it is possible to arrange, by genetic engineering, a tag for purification at the N or C terminal of a polypeptide chain formed of an antibody molecule, or each independent antibody fragment or several antibody fragments successively linked. Examples of the above-described tag for purification include a histidine tag composed of six consecutive histidine residues (hereinafter, His×6) and the glutathione-binding site of glutathione-5-transferase. Examples of a method of introducing the tag include: a method in which a nucleic acid encoding the tag for purification is inserted at the 5' or 3' end of a nucleic acid encoding the gold-binding protein in the above-described expression vector; and the use of a commercially available vector for introducing the tag for purification.

A method of producing the gold-binding protein of the present invention by the use of the above-described expression vector will be described hereinafter. A conventionally known host protein-expressing cell is transformed with a vector for expressing the gold-binding protein, which is designed in accordance with the host cell, to synthesize the gold-binding protein of the present invention or the polypeptide chain as a component thereof into the host cell by the use of a protein synthesis system in the host cell. Thereafter, a desired protein accumulated or secreted outside or inside the host cell can be purified and thereby obtained from the inside of the cell or a cell culture supernatant. For example, when E. coli is used as a host cell, the E. coli can be constructed to facilitate secretion and expression to the outside of the cytoplasm by locating a nucleic acid encoding a conventionally known signal peptide typified by pelB on the 5' side of a nucleic acid encoding the gold-binding protein of the present invention.

When several polypeptide chains constituting the gold-binding protein of the present invention are expressed in one expression vector of the present invention, a nucleic acid encoding pelB can be located on the 5' side of a nucleic acid encoding each of the polypeptide chains to facilitate secretion to the outside of the cytoplasm at its expression. The gold-binding protein of the present invention in which a signal peptide is fused at its N terminal as described above can be purified from a periplasm fraction and a medium supernatant. In a purification method, a nickel chelate column can be used for purification when the tag for purification is a His-tag, and an immobilized glutathione column can be used for purification when the tag for purification is GST.

The gold-binding protein of the present invention that is expressed in a bacterium can be also obtained with insoluble granules. In this case, the insoluble granules can be centrifuged from a cell homogenized solution in which the bacterium obtained from culture solution is homogenized with a French press or ultrasound. The obtained insoluble granule fraction can be solubilized with a buffer solution containing a conventionally known denaturant having urea and guanidine hydrochloride, followed by purification with a column as described above under a denaturation condition. For the obtained column elution fraction, the removal of the denaturant and the reconstruction of an active structure can be performed by a refolding procedure. As the refolding procedure, any of conventionally known methods can be appropriately used. More particularly, a stepwise dialysis method or dilution method can be used depending on a desired protein.

Each of the domains or each of the polypeptide chains of the gold-binding protein of the present invention can be expressed in an identical cell or can be complexed coexistently with one another after being expressed using another host cell.

In addition, using a vector encoding the gold-binding protein of the present invention, the protein can be also expressed in vitro with a cell extract solution. Examples of the cell extract solution preferably used include E. coli, a wheat germ, and a rabbit reticulocyte. However, the synthesis of a protein with the cell extract solution is generally performed under a reduction condition. Therefore, it is more preferred that some treatment be performed for forming a disulfide bond in an antibody fragment.

The preferred dissociation constant ($K_D$) of the gold-binding protein of the present invention is $10^{-6}$ M or less under a buffer condition in the presence of 0.1% TWEEN 20, more preferably $10^{-8}$ M or less. The inventors of the present invention have confirmed by study that a protein material cannot attach to gold on the above-described condition even for the protein material such as BSA having relatively large nonspecific attachment to gold. If the $K_D$ value is $10^{-6}$ or less, the attachment behavior of a nonspecifically adhesive protein as described above can be sufficiently distinguished. In addition, when the $K_D$ value is $10^{-8}$ or less, the gold-binding protein can sufficiently function as an anchor molecule for immobilization.

Expression of Antibody Fragment Protein

The gold-binding protein is cleaved with a desired restriction enzyme, for example, NcoI/NheI in the above-described case, to give DNA encoding a gold-binding antibody fragment. This can be introduced into a conventionally known plasmid for expressing a protein in accordance with a host cell to thereby give an antibody fragment. For example, when E. coli is used as a host cell and a desired antibody fragment is collected from an extracellular expression or periplasm fraction, a conventionally known signal peptide can be introduced upstream of a gene encoding the above-described antibody fragment. The signal peptide includes pelB. For easily purifying a desired protein from a culture supernatant or a bacterial fraction after expression, a conventionally known tag for purification may be fused. More particularly, six histidine residues (His×6) or the glutathione-binding site of glutathione-5-transferase can be introduced to give a fusion protein. In the case of the His-tag, this fusion protein can be easily purified with a metal chelate column such as nickel. In the case of the GST tag, purification can be performed with a column having a carrier such as Sepharose on which glutathione is immobilized.

Alternatively, when a desired protein expressed in a bacterium cannot be obtained with insoluble granules, the insoluble granules can be solubilized with a conventionally known buffer solution containing urea and guanidine hydrochloride, followed by refolding. Any of conventionally known methods can be appropriately used as the refolding procedure. More particularly, a stepwise dialysis method or dilution method can be used depending on a desired protein.

An antibody obtained as above and a fragment thereof, for example, Fab, (Fab')$_2$, Fc, VH or VL, or a complex thereof even having the deletion, substitution, or addition of one or several amino acids in their amino acid sequences do not depart from the scope of the present invention as long as they have affinity for gold.

The preferred dissociation constant ($K_D$) of the gold-binding protein of the present invention is $10^{-6}$ M or less under a buffer condition in the presence of 0.1% TWEEN 20, more preferably $10^{-8}$ M or less. The inventors of the present invention have confirmed by study that a protein material cannot attach to gold under the above-described condition even for the protein material such as BSA having relatively large nonspecific attachment to gold.

If the $K_D$ value is $10^{-6}$ or less, the attachment behavior of a nonspecifically adhesive protein can be sufficiently distinguished. In addition, when the $K_D$ value is $10^{-8}$ or less, the gold-binding protein can sufficiently function as an anchor molecule for immobilization.

Substance to be Bound Having Gold

A substance to be bound having gold can be selected and used from various substances having gold in at least a portion of their surfaces. When the gold-binding protein is selected by immunization, panning, or the like, the surface of the substance to be bound is composed of only gold for eliminating the contamination of proteins attaching to substances other than gold. Materials for the inner core substrate other than the surface can be selected and used from, as a matter of course, gold, and a variety of the other known materials. Moreover, the substance to be bound is preferably given in a particulate form, more preferably as a fine particle having 1 to 100 μmφ, to thereby allow increase in the specific surface area involved in the binding and to allow easy collection by centrifugation for collection at the completion of panning. In addition, the substance to be bound may be one obtained by evaporating gold onto any one of a variety of commercially available plastic plates, for example, a culture dish or a 96-well titer plate, as described below. In this case, in consideration of the wetted area of the gold surface and the molecular diffusion effect by stirring, the size and the number of wells are preferably determined.

The shape of the substance to be bound can be appropriately selected and used from shapes known in the art such as flattened, spherical, acicular, and porous shapes. A formation method can be appropriately selected from a physical or chemical vapor deposition method or a chemical production method with the use of gold chloride. The obtained surface containing gold may be previously washed with an acidic solution, an alkaline solution, an organic solvent, or the like, in order to eliminate impurities such as oxide layers, by-products, and contaminants and have desired condition of gold exposure.

Substrate

A structure available in a variety of uses can be obtained from a gold-binding protein and a substrate having gold forming at least a portion of its surface. A substrate having any shape and material can be used as long as it is provided with gold in at least a portion of its surface and can form the structure of the present invention. The material of the substrate used in the present invention may be any of materials that can form the structure of the present invention, and that include any one or more or a complex thereof selected from a metal, a metal oxide, an inorganic semiconductor, an organic semiconductor, glasses, ceramics, a natural polymer, a synthetic polymer, and a plastic. The shape of the substrate used in the present invention may be any of shapes that can form the structure of the present invention, and that include any one or more selected from plate, particulate, porous body-like, protruded, fibrillary, cylindrical, and reticular shapes.

Examples of the organic polymer compound for forming a substrate include an organic polymer compound manufactured through polymerization of polymerizable monomers selected from the group consisting of: styrene polymerizable monomers such as styrene, α-methylstyrene, β-methylstyrene, o-methylstyrene, m-methylstyrene, p-methylstyrene, 2,4-dimethylstyrene, p-n-butylstyrene, p-tert-butylstyrene, p-n-hexylstyrene, p-n-octylstyrene, p-n-nonylstyrene, p-n-decylstyrene, p-n-dodecylstyrene, p-methoxystyrene, and p-phenylstyrene; acrylate polymerizable monomers such as methyl acrylate, ethyl acrylate, n-propyl acrylate, isopropyl acrylate, n-butyl acrylate, isobutyl acrylate, tert-butyl acrylate, n-amyl acrylate, n-hexyl acrylate, 2-ethylhexyl acrylate, n-octyl acrylate, n-nonyl acrylate, cyclohexyl acrylate, benzyl acrylate, dimethyl phosphate ethyl acrylate, diethyl phosphate ethyl acrylate, dibutyl phosphate ethyl acrylate, and 2-benzoyloxy ethyl acrylate; methacrylate polymerizable monomers such as methyl methacrylate, ethyl methacrylate, n-propyl methacrylate, isopropyl methacrylate, n-butyl methacrylate, isobutyl methacrylate, tert-butyl methacrylate, n-amyl methacrylate, n-hexyl methacrylate, 2-ethylhexyl methacrylate, n-octyl methacrylate, n-nonyl methacrylate, diethyl phosphate ethyl methacrylate, and dibutyl phosphate ethyl methacrylate; methylene aliphatic monocarboxylic acid esters; vinyl esters such as vinyl acetate, vinyl propionate, vinyl benzoate, vinyl butyrate, vinyl benzoate, and vinyl formate; vinyl ethers such as methyl vinyl ether, ethyl vinyl ether, and isobutyl vinyl ether; and vinyl polymerizable monomers including vinyl ketones such as methyl vinyl ketone, hexyl vinyl ketone, and isopropyl vinyl ketone.

Further, examples of the inorganic solids may include, but are of course not limited to: clay minerals such as kaolinite, bentonite, talc, and mica; metallic oxides such as alumina, titanium dioxide, zinc oxide, magnetite, ferrite, NbTa composite oxide, $WO_3$, $In_2O_3$, $MoO_3$, $V_2O_5$, and $SnO_2$; insoluble inorganic salts such as silica gel, hydroxyapatite, and calcium phosphate gel; metals such as gold, silver, platinum, and copper; semiconductor compounds such as GaAs, GaP, ZnS, CdS, and CdSe; glass; silicon; and composites thereof.

Examples of films and sheets that may be used for forming the substrate of the present invention include, but are of course not limited to: films composed of plastics such as polyethylene terephthalate (PET), diacetate, triacetate, cellophane, celluloid, polycarbonate, polyimide, polyvinyl chloride, polyvinylidene chloride, polyacrylate, polyethylene, polypropylene, and polyester; porous polymer membranes composed of polyvinyl chloride, polyvinyl alcohol, acetyl cellulose, polycarbonate, nylon, polypropylene, polyethylene, and teflon; wooden boards; glass boards; silicon substrates; fabrics such as, cotton, rayon, acrylic, silk, and polyester; paper such as good quality paper, medium quality paper, art paper, bond paper, recycled paper, baryta paper, cast coated paper, corrugated paper, and resin coated paper. Note that the materials of those films and sheets may also be smooth or uneven.

Examples of the substrate include: base plates made of silicon, silica, glass, quartz glass, and so on, microflow paths and holes (pores) formed in the base plates by means of photolithography, etching, and sand blast, or those having surfaces on which thin films of gold, silver, and platinum are formed; base plates made of polydimethyl silonane (PDMS), polymethyl methacrylate (PMMA), polyethylene terephthalate (PET), polycarbonate (PC), polystyrene (PS), and so on and microflow paths and holes (pores) formed therein by means of molding techniques; carbon nanotubes, carbon nanohones, fullerenes, diamonds, or aggregates thereof; nanowhiskers constructed of alumina, carbon, flullerene, ZnO, and so on; mesoporous thin films, fine particles, and monolith structural members made of $SiO_2$, aluminosilicate, other methallosillicates, $TiO_2$, $SnO_2$, $Ta_2O_5$, and so on; fine particles of gold, silver, copper, platinum, and so on; iron-oxide fine particles of magnetite, ferrite, hematite, gammna hematite, maghemite, and so on; an aluminum/silicon mixture films and silicon-oxide nano structural members obtained therefrom by means of anodic oxidation; porous alumina thin films; alumina nonohole structures; and silicon nano-wires, but not limited to them.

In addition, the dimensions of the substrate of the present invention can be selected variously depending on its intended use application.

Target Substance Detecting Kit

A kit for detecting a target substance can be obtained using the configuration of the gold-binding protein of the present invention added with affinity to the target substance. For instance, a kit for detecting a target substance can be constructed of: both a substrate and a gold-binding complex protein for forming the above structural member; and a detecting member for detecting the binding of a target substance to the structural member. For instance, the binding of a protein containing a gold-binding protein to a target substance can be detected such that gold or a labeling agent containing gold is added to a target substance in a state of being bound to a protein containing a gold-binding protein and a physical or chemical procedure is then carried out to detect the gold or the target substance. Alternatively, when a target substance is one that contains gold, the affinity of a gold-binding protein to gold is utilized to allow the gold-binding protein to bind to the gold-containing labeling agent and the binding state thereof is then detected. In this case, the marker used may be one which will be described later in the description of a connecting member. Furthermore, for example, the binding between the labeling agent and the gold-binding protein can be detected by means of a change in physical value, such as an optical, electrical, or thermal change.

By the way, the structure added with the affinity to the labeling agent may be preferably one that utilizes a gold-binding complex protein described later or a gold-binding protein as a binding member between a target substance and a labeling agent.

Surface Plasmon Resonance Apparatus

In addition, the binding of a protein that contains a gold-binding protein to gold can be quantitatively determined using, for example, a conventionally-known surface plasmon resonance measuring apparatus. In general, the surface plasmon resonance is a method of determining a change in refractive index on a gold thin film formed on a glass base plate by a change in resonance angle generated by resonance between free electrons on the gold thin film and an evanescent wave generated con the boundary surface between glass and gold by incident light from a glass side at an incident angle of not more than the total reflection angle. The determined change in refractive index can be converted into the amount of a subject protein to gold and then evaluated.

Dissociation Constant ($K_D$)

The term "dissociation constant ($K_D$)" refers to a value obtained by dividing a "binding rate (Ka)" by a "dissociation rate (kd)" value. Those rates may be used as indexes that represent the affinity of the monoclonal antibody or a fragment thereof to gold. The rates can be analyzed according to any of various methods. In the present invention, however, the rates are determined from a binding curve using a measuring device, Biacore2000 (Amersham Pharmacia Biotech, Co., Ltd.) according to an analysis software bundled on the device.

(2) Gold-Binding Complex Protein

The gold-binding complex protein of the present invention includes two or more domains. Of those domains, at least one domain contains the gold-binding protein as constructed above. Exemplified complex proteins include those constructed as described below.

(a) A complex protein including a first domain 1 including a gold-binding protein as constructed above and a second domain 2 including a protein having a binding site specific to a particular substance.

(b) A complex protein further including at least one of a third domain 3 that forms a complex with the first domain and a fourth domain 4 that forms a complex with the second domain in addition to the first domain and the second domain.

In addition, at least one of the second to fourth domains may contain at least one protein having affinity for gold. In this case, each of those domains can be constructed by incorporating the gold-binding protein constructed as described above. Furthermore, the first to fourth domains may have affinity to a subject binding substance and their affinity can be then adjusted independently from one domain to another. Alternatively, two or more domains may have similar affinity. Those domains may be constructed from domains having different affinity.

Furthermore, at least two selected from the first to fourth domains may be contained in the same polypeptide chain. Examples of such a configuration of the gold-binding complex protein include the following structures.

(1) The structure in which the first domain and the second domain form one polypeptide chain.

(2) The structure in which the first domain and the second domain are bound via one or more amino acids.

(3) The structure in which the third domain and the fourth domain form one polypeptide chain.

(4) The structure in which the third domain and the fourth domain are bound via one or more amino acids.

(5) The structure consisting of a first polypeptide chain containing a first domain and a second domain and a second polypeptide chain containing a third domain and a fourth domain.

(6) The structure consisting of a first polypeptide chain containing a first domain and a second domain and a third polypeptide chain containing a third domain and a second domain.

(7) The structure consisting of a first polypeptide chain containing a first domain and a second domain and a fourth polypeptide chain containing a first domain and a fourth domain.

(8) The structure consisting of one polypeptide chain containing at least a first domain, a second domain, and a third domain.

(9) The structure consisting of one polypeptide chain containing at least a first domain, a second domain, and a fourth domain.

(10) The structure consisting of one polypeptide chain containing first to fourth domains.

Gold-Binding Complex Protein

A protein provided as a constituent of the gold-binding complex protein refers to a molecule that contains at least one polypeptide chain formed by allowing at least two amino acids to bind together, where the polypeptide chains can be folded into a specific three-dimensional structure to exert its inherent functions (e.g., conversion and molecular recognition). In addition, the gold-binding complex protein of the present invention is a complex protein that contains at least one binding site for gold and also at least one binding site for gold or other substance except gold to show affinity with polyvalent or multiple specificity. For instance, the complex protein may preferably include a first domain having a binding site for gold and containing at least a part of the variable region of a light chain (VL) or the variable region of a heavy chain (VH) of an antibody and a second domain having a binding site for a specific substance (hereinafter, referred to as a target substance) and containing at least a part of VH or VL. Hereinafter, VH and VL binding with gold refer to VH(G) and VL(G), respectively. VH and VL binding with a target substance refer to VH(T) and VL(T), respectively.

The antibody heavy chain variable region (VH) and the antibody light chain variable region (VL) are variable regions which respectively belong to an antibody heavy chain and an antibody light chain. In general, each of the antibody heavy chain variable region (VH) and the antibody light chain variable region (VL) is of a tubular structure and consists of about 110 amino acids and a layered structure is then formed with βsheet groups being arranged in opposite directions, while the layer structure is connected using a single S—S bond to form a very stable structure. In addition, it is known that the variable region (VH or VL) is a complementarity determining region (CDR) that determines the binding of antibodies to a wide variety of antigens. There are three CDRs in each of VH and VL and are separated from each other by framework regions having amino acid sequences with comparatively low diversity to thereby recognize a spatial arrangement of a functional group of a target recognition site, allowing the more advanced recognition of a specific molecule.

Hereinafter, an example of the gold-binding complex protein of the present invention will be described. As schematically illustrated in FIG. 1, the minimum unit of the gold-binding complex protein includes the first domain and the second domain. Exemplified combinations of the domains include VH(G)-VH(T) as shown in (a), VH(G)-VL(T) as shown in (b), VL(G)-VH(T) as shown in (c), and VL(G)-VL(T) as shown in (d). In this example, the first domain binds to gold and the second domain binds to a target substance, independently, without forming a complementary binding site between the first and second domains. The first and second domains may be independent polypeptide chains, respectively, or they may be continuously aligned and linked with each other. In terms of simplification of the manufacturing process and functional expression, a more preferable embodiment is to form a polypeptide chain by continuously linking the polypeptide chains. In the case of the polypeptide chain prepared by continuously linking the first domain and the second domain, the first domain and the second domain may be directly linked with each other or may be linked through a linker 5 made of one or more amino acids. The linker consisting of amino acids is preferably one consisting of 1 to 10 amino acids, more preferably one consisting of 1 to 5 amino acids. When the linker has an amino acid length of 11 to 15, complementary binding between the first domain and the second domain (becoming scFv) may be formed because of little restriction imposed on those domains due to their arrangements. For preventing the formation of a complementary complex between VH and VL, it is known that it is effective to burden the structural limitation between the domains by shortening the linker length. It is desirable that structural change that is brought when each of the first and the second domains binds to target substance does not effect its desired binding ability to target substance. Therefore, it is possible to set the linkers comprised of second structure such as ☐ helix or insert polypeptide that is not related to required binding character, as long as they do not significantly effect desired characters or productivity.

Furthermore, the gold-binding complex protein of the present invention forms a complex with the first domain. It may include a third domain that contains at least a part of VH or VL and/or a fourth domain that contains at least a part of VL or VH which forms a complex with the second domain. It is more desirable to allow the third domain to make a complex with the first domain to form a complementary gold-binding site with the first domain.

Figure 2A:
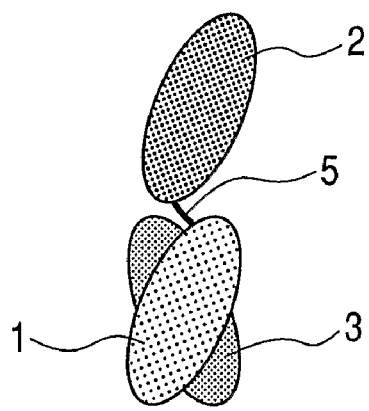
FIGS. 2A and 2B are, respectively, a diagram schematically showing the constitution of a structure in an example of a complex protein according to the present invention.
Figure 2B:
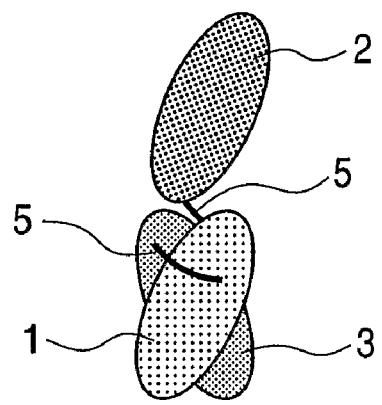

For instance, when the first domain is VH(G) as shown in the schematic diagrams in FIGS. 2A and 2B, the third domain is preferably VL which is able to form FV with the first domain, more preferably a structure formed such that a gold-binding site is formed by linking the first domain with the third domain.

As described above, the first domain and the third domain form Fv to attain structural stability and to be expected to prevent a decrease in function due to the structural change. Furthermore, as the third domain forms a gold-binding site by linking with the first domain, a further increase in binding ability (e.g., an increase in binding rate and suppression of dissociation rate) can be expected.

Furthermore, as shown in FIG. 2A, the first domain and the third domain may be respectively provided as independent polypeptide chains or may be linked with each other to form a polypeptide chain (e.g., third domain-first domain-second domain, as shown in the schematic diagram of FIG. 2B, the structure may be suitably determined such that the binding ability is exerted on gold and a target). Furthermore, as another example, the structure as shown in a schematic diagram of FIG. 3 may be allowable. In other words, it is a complex constructed of a polypeptide chain consisting of the first domain and the second domain and a polypeptide chain consisting of the third domain and the second domain. In this case, the binding with gold is attained by Fv or an Fv-like complex formed from the first and third domains and the first domain then functions as an anchor that binds to a target substance through the second domain.

Furthermore, the gold-binding protein of the present invention may include a fourth domain consisting of at least a part of VH or VL to form a complex with the second domain. It is desirable to form a binding site to the target substance together with the second domain in a complementary manner. For example, as shown in the schematic diagram of FIG. 4A, when the second domain is VL, the fourth domain is preferably VH which is able to form Fv with the second domain. More preferably, the second domain and the fourth domain are linked together to form a binding site against the target substance. Furthermore, as shown in a schematic diagram of FIG. 4B, a polypeptide chain may be formed by linking the first, second, and fourth domains together.

Especially in case that the protein binds to gold substrate via at least a portion of surface of the first domain while binds to target substance via the second and the fourth domain and that irreversible structural change occurs when the first domain binds to the substrate, it is possible to minimize the effect on binding abilities of the second and the forth domain by setting a linker.

Figure 5:
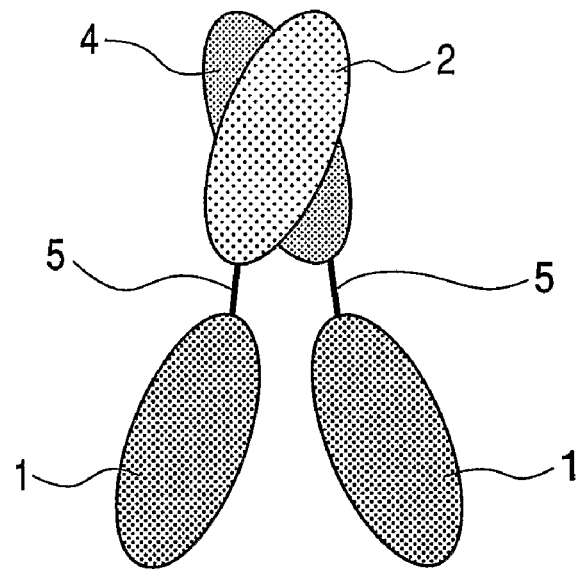
FIG. 5 is a diagram schematically showing the constitution of a structure in an example of a complex protein according to the present invention.

Moreover, the gold-binding protein of the present invention may be constructed as illustrated in a schematic diagram of FIG. 5. That is, it is a complex constructed of a polypeptide chain consisting of the first domain and the second domain and a polypeptide chain consisting of the first domain and the fourth domain. In this case, the complex binds to a target substance by means of Fv or an Fv-like complex which is made up of the second domain and the fourth domain to allow the first domain to function as an anchor for combining both polypeptide chains described above with gold.

Figure 6:
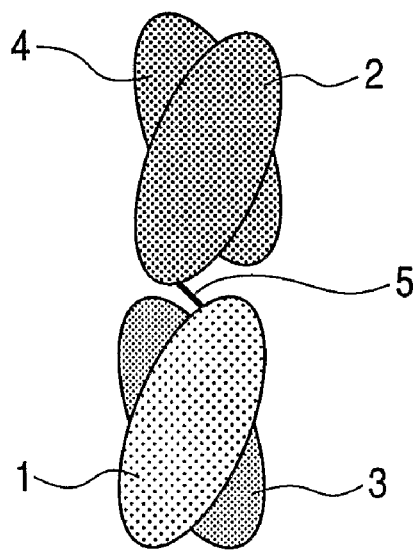
FIG. 6 is a diagram schematically showing the constitution of a structure in an example of a complex protein according to the present invention.
Figure 7:
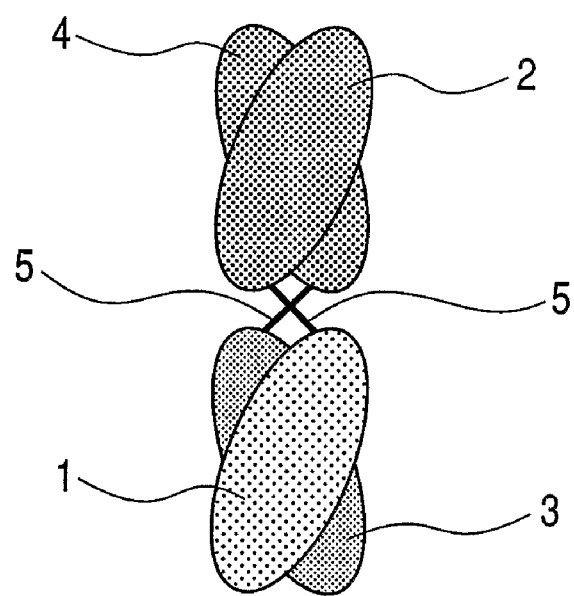
FIG. 7 is a diagram schematically showing the constitution of a structure in an example of a complex protein according to the present invention.

Furthermore, the gold-binding protein of the present invention may include the third and fourth domains together as constituent materials. As shown in a schematic diagram of FIG. 6, the third and fourth domains may be independent polypeptide chains, respectively. Alternatively, as shown in a schematic diagram of FIG. 7, it may be a polypeptide chain obtained by a linkage between polypeptide chains. When the gold-binding protein is provided as a linked polypeptide chain, the third domain and the fourth domain may be directly linked together or may be linked through a linker consisting of one or more amino acids as shown in FIG. 7. The length of the linker may be defined such that, as described above, the linker consisting of amino acid(s) has an amino acid length of preferably 1 to 10 amino acid, more preferably 1 to 5 amino acids.

Figure 8:
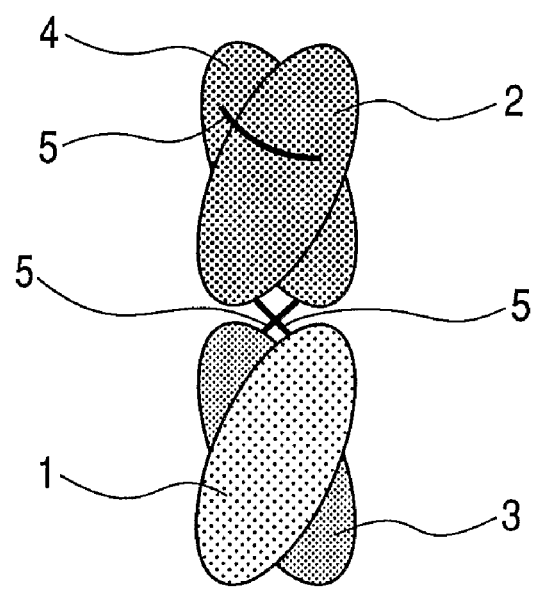
FIG. 8 is a diagram schematically showing the constitution of a structure in an example of a complex protein according to the present invention.

Furthermore, as shown in a schematic diagram of FIG. 8, the first to fourth domains may be linked together in a single polypeptide chain. In this case, those domains are arranged such that the first domain and the third domain can form a complex and then the complex can bind to gold while the second domain and the fourth domain can form a complex and then the complex can bind to gold and other substance except gold. Therefore, the linker is preferably provided between the domains. For instance, 1 to 5 amino acids are located between the first and second domains or between the third and fourth domains. Also, 15 to 25 amino acids are located between the second and fourth domains of amino acids. In the similar structure, each of or both of the first and second domains and the third and fourth domains may be replaced with each other.

The sequence of each domain in the single polypeptide chain may be suitably selected and defined depending on desired properties such as affinity for gold or a target and the long-term stability of the gold-binding protein.

The first domain is, for example, one comprising at least one amino acid sequence selected from SEQ ID No: 1 to SEQ ID No: 57. In each of those amino acid sequences, there is no problem as far as the amino acid retains its affinity for gold even though the amino acid sequence is subjected to the deletion, substitution, or addition of one or several amino acids. Furthermore, it may be used as the gold binding protein of the present invention without any problem as far as it shows affinity for gold even though the amino acid sequence is provided as one forming part of the amino acid sequences or provided as a complex thereof. Specific examples of VH of the present invention having SEQ ID No: 1 to SEQ ID No: 57 are represented in SEQ ID No: 58 to SEQ ID No: 74. Also, specific examples of VL of the present invention are represented in SEQ ID No: 75 to SEQ ID No: 77.

Preferably, the third domain contains one or more amino acids selected from SEQ ID No: 1 to SEQ ID No: 57. Furthermore, the third domain is more preferably defined by suitably selecting from SEQ ID No: 58 to SEQ ID No: 77 depending on the first domain.

The present invention also includes a nucleic acid that encodes the above gold-binding complex protein. In addition, the present invention also includes a construct consisting of a nucleic acid to be provided as a vector for transforming host cells (e.g., conventionally known protein-expressing cells from E. coli, yeast, mouse, human, or the like). Exemplified nucleic acid sequences that encode the first and third domains capable of constituting the gold-binding protein of the present invention are represented in SEQ ID No: 98 to SEQ ID No: 116.

Each domain of the gold-binding protein of the present invention, which can be expressed by one expression vector described above, may be designed by selecting from 1 to 4. When one expression vector is encoded by multiple domains of the gold-binding protein of the present invention, each domain can be expressed as an independent polypeptide chain. In addition, a vector configuration expressed as one polypeptide in which domains are bound directly or via an amino acid can be obtained. Furthermore, the configuration of the expression vector for the gold-binding protein of the present invention can be designed and constructed by incorporating transgenes such as known promoters into a constitution required for the expression thereof on the basis of host cells selected. The configuration of the vector can be constructed with reference to the configuration of known promoters or the like on the basis of host cells selected. Furthermore, when E. coli or the like is used as host cells, the gold-binding protein of the present invention, which is a foreign gene product, is quickly removed out of cytoplasm to reduce the decomposition of protease. Furthermore, when the gene product may be toxic for bacterial cells, it is possible to reduce its effect by secretion to the outside of cell bodies. In general, most of proteins secreted through the known cell membrane or inner membrane have signal peptides on their N terminals of the peptidase. During the secretion step, the signal peptidase cleaves the protein to make it a mature protein. Many signal peptides have basic amino acids, hydrophobic amino acids, and the cleavage sites of the signal peptidase at their N terminals.

The peptide chain can be expressed and secreted by arranging nucleic acid that encodes a conventionally known signal peptide typified by a single peptide pelB on the 5' end of the nucleic acid encoding the gold-binding complex protein of the present invention. In addition, each of domains that constitute the gold-binding complex protein of the present invention or a polypeptide chain constructed of two or more of the domains may be independently inserted into a single vector. In this case, the nucleic acid that encodes pelB is arranged on the 5' end of nucleic acid that encodes each of domains or a polypeptide chain to facilitate the secretion. For expressing the polypeptide chain as one consisting of one or more domains, likewise, the secretion of such a polypeptide chain can be facilitated by arranging the nucleic acid that encodes pelB on the 5' end of the polypeptide chain. In this manner, the gold-binding protein of the present invention, in which a signal peptide is fused on the N-terminal end thereof, or a domain used as a constituent thereof can be purified from the periplasma fraction and the supernatant of the culture. In addition, considering the easiness of work at the time of purifying the protein expressed, a purification tag may be arranged on each of independent domains or on the N or C terminal of the polypeptide chain formed by combining two or more domains by a genetic engineering procedure. The purification tag may be a histidine tag constructed of continuously arranged six histidine residues (hereinafter, referred to as His×6), a glutathione-binding site of glutathione-S-transferase, or the like. As a method of introducing the tag, for example, there is a method in which a nucleic acid encoding a purified tag is inserted into the 5' or 3' terminal of nucleic acid encoding a gold-binding protein in the expression vector, or a method with the used of a commercially available vector for introducing a purified tag.

Hereinafter, the method of manufacturing the gold-binding complex protein of the present invention using the above expression vector will be described.

The gold-binding complex protein of the present invention or a polypeptide chain to be provided as a constituent thereof is synthesized by: transforming a vector for expressing the gold-binding complex protein designed depending on host cells into host cells for expressing a conventionally known protein; and preparing a desired protein in the host cells using a protein synthesis system in host cells. After that, the intended protein being accumulated or secreted inside or outside the host cells is purified from the inside of the cells or the supernatant of cell culture.

For instance, in the case of using E. coli as host cells, nucleic acid that encodes a conventionally known signal peptide typified by pelB is arranged on the 5' end of nucleic acid that encodes the gold-binding complex protein of the present invention to thereby facilitate the secretory expression. For expressing two or more polypeptide chains to obtain each of domains that constitute the gold-binding complex protein of the present invention by means of one expression vector, nucleic acid that encodes pelB is arranged on the 5' end of nucleic acid that encodes each polypeptide chain to facilitate the secretion to the outside of cytoplasm. In this manner, the gold-binding protein of the present invention, in which a single peptide is fused on the N-terminal end thereof, can be purified from the periplasma fraction and the supernatant of the culture. As a purification method, when the purification tag is a His tag and when a column is a nickel chelate column or GST, the purification can be carried out using a glutathione immobilization column.

Furthermore, In addition, the gold-binding complex protein of the present invention expressed in bacterial cells can be obtained in the form of insoluble granule. In this case, the bacterial cells obtained from a culture medium may be crushed by a French press or an ultrasonic wave and then the insoluble granules are centrifuged from a cell homogenized solution. The resulting insoluble granule fraction is dissolved in a buffer solution containing a conventionally known denaturing agent including urea and guanicine hydrochloride salt and then purified through a column under denaturing conditions as described above. The resulting column eluent fraction may be subjected to a refolding work to remove the denaturing agent and reconstruct an active structure. The refolding method used may be suitably selected from any of those known in the art. Specifically, depending on a protein of interest, a serial dilution method, a dilution method, or the like may be used.

Each of domains or each of polypeptide chains of the gold-binding protein of the present invention may be expressed in the same host cell and then complexed, or alternatively expressed using other host cells and allowed to coexist to make a complex.

Furthermore, using a vector encoding the gold-binding protein of the present invention, the in vitro expression of a protein from a cell extract may be carried out. The cell extracts appropriately used herein include E. coli, wheat germ, and rabbit reticulocytes. However, the protein synthesis in the above cell-free extract is typically carried out under the reduction condition. Therefore, more preferable is to carry out any treatment for the formation of a disulfide bond in the antibody fragment.

The gold-binding complex protein of the present invention has a dissociation constant ($K_D$) of $10^{-6}$M or less, more preferably $10^{-8}$ M or less under the buffer condition of in the presence of 0.1% TWEEN 20. Under the above conditions, the inventors of the present invention have studied and confirmed that none of protein materials which have been considered to show comparatively high adsorption to gold can be adsorbed to gold. When the Kd value is $10^{-6}$ M or less, it can be sufficiently distinguishable from the adsorption behavior of protein having non-specific adsorptivity. Besides, $10^{-8}$ M or less allows a sufficient function as an anchor molecule for immobilization.

As one of the methods of acquiring an antibody heavy chain variable region (VH) or antibody light chain variable region (VL) having binding ability to a target substance having gold of the present invention, there is a method including: preparing a gene library of VH or VL described above; expressing them as proteins cyclopaedically; and making correspondence between the proteins and the genes to select one on the basis of affinity for gold or a target substance. The above gene library can be obtained from cord blood, tonsil, marrow, peripheral blood cells, splenic cells, or the like. For instance, mRNA is extracted from human peripheral blood cells to prepare cDNA. Subsequently, using a human VH- or VL-encoding sequence as a probe, cDNA library of human VH or VL is prepared. For instance, primers which can widely amplify the human VH families (VH1 to 7) every family and primers which can amplify human VL are known in the art. Every VH or CL, primers are combined together to carry out RT-PCR to acquire the VH- or VL-encoding gene. Alternatively, a phage display method may be used. The phage display method includes: combining a gene library for encoding VH, VL, or a complex (e.g., Fab, scFv) containing VH or VL with a gene that encodes a phage coat protein; preparing phagemid libraries; transforming the phagemid libraries into E. coli; and expressing as phages having various VH or VL as part of the coat protein. Using those phages, as well as the above description, it can be selected depending on affinity for gold or a target substance. Genes encoding VH or VL represented as a fusion protein in the phage is encoded in a phagemid of the phage. Therefore, it can be specified by subjecting to a DNA sequence analysis.

Furthermore, cells that produce an antibody of interest are collected from an animal immunized with gold or a target substance and then a VH or VL base sequence or an amino acid sequence can be specified using the same primers as those described above.

Furthermore, the third and fourth domains of the present invention can be designed against a target substance on the basis of an amino acid sequence of a variable region in a known antibody or a fragment thereof. In addition, when the antibody or the fragment thereof against a target substance is not obtained, it is possible to design as described above by analyzing an amino acid sequence after acquiring an antibody thereto. Both of the third domain and the fourth domain may be those that constitute the gold-binding protein of the present invention. In this way, the VH or VL base sequence thus obtained is used to prepare the gold-binding complex protein of the present invention.

Binding Object Having Gold

As a binding object used for the selection of a gold-binding protein by means of immunization, panning, or the like, those previously exemplified in the case of the gold-binding protein are available.

Substrate

The gold-binding complex protein of the present invention may be combined with a substrate to provide a structure which can be used in various kinds of applications. The substrates which can be used in the applications are those previously exemplified for the gold-binding protein.

Target Substance

The gold-binding complex protein of the present invention is constructed of a domain having affinity for gold and a domain having affinity for a target substance and thus it becomes possible to utilize the protein as a complex protein for detecting the target substance. The target substance provided as a detection subject may be any of molecules which can be provided as antigens in the respective procedures using antigen/antibody reactions. For instance, the target substances can be roughly classified into non-biological substances and biological substances.

Examples of non-biological materials with a high value of industrial utilization include PCBs and dioxins that are environmental pollutants having different chlorine substitution numbers and positions, and endocrine-disrupting substances, so called environment hormones (for example, hexachlorobenzene, pentachlorophenol, 2,4,5-trichloroacetic acid, 2,4-dichlorophenoxyacetic acid, amitrole, atrazine, alachlor, hexachlorocyclohexane, ethylparathion, chlordane, oxychlordane, nanochlor, 1,2-dibromo-3-chloropropane, DDT, kelthane, aldrin, endrin, dieldrin, endosulfan (benzoepin), heptachlor, heptachlor epoxide, malathion, methomyl, methoxychlor, mirex, nitrofen, toxaphene, trifluralin, alkylphenol (with carbon numbers of 5 to 9), nonylphenol, octynonylphenol, 4-octylphenol, bisphenol A, di-2-ethylhexl phthalate, butylbenzyl phthalate, di-n-butyl phthalate, dicyclohexyl phthalate, diethyl phthalate, benzo(a)pyrene, 2,4-dichlorophenol, di-2-ethylhexyl adipate, benzophenone, 4-nitrotoluene, octachlorostyrene, aldicarb, benomyl, kepone (chlordecone), manzeb (mancozeb), maneb, metiram, metribuzin, cypermethrin, esfenvalerate, fenvalerate, permethrin, vinclozolin, zineb, ziram, dipentyl phthalate, dihexyl phthalate, and dipropyl phthalate).

The biological substances include a biological substance selected from a nucleic acid, a protein, a sugar chain, a lipid, and a complex thereof, and more particularly include a biological substance selected from a nucleic acid, a protein, a sugar chain, and a lipid. In particular, the present invention can be applied to any of substances containing a substance selected from any of DNA, RNA, an aptamer, a gene, a chromosome, a cell membrane, a virus, an antigen, an antibody, lectin, hapten, a hormone, a receptor, an enzyme, peptide, sphingoglycolipid, and sphingolipid. In addition, a bacterium or cell itself that produces the above-described "biological substance" can also be a target substance as a "biological substance" of interest in the present invention.

A specific example of a protein includes a so-called disease marker. Examples thereof include: α-fetoprotein (AFP) as a marker for hepatocellular carcinoma (primary liver cancer), hepatoblastoma, metastatic liver cancer, and yolk sac tumor, which is an acidic glycoprotein produced by a hepatic cell in the fetal period and present in fetal blood; PIVKA-II that is an abnormal prothrombin appearing during hepatic parenchyma disorder and found to appear specifically for hepatocellular carcinoma; BCA225 as a marker for primary advanced breast cancer, and recurrent and metastatic breast cancer, which is a glycoprotein of an antigen immunohistochemically specific for breast cancer; basic fetoprotein (BFP) as a marker for ovarian cancer, testicular tumor, prostatic cancer, pancreatic carcinoma, biliary tract cancer, hepatocellular carcinoma, renal cancer, lung cancer, gastric cancer, bladder carcinoma, and colon cancer, which is a basic fetal protein found in a human fetal serum, intestine, and brain cell extract; CA15-3 as a marker for progressive breast cancer, recurrent breast cancer, primary breast cancer, and ovarian cancer, which is a sugar chain antigen; CA19-9 as a marker for pancreatic carcinoma, biliary tract cancer, gastric cancer, liver cancer, colon cancer, and ovarian cancer, which is a sugar chain antigen; CA72-4 as a marker for ovarian cancer, breast cancer, clorectal cancer, gastric cancer, and pancreatic carcinoma, which is a sugar chain antigen; CA125 as a marker for ovarian cancer (especially, serous cystadenocarcinoma), corpus uteri adenocarcinoma, Fallopian tube cancer, uterocervical adenocarcinoma, pancreatic carcinoma, lung cancer, and colon cancer, which is a sugar chain antigen; CA130 as a marker for epithelial ovarian cancer, Fallopian tube cancer, lung cancer, hepatocellular carcinoma, and pancreatic carcinoma, which is a glycoprotein; CA602 as a marker for ovarian cancer (especially, serous cystadenocarcinoma), corpus uteri adenocarcinoma, and uterocervical adenocarcinoma, which is a core protein antigen; CA54/61 (CA546) as a marker for ovarian cancer (especially, mucinous cystadenocarcinoma), corpus uteri adenocarcinoma, and uterocervical adenocarcinoma, which is a mother cell nucleus sugar chain-associated antigen; a carcinoembryonic antigen (CEA) most widely used at present for assisting in cancer diagnostic as a tumor-associated marker antigen such as colon cancer, gastric cancer, rectal cancer, biliary tract cancer, pancreatic carcinoma, lung cancer, breast cancer, uterine cancer, and urinary system carcinoma; DUPAN-2 as a marker for pancreatic carcinoma, biliary tract cancer, hepatocellular carcinoma, gastric cancer, ovarian cancer, and colon cancer, which is a sugar chain antigen; elastase 1 as a marker for pancreatic carcinoma, pancreatic cisterna, and biliary tract cancer, which is an exocrine pancreatic proteolytic enzyme present in pancreas and specifically hydrolyzing elastic fiber elastin of connective tissues (constituting arterial wall, tendon, or the like); an immunosuppressive acidic protein (IAP) as a marker for lung cancer, leukemia, esophageal cancer, pancreatic carcinoma, ovarian cancer, renal cancer, cholangioma, gastric cancer, bladder carcinoma, colon cancer, thyroid carcinoma, and malignant lymphoma, which is a glycoprotein present at high concentrations in ascites or serum of human cancer patients; NCC-ST-439 as a marker for pancreatic carcinoma, biliary tract cancer, breast cancer, colon cancer, hepatocellular carcinoma, pulmonary adenocarcinoma, and gastric cancer, which is a sugar chain antigen; γ-seminoprotein (γ-Sm) as a marker for prostatic cancer, which is a glycoprotein; a prostate-specific antigen (PSA) that is a glycoprotein extracted from human prostate tissues and present in only prostate tissues, thereby being a marker for a prostatic cancer; prostatic acid phosphatase (PAP) used as a tumor marker for prostatic cancer, which is an enzyme hydrolyzing phosphate under acid pH secreted by prostate gland; neuron-specific enolase (NSE) as a marker for lung cancer (especially, lung small cell carcinoma), neuroblastoma, nervous system neoplasm, pancreatic islet cancer, Gullet small cell carcinoma, gastric cancer, renal cancer, and breast cancer, which is a glycolytic enzyme specifically present in nervous tissues and neuroendocrine cells; a squamous cell carcinoma-associated antigen (SCC antigen) as a marker for uterine cancer (cervical squamous cancer), lung cancer, esophageal cancer, Head and neck cancer, and carcinoma cutaneum, which is a protein extracted and purified from the liver metastatic focus of uterocervical squamous cancer; a sialyl $Le^x$-i antigen (SLX) as a marker for pulmonary adenocarcinoma, esophageal cancer, gastric cancer, colon cancer, rectal cancer, pancreatic carcinoma, ovarian cancer, and uterine cancer, which is a sugar chain antigen; SPan-1 as a marker for pancreatic carcinoma, biliary tract cancer, liver cancer, gastric cancer, and colon cancer, which is a sugar chain antigen; a tissue polypeptide antigen (TPA) as a marker for esophageal cancer, gastric cancer, colorectal cancer, breast cancer, hepatocellular carcinoma, biliary tract cancer, pancreatic carcinoma, lung cancer, and uterine cancer, which is single-stranded polypeptide useful especially in the estimation of progressive cancer and recurrence precognition/therapeutic process observation in combination with other tumor markers; a sialyl Tn antigen (STN) as a marker for ovarian cancer, metastatic ovarian cancer, gastric cancer, colon cancer, biliary system cancer, pancreatic carcinoma, and lung cancer, which is a mother cell nucleus carbohydrate antigen; cytokeratin (CYFRA) as an effective tumor marker for detecting pulmonary non-small cell carcinoma, especially pulmonary squamous cancer; pepsinogen (PG) as a marker for gastric ulcer (especially, infraversion gastric ulcer), duodenal ulcer (especially, recurrent and intractable cases), Brunner's gland oma, Dzo ringer Ellison syndrome, and acute gastritis, which is an inactive precursor of two pepsins (PG I, PG II) as a proteolytic enzyme secreted into gastric juice; C-reactive protein (CRP) that is an acute phase reactant changed in blood plasma by tissue injury and infection and shows high level when necrosis occurs in heart muscle due to acute myocardial infarction or the like; serum amyloid A protein (SAA) that is an acute phase reactant changed in blood plasma by tissue injury and infection; myoglobin as a marker for acute myocardial infarction, muscular dystrophy, polymyositis, and dermatomyositis, which is a heme protein having a molecular weight of approximately 17,500 and present mainly in heart muscle and skeletal muscle; creatine kinase (CK)(three isozymes of CK-MM type derived from skeletal muscle, CK-BB type derived from brain and smooth muscle, and CK-MB type derived from heart muscle, and mitochondrial isozymes or immunoglobulin-bound type CK (macro CK)) as a marker for acute myocardial infarction, hypothyroidism, progressive muscular dystrophy, and polymyositis, which is an enzyme present mainly in the soluble fraction of skeletal muscle or heart muscle and emigrating into blood due to cellular lesion; troponin T as a marker for rhabdomyolysis, myocarditis, myocardial infarction, and renal failure, which is a protein with a molecular weight of 39,000 forming a troponin complex with troponins I and C on the thin filament of striated muscle and involved in the regulation of muscular contraction; ventricular muscle myosin light chain I as a marker for acute myocardinal infarction, muscular dystrophy, and renal failure, which is a protein contained in both skeletal muscle and heart muscle and for which a rise in the measurement means the disorder or necrosis of skeletal muscle and heart muscle; or chromogranin A, thioredoxin, and 8-OhdG that recently receive increasing attention as a stress marker.

Kit for Detecting Target Substance

The gold-binding complex protein according to the present invention can be used to constitute a kit for detecting a target substance. For example, the kit for detecting a target substance can be constituted, which includes: a gold-binding complex protein with the use of an antibody and a variant thereof specifically binding to the target substance in a second domain and a fourth domain optionally used, a substrate having a surface containing gold; and detection means for detecting the target substance immobilized on the substrate via the gold-binding complex protein. The detection of the target substance immobilized on the gold substrate via the gold-binding complex protein can be measured with the above-described surface plasmon resonance device. A method in which the substrate containing gold in a potion thereof is used as a labeling agent to detect the target substance can be utilized. The gold-binding complex protein described above can be used as a substance for mediating such a gold substrate, labeling agent, and target substance. The gold-binding complex protein formed using an antibody fragment recognizing and binding to the target substance can be used in the present invention.

EXAMPLES

Hereinafter, the acquisition and evaluation of a protein capable of binding to gold as an example of the present invention will be described in detail. However, the present invention is not limited to the contents described in "EXAMPLES".

Example 1

Preparation of Antibody Heavy Chain Variable Region VH Library

By using a Fab library derived from human adult peripheral blood B lymphocyte as a template, VH coding gene was subjected to DNA replication by means of the following primer in accordance with a method recommended by PCR (TAKARA BIO INC, LA kit). The primer was set as follows.

back primers (SEQ ID No: 78)
5'-TCGCAACTGCGGCCCAGCCGGCCATGGCCCAGGTGCAGCTGGTGCAG
TCTGG-3'

(SEQ ID No: 79)
5'-TCGCAACTGCGGCCCAGCCGGCCATGGCCCAGRTYCAGCTGGTGCAG
TCTGG-3'

(SEQ ID No: 80)
5'-TCGCAACTGCGGCCCAGCCGGCCATGGCCCAGSTRCAGCTGCAGSAG
TCRGG-3'

(SEQ ID No: 81)
5'-TCGCAACTGCGGCCCAGCCGGCCATGGCCSARGTGCAGKTGGTGGAG
TCTGG-3'

(SEQ ID No: 82)
5'-TCGCAACTGCGGCCCAGCCGGCCATGGCCCCAGTGTGAGGTGCAGCT
GGTGG-3'

(SEQ ID No: 83)
5'-TCGCAACTGCGGCCCAGCCGGCCATGGCCCAGGTGCAGCTACAGSAG
TGGGG-3' forward primers (SEQ ID No: 84)
5'-ATTCTCGACTGCTAGCTGAGGAGACGGTGACCAGGGTGCC-3'

(SEQ ID No: 85)
5'-ATTCTCGACTGCTAGCTGAAGAGACGGTGACCATTGTCCC-3'

(SEQ ID No: 86)
5'-ATTCTCGACTGCTAGCTGAGGAGACGGTGACCAGGGTTCC-3'

(SEQ ID No: 87)
5'-ATTCTCGACTGCTAGCTGAGGAGACGGTGACCGTGGTCCC-3'

(1) By using the Fab library as a template, the VH coding gene was amplified by PCR using the primer. PCR conditions: 95° C.×10 min (94° C.×1 min, 60° C.×2 min, 72° C.×2 min)×35 cycle, 72° C.×6 min).

Figure 11:
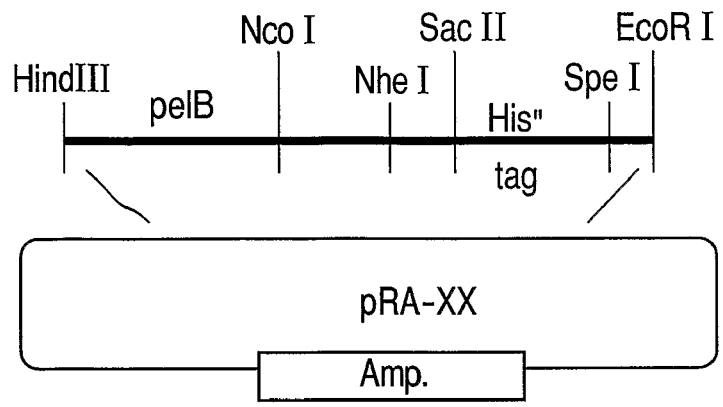
FIG. 11 is a schematic diagram of a vector for illustrating Examples of the present invention.

(2) A plasmid pRA-XX obtained by improving a multi-cloning site of pLUCK (Biochem Biophys Res Commun. 218, pp 682, 1996) as shown in FIG. 11 was prepared as a vector for protein expression. (Subsequent to HindIII, a nucleotide sequence encoding pelB as a signal peptide was arranged. Then, restriction enzyme sites were arranged between NcoI and EcoRI in order of NheI/SacII/SpeI. A nucleotide sequence encoding His×6 was arranged between SacII/SpeI. In addition, ampicillin resistant gene, T7 promoter, lac operator, and T7 terminator sequences were the same as that of pluck).

(3) The PCR product and the plasmid were cleaved by using a restriction enzyme in NcoI/NheI (each available from New England Biolabs) in accordance with a recommended method.

The solution of the plasmid cleaved with the restriction enzyme was subjected to spin column 400HR (Amasham Science).

(4) The solution of the PCR fragments cleaved with the restriction enzyme was purified by using a commercially available gel purification kit (SV Gel and PCR Clean-up system: Promega).

Figure 12A:
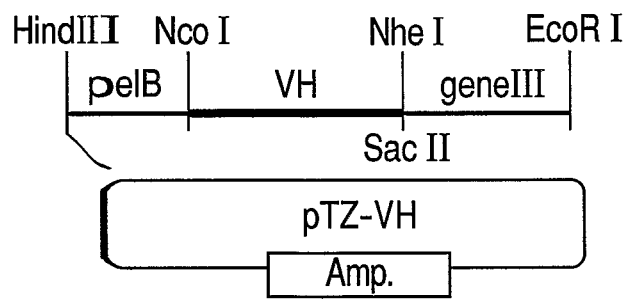
FIGS. 12A and 12B are schematic diagrams of a vector for illustrating Examples of the present invention.

(5) The above 2 fragments were mixed with a commercially available T4 ligase kit (Roche) in accordance with a method recommended by a supplier, followed by ligation. As a result, a VH coding gene insertion vector shown in FIG. 12A was obtained.

(6) *Escherichia coli* DS12S strain was transformed by using the ligation product through electropolation. A plasmid was prepared on a large scale.

(7) Those plasmid solutions were serially diluted, and each solution was subjected to transformation of *Escherichia coli* BL21 (DE3) through electropolation. 700 μL of LB medium were added to the solution, and the whole was cultured with shaking at 37° C. for 1 hour. The culture solution was centrifuged at 6,000 rpm for 5 minutes, and then 650 μL of the supernatant were discarded.

(8) The remaining supernatant and a precipitate fraction were suspended, and the suspension was inoculated on an LB/Amp. plate. Then, the whole was left standing at 37° C.

overnight. As a result, an antibody VH library containing about 5×10⁵ clones was eventually obtained.

(9) Next, 1,000 colonies were arbitrarily selected from the three 10³-fold dilution plates, and a protein crude extract was prepared according to the following steps. Each colony was subcultured in 3 mL of a liquid medium of LB/amp., and the whole was cultured with shaking at 28° C. for 6 hours. Next, IPTG was added to have a final concentration of 1 mM, and the whole was cultured with shaking for an additional 12 hours.

(10) Subsequently, a culture fraction and a supernatant bacterial fraction were obtained through centrifugation (10,500 rpm×5 min).

(11) The resultant bacterial fraction was added with and suspended in 200 μL of an osmotic solution cooled in ice (0.5 M sucrose, 1 M Tris-HCl (pH 8.0), 0.5 mM EDTA), and the whole was left standing in ice for 10 minutes. Next, 1 mL of cooled sterilized water was added, and the whole was left standing in ice for 1 hour. After the resultant had been centrifuged (6,000 rpm×30 min), the supernatant was placed in a dialysis bag (MWCO 10,000) and was dialyzed for 18 hours using Tris+0.1% Tween 20 solution (20 mM Tris, 500 mM NaCl) as an external solution while the external solution was changed every 6 hours.

The dialysis internal solution obtained in the above step was used as a sample for screening of a gold-binding antibody heavy chain variable region (VH).

Example 2

Screening of Gold-Binding Antibody Heavy Chain Variable Region (VH)

A 96-well titer plate on which gold (having a thickness of 100 nm) was deposited was prepared as a substrate for screening of a gold-binding antibody heavy chain variable region (VH). 250 μL of 1,000 sample solutions obtained in Example 1 were dispensed in each well, and the plate was gently shaken for 1 hour. After the supernatant had been discarded, the plate was turned upside down and was tapped on paper towel 10 times to remove water. A washing step was performed, which involved: adding 200 μL of Tris+0.1% Tween 20 to each well; and gently shaking the plate for 10 minutes. This operation was repeated 3 times. 200 μL of an antibody solution prepared by diluting an HRP-binding anti-His antibody (Invitrogen) with Tris+0.1% Tween 20 solution at 1:10,000 were dispensed in each well, and the plate was gently shaken for 1 hour. Subsequently, the same operation as the washing step was performed. 100 μL of each of an HRP substrate and Detect Reagents 1 and 2 (Amasham Science) serving as coloring materials were dispensed in each well, and the plate was gently shaken for 1 hour. The luminol chemiluminescence level was determined.

15 sample colonies in each of which chemiluminescence was observed as described above were subcultured in 1.5 mL of LB/amp., and the whole was cultured with shaking at 37° C. overnight. A plasmid was purified from the resultant fungus by means of an SV MiniPrep DNA purification system (Promega). DNA sequences of 17 VL-representing phagemids obtained as described above were determined according to the following method. Primers for sequencing were set at a pelB sequence portion placed upstream of the VH coding gene of an expression vector. The primer for sequencing was as follows. pelB-back (SEQ ID No: 88) 5'-ccgct ggatt gttat tactc gc-3'

A BigDye-PCR reaction was performed by using the above primer and a sequencing reaction kit and a reaction solution composition recommended by a supplier. A temperature cycle was 96° C.×3 min (94° C.×1 min→50° C.×1 min→68° C.×4 min)×30 cycle. Next, the base sequence of the PCR product purified through ethanol precipitation was determined by means of a sequencer (377 manufactured by ABI). As a result, each sequence of SEQ ID Nos.: 58 to 74 was obtained.

Example 3

Preparation of Antibody Light Chain Variable Region VL Library

A VL gene library was prepared from a Fab library of human peripheral blood cells in the same manner as in Example 1. The primers were as follows.

Back Primer back primer

```
                                             (SEQ ID No: 89)
5'-TCGCAACTGCGGCCCAGCCGGCCATGGCCGMCATYCAGWTGACCCAG
TCTCC-3'

(SEQ ID No: 90)
5'-TCGCAACTGCGGCCCAGCCGGCCATGGCCGATRTTGTGATGACYCAG
WCTCC-3'

(SEQ ID No: 91)
5'-TCGCAACTGCGGCCCAGCCGGCCATGGCCGAAATTGTGWTGACGCAG
TCTCC-3'

(SEQ ID No: 92)
5'-TCGCAACTGCGGCCCAGCCGGCCATGGCCGACATCGWGHTGACCCAG
TCTCC-3'
``` forward primer

```
                                             (SEQ ID No: 93)
5'-TTCTCGACTTGCGGCCGCACGTTTGATTTCCACCTT GGTCCC-3'

(SEQ ID No: 94)
5'-TTCTCGACTTGCGGCCGCACGTTTGATCTCCAGCTTGGTCCC-3'

(SEQ ID No: 95)
5'-TTCTCGACTTGCGGCCGCACGTTTGATATCCACTTT GCTCCC-3'

(SEQ ID No: 96)
5'-TTCTCGACTTGCGGCCGCACGTTTGATCTCCACCTT GGTCCC-3'

(SEQ ID No: 97)
5'-TTCTCGACTTGCGGCCGCACGTTTAATCTCCAGTCG TCTCCC-3'
```

In addition, a plasmid to be used was similarly prepared except that NheI between NcoI/SacII was changed to NotI at the time of preparation of a plasmid for protein expression in (2) of Example 1. Furthermore, the VL protein dialysis internal solution obtained at the end of the step of (11) of Example 1 was used as a sample for screening of a gold-binding antibody light chain variable region (VL).

Example 4

Screening of Gold-Binding Antibody Light Chain Variable Region (VL)

Screening of a gold-binding VL was performed in the same manner as in Example 2 except that the sample obtained in Example 3 was used as a screening sample. As a result, each sequence of SEQ ID Nos.: 75 to 77 was obtained.

Hereinafter, a phagemid was prepared from the human peripheral blood cell Fab gene library of Example 1, and a gold-binding VL or VH was screened.

Example 5

Screening of Gold-Philic VL-Representing Phage Group

A VL-representing phage library was prepared according to the following procedure and a phage group capable of binding to gold was selected.

(1) Phagemid for VL Representing

Figure 12B:
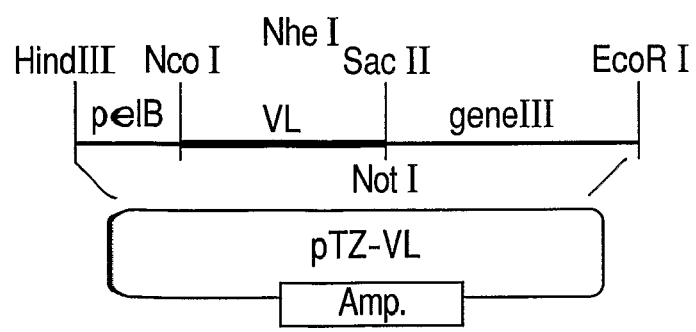

By using a Fab library derived from human adult peripheral blood B lymphocyte as a template, VL coding gene was replicated by means of the primers of SEQ ID Nos. 89 to 97. Furthermore, part of the N terminal of PIII protein serving as a coat protein of M13 phage was deleted, and a library of VL-representing phagemid (FIG. 12B) prepared in such a manner that VL protein was fused and expressed was used (Biochem Biophys Res Commun. 1996, 218, pp 682)

(2) Preparation of VL Fragment Representing Phage Library

1) Transformation

1 µL of the VL coding gene library (350 ng/µL) was transformed into 40 µL of *Escherichia coli* DH 12S through electropolation (applied voltage: 1.5 KV, resistance: 186Ω, capacity: 50 µF). Next, a VL-representing phage library was prepared according to the following procedure.

2) Culture (i) 800 µL of LB medium were added to the DH12S solution after the transformation, and the whole was cultured with shaking at 37° C. for 1 hour (140 rpm).

(ii) 20 mL of the culture solution were added to LB medium+ampicillin having a final concentration of 100 µg/mL (LB/amp.), and the whole was cultured at 37° C. for 3 to 4 hours.

(iii) 40 µL of M13KO7 as a helper phage were added, and the whole was cultured with shaking at 100 rpm for an additional one hour.

(iv) A 50 mg/mL kanamycin solution was added to have a final concentration of 50 µg/mL, and the whole was cultured with shaking at 37° C. (100 rpm).

3) Collection of VL-Representing Phage Library (i) 5 mL of a 20% PEG/500 mM NaCl were added to the culture solution, and the whole was left standing in ice for one or more hours.

(ii) The supernatant was carefully removed through centrifugation (6,500 rpm×35 min).

(iii) The precipitate was suspended in 500 µL of PBS buffer to prepare a VL-representing phage solution.

4) Titer Evaluation of VL-Representing Phage Library (i) 10 µL of JM109 glycerol stock were added to LB, and the whole was cultured with shaking at 37° C.

(ii) The VL-representing phage solution prepared in 3) was serially diluted with LB medium.

(iii) 10 µL of the serially diluted ($\times 10^{-6}$ to $10^{-10}$) solution were added to 750 µL of (a) the culture solution having an $OD_{600}$ of about 0.5, and the whole was cultured with shaking at 37° C. for 1 hour.

(iv) Centrifugation (6,000 rpm×5 min) was performed to remove 700 µL of the culture supernatant.

(v) The remaining culture supernatant and a precipitate were suspended by pipetting. Then, the suspension was inoculated on an LB/amp. plate, and the whole was left standing at 37° C. overnight.

(vi) The number of colonies emerged on a diluted concentration plate having 100 or less colonies was counted and defined as a titer value of the VL-representing phage library.

The resultant VL-representing phage library solution: $5 \times 10^9$ cfu/µL (3) VL Panning Using Gold Fine Particles The phage library solution prepared as described above and gold fine particles (1.5 µmΦ: manufactured by Sigma-Aldrich) were used to repeat a panning operation according to the following method 5 rounds for the purpose of selecting a phage group representing a gold-binding VL.

1) Binding Experiment (i) 10 µL of a solution of the gold fine particles (50 mg/PBS 1 ml) and PBS+0.1% Tween 20 (PBST) were added to the phage solution (in a volume such that the total number of phages in the solution is 1,010 cfu) in a sterilized Eppendorf tube (1.5 mL) in such a manner that the total volume would be 1,000 µL, and the resultant was prepared as a binding reaction solution.

(ii) The binding reaction solution was maintained for 30 minutes while being gently rotated at room temperature.

(iii) The resultant obtained in (ii) was centrifuged (10,000 rpm×5 min), and the solution supernatant was carefully discarded.

2) Washing (Washing of Non-Specific Adsorbate)

(i) 500 µL of PBST were added to the gold fine particles in the Eppendorf tube, and the whole was maintained for 10 minutes while being gently rotated at room temperature.

(ii) Centrifugation (10,000 rpm×5 min) was performed, and the washing supernatant was carefully removed.

(iii) Each of the above (i) and (ii) was repeated 10 times.

3) Acid Elution and Titer Evaluation of Acid Eluted Fraction

The phage titer adsorbed to the gold fine particles obtained in 2) was evaluated according to the following procedure.

3)-1 Acid Elution (i) 115 µL of 0.2 M Gly-HCl (pH 2.2) were added to the gold fine particles after the washing, and the whole was maintained for 1 min while being rotated vertically.

(ii) Centrifugation (10,000 rpm×5 min) was performed, and the supernatant was collected as an acid eluted fraction.

(iii) The collected acid eluted fraction was neutralized by adding 15 µL of 1 M Tris-HCl.

(iv) 1 µL of the acid eluted solution after the neutralization was serially diluted, and a titer value was measured according to the titer evaluation method.

(v) The remaining acid eluted fraction was quickly mixed with a fraction of gold fine particles, and the mixture was suspended again.

3)-2 Titer Evaluation

Titer evaluation was performed in the same manner as in (2)-3), 4) to obtain the following results.

1st round: $9.8 \times 10^2$ cfu

2nd round: $1.0 \times 10^3$ cfu

3rd round: $7.8 \times 10^2$ cfu

4th round: $1.3 \times 10^3$ cfu

5th round: $1.1 \times 10^4$ cfu

4) Reinfection and Phage Amplification

Up to a fourth round, the phage group adsorbed to the gold fine particles obtained in 3) was reinfected with *Escherichia coli* to amplify the number of phages for preparing a phage solution for subsequent panning.

(i) *Escherichia coli* JM109 was cultured with shaking at 37° C. (140 rpm) in 20 mL of LB medium for reinfection and phage amplification.

(ii) The suspension of the gold fine particles obtained in 3) was added to the *Escherichia coli* culture solution in (a) having an $OD_{600}$ in the range of 0.3 to 0.5, and the whole was cultured with shaking at 37° C. for 1 hour (140 rpm).

(iii) Ampicillin was added to have a final concentration of 100 μg/mL, and the whole was cultured with shaking at 37° C. for 2 hours.

(iv) 40 μL of helper phage M13KO7 were added, and the whole was cultured at 37° C. for 1 hour while a shaking speed was reduced to 100 rpm.

(v) Kanamycin was added to have a final concentration of 50 μg/mL, and the whole was cultured with shaking at 37° C. overnight.

(vi) A phage in the culture supernatant was collected by the same operation as those of (2)-3), 4) to prepare a phage solution. Furthermore, the phage solution was evaluated for titer values to confirm that the phage was amplified.

The titer values obtained after amplification are shown below.

1st round: $2.4 \times 10^9$ cfu

2nd round: $8.1 \times 10^8$ cfu

3rd round: $1.8 \times 10^9$ cfu

4th round: $1.1 \times 10^1$ cfu (4) Phage ELISA

1) Preparation of Gold-Deposited Substrate for ELISA

The same 96-well titer plate (BD, polystyrene) on which gold (having a thickness of 100 nm) was deposited as that of Example 2 was used as a substrate for a phage ELISA.

2) Preparation of VL-Representing Phage Monoclone

A phagemid was collected from 11 colonies expressing on a $10^4$-fold diluted plate in the titer evaluation on a fifth round in (3)-4) according to the following procedure.

(i) Each colony was cultured at 37° C. with 20 mL of LB/amp.

(ii) 40 μL of helper phage M13KO7 were added, and the whole was cultured at 37° C. for 1 hour while a shaking speed was reduced to 100 rpm.

(iii) Kanamycin was added to have a final concentration of 50 μg/mL, and the whole was cultured with shaking at 37° C. overnight.

(iv) A phage in the culture supernatant was collected by the same operation as those of (2)-3), 4) to prepare a phage solution. Furthermore, the phage solution was evaluated for titer value to confirm that the phage was amplified.

Titer values obtained after amplification are shown below.

No. 1: $3.8 \times 10^9$ cfu

No. 2: $9.0 \times 10^8$ cfu

No. 3: $2.4 \times 10^9$ cfu

No. 4: $1.0 \times 10^9$ cfu

No. 5: $9.7 \times 10^7$ cfu

No. 6: $4.4 \times 10^8$ cfu

No. 7: $6.2 \times 10^9$ cfu

No. 8: $8.9 \times 10^7$ cfu

No. 9: $1.4 \times 10^9$ cfu

No. 10: $1.1 \times 10^{10}$ cfu

No. 11: $4.9 \times 10^9$ cfu

3) Preparation of Phage Solution

Each phage solution obtained in 2) was used to prepare 200 μL of each of dilution series in which the titer value was sequentially reduced from $10^9$ cfu by a factor of 10 according to the following composition.

VL-representing phage solution: x μL

Super blocking buffer (PIERCE): 20 μL 0.5% Tween 20/PBS: x/5 μL

PBS: 180–(6x/5) μL

4) ELISA (i) 80 μL of each of the serially-diluted VL-representing phage solutions were dispensed in a gold-deposited titer plate, and the plate was gently shaken for 1 hour in a shaker.

(ii) The phage solution was removed, 90 μL of PBST were dispensed in each well, and the whole was stirred for 10 minutes, followed by removing the washing supernatant. This operation was repeated 3 times.

(iii) 75 μl of a solution of HRP-Anti M13 immunoglobulin/SBB/PBS (1/1,000:1:10) were dispensed in each well, and the plate was gently shaken for 1 hour in a shaker.

(iv) The supernatant of the immunoglobulin solution was discarded. Next, PBST was dispensed in a volume of 90 μL/well, and the whole was stirred for 10 min. This washing operation was repeated 3 times.

(v) Each of detection reagents 1 and 2 (Amasham BIOSCIENCE) was dispensed in a volume of 35 μL/well, and the whole was allowed to react while being gently stirred for 1 min.

(vi) The luminescence intensity of luminol was measured. No. 1, No. 2, and No. 3 having high luminescence intensities were provided as gold-binding VL-representing phage clones.

Phagemids were isolated from the above four phage clones to elucidate the base and amino acid sequences of a gold-binding VL. Next, an expression vector was prepared to express a protein, thereby confirming binding affinity on a surface plasmon resonance (SPR) gold substrate.

Example 6

Acquisition of Gold-Philic VL Protein (1) Collection of Phagemid

A phagemid was collected from the colony corresponding to No. 7 expressing on a $10^4$-fold diluted plate in the titer evaluation on the fifth round in (3)-4) of Example 5 according to the following procedure.

(i) Each colony was cultured at 37° C. overnight with 1.6 mL of LB/amp.

(ii) A phagemid was collected in accordance with a method recommended by a supplier by using a MiniPrep SV plus DNA Purification system (promega)

(2) Preparation of Expression Vector

Figure 13:
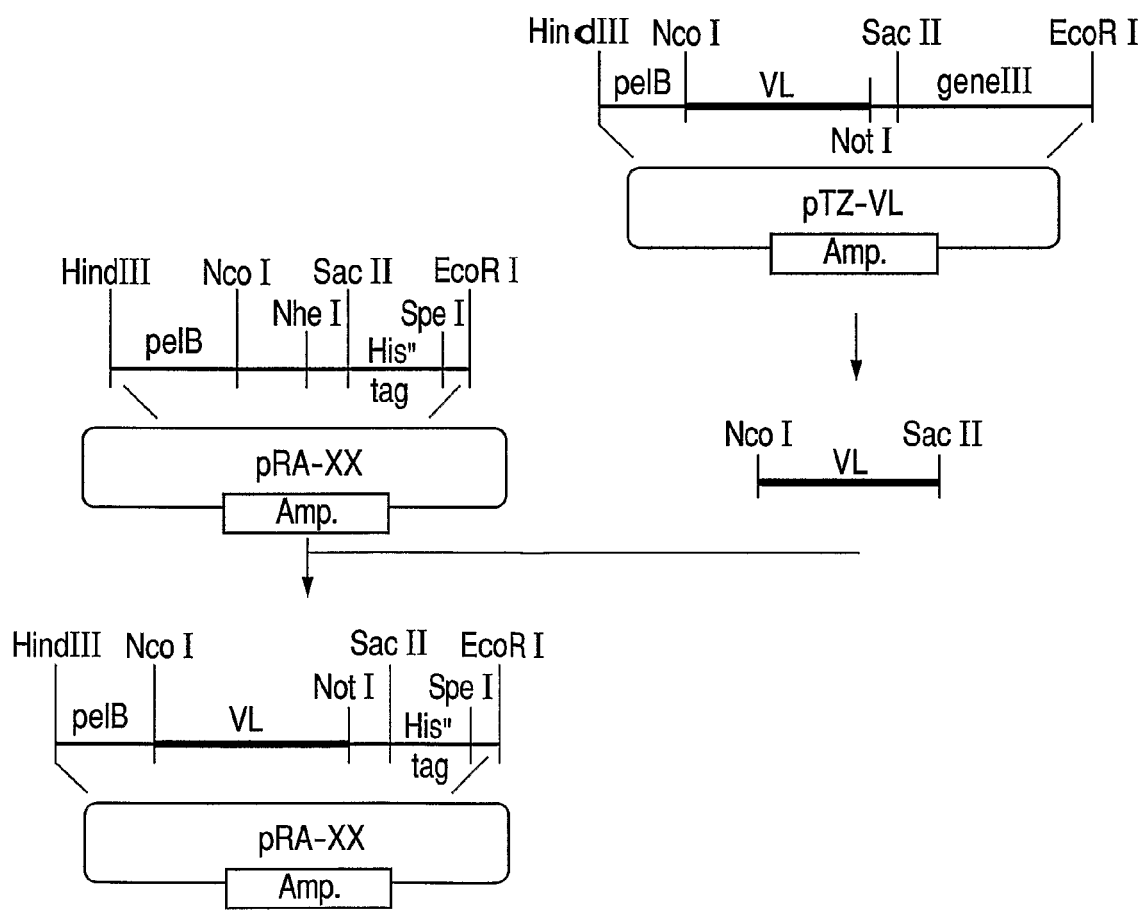
FIG. 13 is a schematic diagram of a vector for illustrating Examples of the present invention.

Expression vectors expressing the above 3 kinds of VL proteins were constructed according to the following configurations. pRA-XX shown in FIG. 11 of Example 1 and the phagemid obtained in (1) were cleaved through a restriction enzyme reaction by using NcoI and NotI of each of them. The resultant VL fragment was inserted into pRA-XX to prepare a plasmid pRA-VLNo, n (n: clone number) expressing VL code nucleic acid as a fusion protein (FIG. 13).

(3) Expression and Purification of Protein 3 vectors for expressing VL proteins obtained as described above were used to express VL proteins.

1) Transformation

The above expression vectors were used to transform 40 µL of BL21 (DE3) competent cell. The transformation was performed under such a condition that heat shock was performed in ice→42° C.×90 sec→in ice. 750 µL of LB medium were added to the BL21 solution transformed by heat shock, and the whole was cultured with shaking for 1 hour at 37° C. After that, centrifugation was performed at 6,000 rpm×5 min, and 650 µL of the culture supernatant were discarded. The remaining culture supernatant and a cell fraction as a precipitate were stirred and inoculated on an LB/amp. plate, and the whole was left standing at 37° C. overnight.

2) Preculture

A colony on the plate was selected at random and was cultured with shaking at 28° C. overnight in 3.0 mL of an LB/amp. medium.

3) Main Culture

The preculture solution was subcultured in 750 ML of a 2×YT medium, and the culture was continued at 28° C. When $OD_{600}$ exceeded 0.8, IPTG was added to have a final concentration of 1 mM, and culture was further performed at 28° C. overnight.

4) Purification (i) Ammonium Sulfate Precipitation

The culture solution obtained in 3) was centrifuged at 6,000 rpm×30 min to obtain a culture supernatant. The weight of the resultant culture supernatant was measured Then, ammonium sulfate in a weight of 60% of the weight of the culture supernatant was gradually added. Then, the resultant was stirred at 4° C. overnight.

(ii) Desalting

The solution obtained in (i) was centrifuged at 8,000 rpm× 20 min, and the supernatant was discarded. The resultant precipitate was added with and immersed in 15 mL of 20 mM Tris/500 mM NaCl (hereinafter, referred to as a Tris solution) at 4° C. overnight for dissolution. Next, the resultant solution was charged into a cellulose tube for dialysis (manufactured by Sanko Junyaku Co., Ltd.) and was dialyzed at 4° C. by using the Tris solution as an external solution for desalting (the external solution was changed every 6 hours)

(iii) Metal Chelate Column

A His-Bind (manufactured by Novagen) was used as a metal chelate column carrier. Column adjustment, sample loading, and a washing step were performed at 4° C. in accordance with the method recommended by the supplier. Elution of a His tag-fused VL protein as a target was performed with a 500 mM imidazole/Tris solution.

SDS-PAGE (acrylamide 15%) of the eluent confirmed that the eluent had a single band and was purified. The eluent was dialyzed again by using the Tris solution as an external solution to remove imidazole in the eluent. Furthermore, buffer substitution was performed by changing the external solution to a phosphate buffer (hereinafter, referred to as PBS) to prepare a VL protein solution for SPR.

Example 7

SPR Measurement

The binding affinity of the VL protein obtained in Example 6 for gold was measured by means of SPR. A BIAcore 2000 (manufactured by BIAcore) was used as an SPR measuring device. A gold-deposited glass substrate SIA-kit Au of the same company was used as a gold substrate to which the protein was to be bound.

Measurement was performed under the following conditions.

Figure 9:
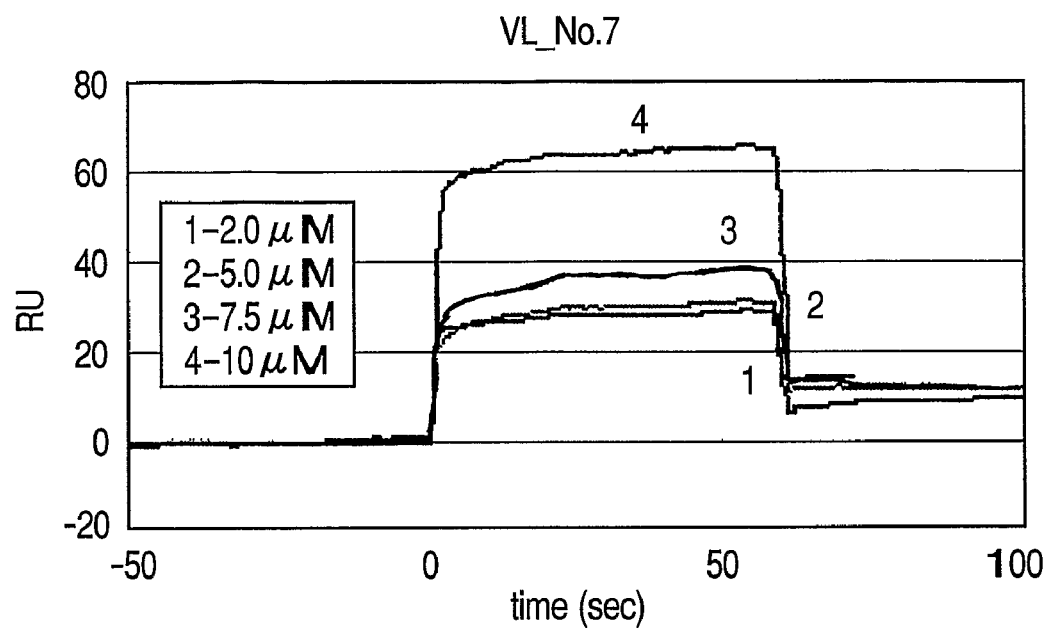
FIG. 9 is a diagram showing an example of the SPR evaluation of VL obtained by the present invention.

Running buffer: PBST
Temperature: 25° C.
Flow rate: 20 µL/min
Sample: VL protein/PBST
Injection amount: 20 µL A binding curve in which the binding affinity was confirmed was obtained (FIG. 9).

Example 8

Determination of Base and Amino Acid Sequences of VL Protein

The DNA sequence of the VL No, 7 obtained as described above was determined in accordance with the following method.

A primer for sequencing was set at a pelB sequence portion placed upstream of the VL coding gene. The primer for sequencing was as follows. pelB-back (SEQ ID No: 88)

5'-ccgct ggatt gttat tactc gc-3'

A BigDye-PCR reaction was performed by using the above primer in the same manner as in Example 2 and a sequencing reaction kit and a reaction solution composition recommended by a supplier. A temperature cycle was 96° C.×3 min→(94° C.×1 min→50° C.×1 min 68° C.×4 min)×30 cycle 4° C. Next, the base sequence of the PCR product purified through ethanol precipitation was determined by means of a sequencer (377 manufactured by ABI). The following result was obtained. No. 7 had the same base sequence as that of SEQ ID No: 76 of Example 12.

Example 9

Screening of Gold-Philic VH-Representing Phage Group

A VH-representing phage library was prepared according to the following procedure to select a phage group having a binding affinity for gold.

(1) Phagemid for Representing VH

A Fab library derived from human adult peripheral blood B lymphocyte was used as a template in the same manner as in Example 1, and the primers of SEQ ID Nos. 80 to 89 were used in the same manner as in Example 1. Thus, VH coding gene was replicated. Furthermore, part of the N terminal of PIII protein serving as a coat protein of M13 phage was deleted, and a library of VH-representing phagemid (FIG. 12A) prepared in such a manner that VH protein was fused and expressed was used.

(2) Preparation of VH-Representing Phage Library

A VH-representing phage library was prepared in the same manner as in (2) of Example 5 except that the product obtained in (1) was used. The resultant VH-representing phage library solution: $1\times10^9$ cfu/µL.

(3) VH Panning Using Gold Fine Particles

Panning for selecting a phage group representing a gold-binding VH was performed in the same manner as in (3) of Example 5 except that the phage library solution prepared in (2) above was used.

1) Binding Experiment

Hereinafter, 2) Washing and 3) Acid elution and titer evaluation similar to those of Example 5 were performed.

1st round: $9.8\times10^2$ cfu

2nd round: $1.0\times10^3$ cfu

3rd round: $7.8\times10^2$ cfu

4) Reinfection and Phage Amplification

Reinfection and phage amplification were performed in the same manner as in Example 5. Titer values obtained after amplification are shown below.

1st round: $2.4\times10^9$ cfu

2nd round: $8.1\times10^8$ cfu (4) Phage ELISA

1) Preparation of Gold-Deposited Substrate for ELISA

The same substrate as that of Example 5 was used as a substrate for phage ELISA.

2) Preparation of VL-Representing Phage Monoclone

A phagemid was collected from 20 colonies expressing on a $10^4$-fold diluted plate in the titer evaluation on a third round in the VH panning operation in the same manner as in Example 1. The titer values of the resultant VH-representing phage monoclone solutions are shown below.

No. 1: $3.8\times10^9$ cfu

No. 2: $9.0\times10^8$ cfu

No. 3: $2.4\times10^9$ cfu

No. 4: $1.0\times10^9$ cfu

No. 5: $9.7\times10^7$ cfu

No. 6: $4.4\times10^8$ cfu

No. 7: $6.2\times10^9$ cfu

No. 8: $8.9\times10^7$ cfu

No. 9: $1.4\times10^9$ cfu

No. 10: $1.1\times10^{10}$ cfu

No. 11: $4.9\times10^9$ cfu

No. 12: $9.0\times10^8$ cfu

No. 13: $2.4\times10^9$ cfu

No. 14: $1.0\times10^9$ cfu

No. 15: $9.7\times10^7$ cfu

No. 16: $4.4\times10^8$ cfu

No. 17: $6.2\times10^9$ cfu

No. 18: $8.9\times10^7$ cfu

No. 19: $1.4\times10^9$ cfu

No. 20: $1.1\times10^{10}$ cfu

3) Preparation of Phage Solution

Each phage solution obtained in 2) was used to prepare 200 µL of each of dilution series in which the titer value was sequentially reduced from $10^9$ cfu by a factor of 10 according to the following composition.

VL-representing phage solution: x µL

Soluble VL solution (50 ng): x µL

Super blocking buffer (PIERCE): 20 µL 0.5% Tween 20/PBS: x/5 µL

PBS: 179−(6x/5) µL

4) Phage ELISA

Phage ELISA was performed by the same operation as that of Example 1 Three clones each having a luminescence intensity higher than that of a VH library solution for comparison were provided as gold-binding VH-representing phage clones (Nos. 2, 4, and 6).

Example 10

Acquisition of Gold-Philic VH Protein

Phagemids were isolated from the above three phage clones, and then their expression vectors were prepared to express a protein, thereby confirming binding affinity on a surface plasmon resonance (SPR) gold substrate. Furthermore, the base and amino acid sequences of each of those gold-binding VH were elucidated.

(1) Collection of Phagemid

A phagemid was collected from the colony corresponding to 15 clones expressing on a $10^4$-fold diluted plate in the titer evaluation on the third round according to the following procedure.

(a) Each colony was cultured at 37° C. overnight in 1.6 mL of LB/amp.

(b) A phagemid was collected in accordance with a method recommended by a supplier by using a MiniPreps SV plus DNA Purification system (promega)

(2) Preparation of Expression Vector

Figure 14:
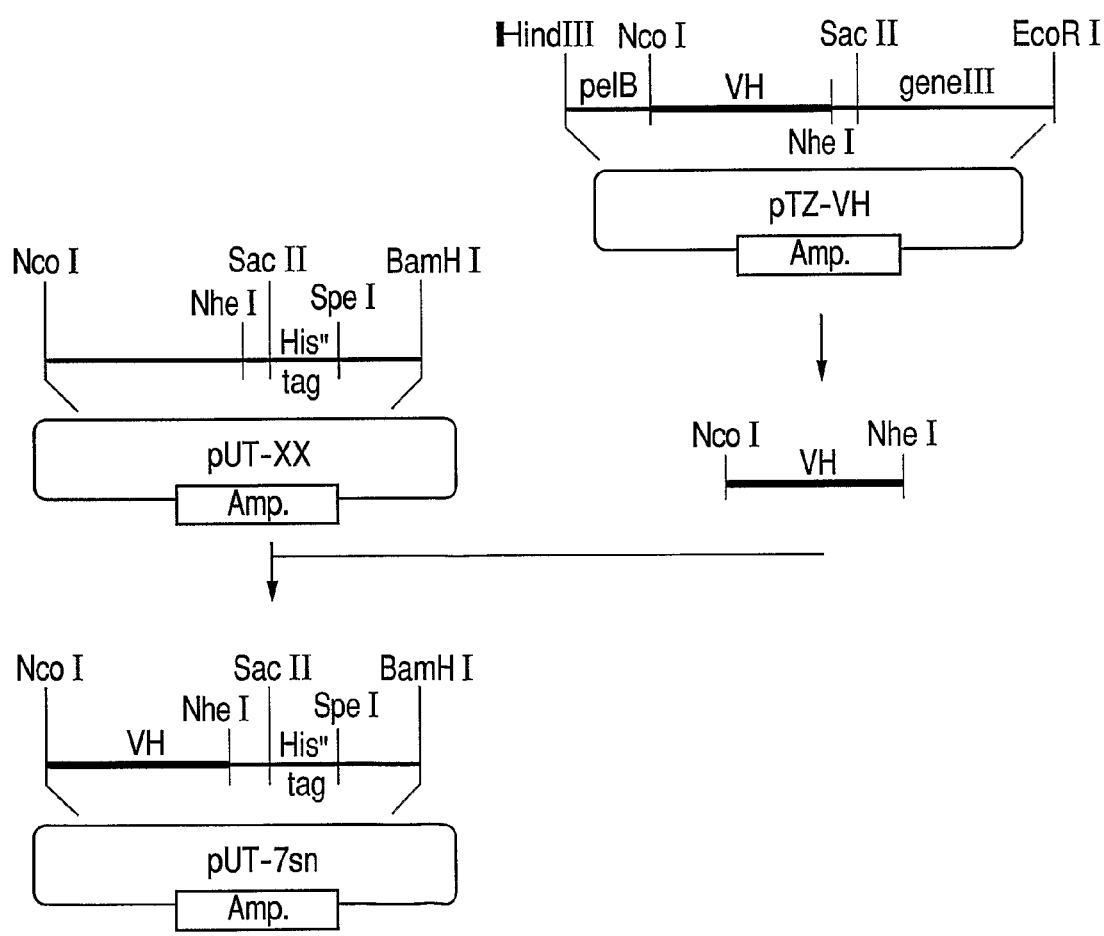
FIG. 14 is a schematic diagram of a vector for illustrating Examples of the present invention.

Expression vectors expressing the above 3 kinds of VL proteins were constructed according to the following configurations.

pUT-XX was prepared by changing a multicloning site of PET-15b (Novagen). The pUT-XX and the phagemid obtained in (1) above were cleaved through a restriction enzyme reaction by using NcoI and NotI of each of them. The resultant VH fragment was inserted into pUT-XX to prepare a plasmid pRA-7sn (n: phage clone number described above) expressing VH coding nucleic acid as a fusion protein (FIG. 14).

(3) Expression and Purification of Protein 3 kinds of VHs (7s2, 7s4, and 7s6) were acquired by performing the above procedure (treating the expression vectors in the step of protein expression and purification described below in an individual system).

1) Transformation

The above 2 expression vectors were used to transform 40 µL of different BL21 (DE3) competent cell solutions. The transformation was performed under such a condition that heat shock was performed in ice→42° C.×90 sec→in ice. 750 µL of LB medium were added to the BL21 solution transformed by heat shock, and the whole was cultured with shaking for 1 hour at 37° C. After that, centrifugation was performed at 6,000 rpm×5 min, and 650 µL of the culture supernatant were discarded. The remaining culture supernatant and a cell fraction as a precipitate were stirred and inoculated on an LB/amp. plate, and the whole was left standing at 37° C. overnight.

2) Preculture

A colony on the plate was selected at random and was cultured with shaking at 28° C. overnight with 3.0 mL of an LB/amp. medium.

3) Main Culture

The preculture solution was subcultured in 750 ML of a 2×YT medium, and the culture was further continued at 28° C. When $OD_{600}$ exceeded 0.8, IPTG was added to have a final concentration of 1 mM, and culture was performed at 28° C. overnight.

4) Purification

A target polypeptide chain was purified from an insoluble granule fraction through the following steps.

(i) Collection of Insoluble Granule

The culture solution obtained in 3) above was centrifuged at 6,000 rpm×30 min to obtain a precipitate as a bacterial fraction. The resultant was suspended in a Tris solution (20 mM Tris/500 mM NaCl) in ice. The resultant suspension was homogenized with a French press to obtain a homogenized solution. Next, the homogenized solution was centrifuged at 12,000 mm×15 min, and the supernatant was removed to obtain a precipitate as an insoluble granule fraction.

(ii) Solubilization of Insoluble Granule Fraction

The insoluble fraction obtained in (i) was added with and immersed overnight in 10 mL of a 6 M guanidine hydrochloride/Tris solution. Next, the resultant was centrifuged at 12,000 rpm×10 min to obtain a supernatant as a solubilized solution.

(iii) Metal Chelate Column

A His-Bind (manufactured by NovagEn) was used as a metal chelate column carrier. Column adjustment, sample loading, and a washing step were performed at room temperature (20° C.) in accordance with the method recommended by the supplier. Elution of a His tag-fused VL polypeptide as a target was performed in a 60 mM imidazole/Tris solution. SDS-PAGE (acrylamide 15%) of the eluent confirmed that the eluent had a single band and was purified.

(iv) Dialysis

The eluent was dialyzed by using a 6 M guanidine hydrochloride/Tris solution as an external solution at 4° C. to remove imidazole in the eluent, thereby obtaining the above polypeptide chain solutions.

(v) Refolding

In the same manner as that described above, the polypeptide chain solutions of VHg-VLh and VHh-VLg were separately dialyzed according to the following steps for removing guanidine hydrochloride (4° C.) to perform refolding of a protein.

a) A sample having a concentration of 7.5 µM (volume after dilution of 10 ml) was prepared by using a 6 M guanidine hydrochloride/Tris solution on the basis of the molar absorbance coefficient and ΔO.D. (280 nm-320 nm) level of each polypeptide chair. Next, β-mercaptoethanol (reductant) was added to have a final concentration of 375 µM (50-fold protein concentration) for reduction at room temperature in a dark room for 4 hours. The sample solution was charged into a dialysis bag (MWCO: 14,000) and provided as a sample for dialysis.

b) The sample for dialysis was immersed in a 6 M guanidine hydrochloride/Tris solution as an external solution, and was dialyzed for 6 hours while being gently stirred.

c) The concentration of the guanidine hydrochloride solution of the external solution was reduced to 3 M and then to 2 M in a stepwise manner. The sample was dialyzed at each concentration of the external solution for 6 hours.

d) The Tris solution was added with oxidized glutathione (GSSG) to have a final concentration of 375 µM and with L-Arg to have a final concentration of 0.4 M), and then was added with the 2 M dialysis external solution in 3) above to have a guanidine hydrochloride concentration of 1 M. The sample was dialyzed in the external solution whose pH had been adjusted to 8.0 (4° C.) with NaOH for 12 hours while being gently stirred.

e) An L-Arg Tris solution having a guanidine hydrochloride concentration of 0.5 M was prepared by the same operation as that of d), and dialysis was performed for an additional 12 hours.

f) Finally, dialysis was performed for 12 hours in a Tris solution. After the completion of the dialysis 7), centrifugation was performed at 10,000 rpm for about 20 min to separate an aggregate and a supernatant.

The 3 kinds of VH solutions obtained as described above were subjected to buffer substitution by changing the external solution to a phosphate buffer (hereinafter, referred to as PBS) to prepare VH protein solution for SPR.

Example 11

SPR Measurement

Figure 10:
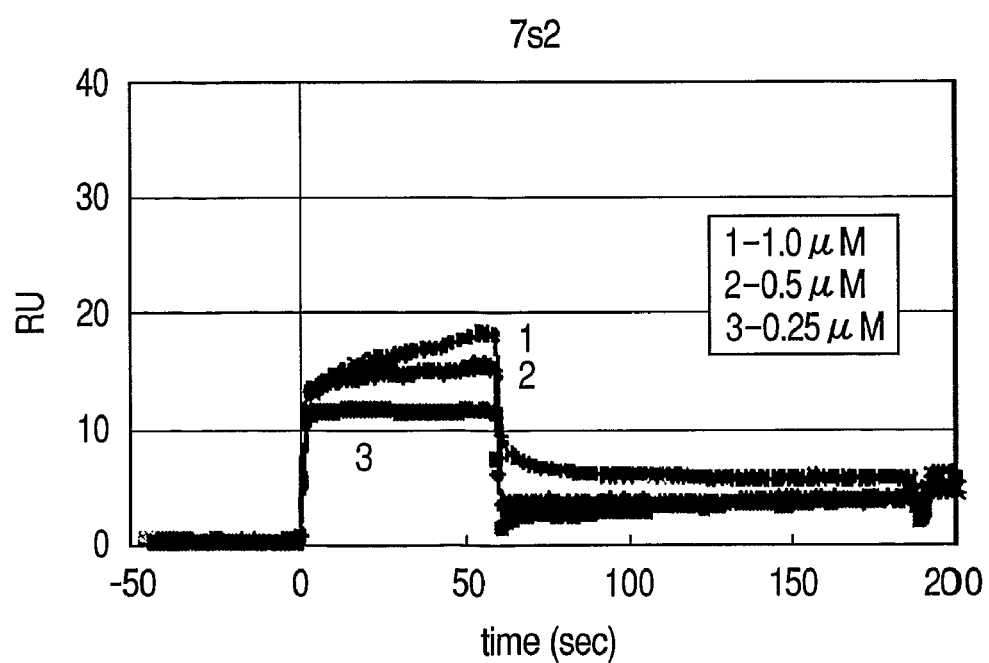
FIG. 10 is a diagram showing an example of the SPR evaluation of VH obtained by the present invention.

The binding affinity of the VH protein obtained in Example 10 for gold was measured by means of SPR in the same manner as in Example 7. A binding curve in which the binding affinity was confirmed was obtained for each of 7s2, 7s4, and 7s6. FIG. 10 shows the representative examples). The following $K_D$'s were obtained by curve fitting.

7s2: $K_D=5.0\times10$ $M^{-8}$

7s4: $K_D=8.0\times10$ $M^{-9}$

7s6: $K_D=3.0\times10$ $M^{-7}$

Example 12

Determination of Base and Amino Acid Sequences of VH Protein

The DNA sequence of each of the three VH-representing phagemids obtained as described above was determined in the same manner as in Example 2. A primer for sequencing was set at a pelB sequence portion placed upstream of the VH coding gene. The primer for sequencing as that of Example 2 was used, and analysis was performed according to the same procedure to obtain three different sequences. Those sequences obtained in Example 10 corresponded to SEQ ID Nos.: 59 to 61.

Example 13

Gold-Binding Experiment on VH/VL Composite by Means of SPR

Figure 3:
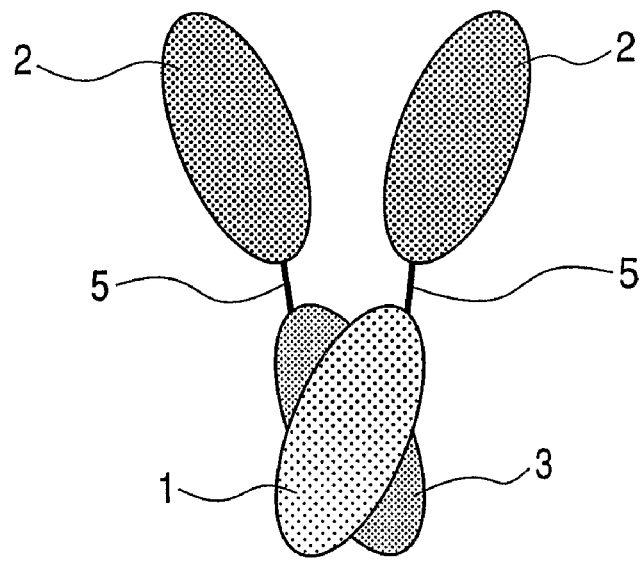
FIG. 3 is a diagram schematically showing the constitution of a structure in an example of a complex protein according to the present invention.
Figure 4A:
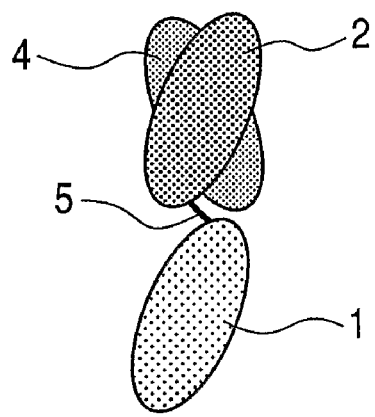
FIGS. 4A and 4B are, respectively, a diagram schematically showing the constitution of a structure in an example of a complex protein according to the present invention.
Figure 4B:
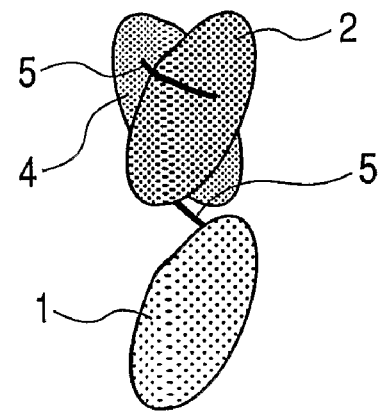

A PBST solution containing 50 nM of each of the VL clone No. 7 obtained in Example 6 and the VH clone: 7s2 obtained in Example 10 was prepared and preserved at 4° C. for one day. SPR measurement was performed by using the mixed solution in the same manner as in Example 7. As a result, binding affinity for gold was confirmed at a lower concentration than that of Example 7 or Example 11. This result suggests that mixing of the clones forms a complex (Fv) to increase binding affinity owing to its stabilized structure (FIG. 3).

Example 14

Acquisition of Gold-Binding scFv

An scFv composed of the VL clone: No. 7 obtained in Example 6 and the VH clone: 7s2 obtained in Example 10 was prepared according to the following procedure.

(1) Preparation of Expression Vector

An expression vector which could express a fusion protein, which could be continuously translated from VL (No. 7) coding gene, linker (GGGGS)×3, VH (7s4) coding gene, and His×6 (hereinafter, referred to as His tag).

Figure 15:
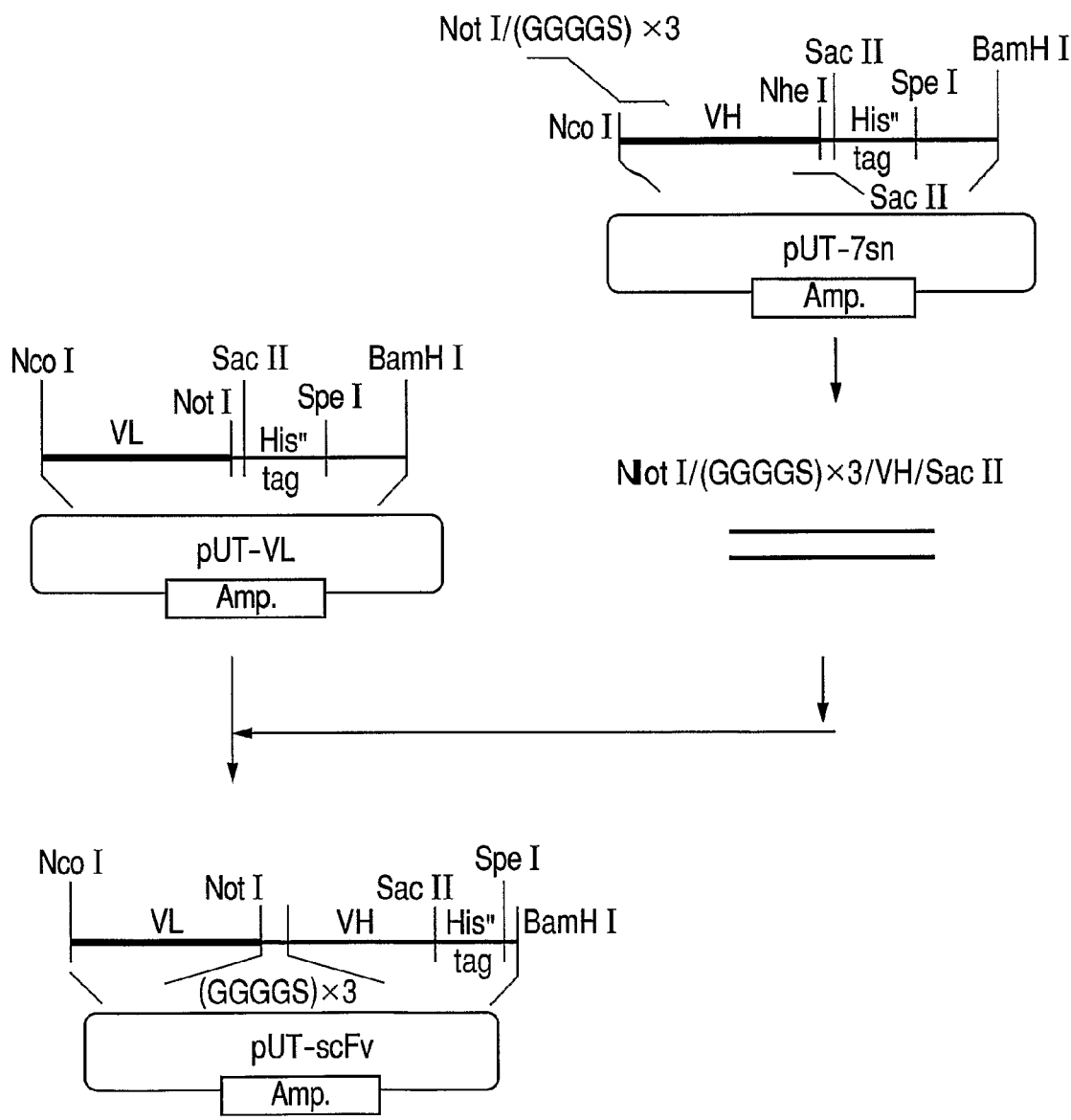
FIG. 15 is a schematic diagram of a vector for illustrating Examples of the present invention.

A specific preparation method is shown in FIG. 15.

The following primers were used.

```
scFv-B
                                         (SEQ ID No: 117)
5'-NNNNNCCATGGCCGGGGGCGGGGGCAGCGGGGGCGGGGCAGCGGGG
GCGGGGCAGCCAGGTGCAGTTGGTGGAGTCT-3' scFv-F
                                         (SEQ ID No: 118)
5'-NNNNNCCGCGGAACCATTCAGATCCTCTTCT-3'
```

(2) Expression and Purification of Protein

Hereinafter, the vector for expressing an scFv protein obtained as described above was used to express and purify an scFv protein.

1) Protein Expression

The above expression vector was used to transform *Escherichia coli* BL21 (DE3), and culture was performed by using a 2xYT medium at 28° C. Expression was induced with IPTG having a final concentration of 1 mM at $O.D._{600}$=about 0.8, and the resultant was cultured with shaking overnight. The bacterial body was centrifuged at 6,000 rpm×20 min to obtain a culture supernatant fraction and a bacterial fraction. Those samples were electrophoresed according to a conventionally known method by means of SDS-PAGE to confirm the expression amount of a target protein. The result showed that secretion into the culture supernatant fraction was extremely small. In view of the above, in order to purify the target protein from the bacterial fraction, a sample was prepared according to the following procedure. First, the bacterial body was resuspended in 15 mL of PBS, the suspension was further added with 25 mL of PBS, and the mixture was homogenized by means of a French press. The resultant homogenized solution was centrifuged at 12,000 rpm×15 min to obtain a precipitate fraction as insoluble granules. The resultant insoluble granules were immersed in a 6 M guanidine hydrochloride/Tris solution overnight and solubilized to obtain a sample for metal chelate column.

2) Purification by Metal Chelate Column

A 6 M guanidine hydrochloride/5 mM imidazole/Tris solution was used as a running buffer, and purification was performed in the same manner as in Example 2 except that: the imidazole concentration at the time of elution was set to 100 mM; and a developing temperature was set at room temperature (20° C.)

3) Dialysis

The eluted fraction obtained in 2) was charged into a cellulose tube for dialysis (manufactured by Sanko Junyaku Co., Ltd.) and was dialyzed at 4° C. by using a 6 M guanidine hydrochloride/1 mM EDTA/Tris solution as an external solution (the external solution was changed every 6 hours).

4) Reconstruction of Protein

An scFv solution obtained in 3) was adjusted with Tris solution to 7.5 µM to be provided as a sample. An scFv structure was reconstructed while the guanidine hydrochloride concentration gradually in the internal solution was reduced by reducing the glycin hydrochloride concentration in the external solution with respect to the above solution.

(a) A sample having a concentration of 7.5 µM of a molar absorbance coefficient and of an O.D. (280 nm) estimated from the amino acid sequence of the target protein was prepared by using a 6 M guanidine hydrochloride/Tris solution.

(b) Next, β-mercaptoethanol (reductant) was added to have a final concentration of 375 µM, followed by reduction at room temperature in a dark room for 4 hours.

(c) The sample was charged into the same dialysis bag as that described above, and the whole was placed in an external solution (a 6 M guanidine hydrochloride/Tris solution) and dialyzed at 4° C. for about 6 hours.

(d) The external solution was changed twice thereafter every 6 hours. At the time of such change, the sample was dialyzed while the concentration of the guanidine hydrochloride solution of the external solution was reduced to 3 M and then to 2 M in a stepwise manner.

(e) Next, the Tris solution was added with oxidized glutathione (GSSG) to have a final concentration of 375 µM and with L-Arg to have a final concentration of 0.4 M), and then was added with the dialysis external solution (2 M) in (d) above to have a guanidine hydrochloride concentration of 1 M. The sample was dialyzed in an external solution whose pH had been adjusted to 8.0 (at 4° C.) with NaOH for about 12 hours.

(f) A 0.5 M guanidine hydrochloride/Tris solution was prepared by the same operation as that of (e), and dialysis was performed at 4° C. for about 12 hours.

(g) Finally, dialysis was performed 4° C. for about 12 hours while the external solution was changed to in a Tris solution.

(h) After the completion of the dialysis, the resultant was centrifuged at 10,000 rpm for about 20 min to separate an aggregation fraction and a supernatant fraction. The supernatant fraction was subjected to SDS-PAGE electrophoresis to confirm that the target protein was made soluble in the supernatant fraction. As a result, an scFv having the No. 7 clone in VL and 7s2 in VH was acquired.

Example 15

Evaluation of scFv for Binding Affinity for Gold by Means of SPR

Figure 17:
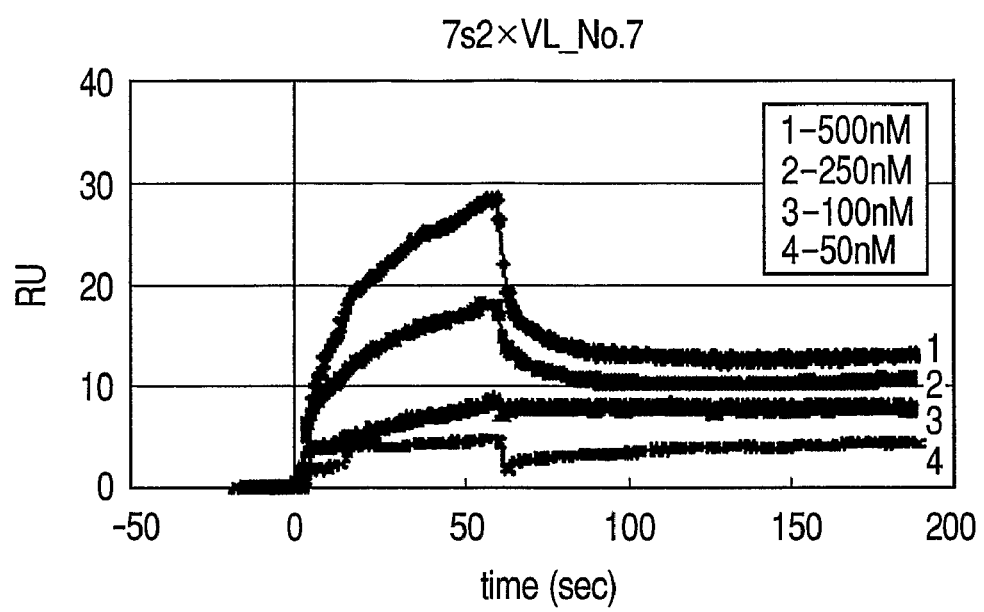
FIG. 17 is a diagram showing an example of the SPR evaluation of scFv obtained by the present invention.

The binding affinity of the scFv protein obtained in Example 14 for gold was measured by means of SPR in the same manner as in Example 8. A binding curve showing binding affinity for gold was obtained (FIG. 17).

Example 16

Confirmation of Au Specificity

Gold specificity of the scFv protein obtained in Example 15 was confirmed. Gold was deposited in a circular pattern having a size of 70 µmφ (having a thickness of 50 nm) on a silicon substrate measuring 3 mm×5 mm as a substrate for confirmation. The surface of the substrate was sequentially immersed in isopropyl alcohol, acetone, and hydrochloric acid for 10 min for each of the solutions for surface washing (the surface was washed with deionized water and dried every time the solution was changed). The substrate was immersed in a solution prepared by adjusting the scFv solution obtained in Example 6 to 1 µM for 1 hour. Subsequently, the substrate was washed while being gently stirred for 10 min in PBST. This operation was repeated 3 times and then a washing solution was discarded. Next, the substrate was immersed in a 100 nM anti-His tag antibody/PBST solution while being gently stirred in the solution for 1 hour. Subsequently, the substrate was washed while being gently stirred for 10 min in PBST. This operation was repeated 3 times and then a washing solution was discarded. Furthermore, the substrate was immersed in a 100 µM rhodopsin-binding anti-IGg antibody/PBST solution while being gently stirred in the solution for 1 hour. Subsequently, the substrate was washed while being gently stirred for 10 min in PBST. This operation was repeated 3 times and then a washing solution was discarded. After that, the substrate was observed with a fluorescence microscope. As a result, fluorescence was observed in a circular portion on which gold was deposited, and no fluorescence was observed in a silicon portion. Therefore, gold specificity of scFv obtained in Example 15 was confirmed.

Comparative Example 1

The gold-deposited silicon substrate was treated by the same operation as that of Example 16 except that the substrate was treated with 1 µM scFv. The substrate was observed with a fluorescence microscope, with the result that no fluorescence was observed in each of a silicon portion and a circular portion on which gold was deposited.

Example 17

Preparation of Silicon Oxide-Philic Peptide-Fused Gold-Binding Protein

A protein having a silicon oxide-philic peptide IPHVHH-KHPHV on the C terminal of the scFv of the above example was prepared according to the following steps.

(1) Preparation of Expression Vector (a) The pUT-scFv (VL#No, 7×7s4) obtained in the above example (Example 14) was templated to perform PCR by using the following primers.

```
SiscFv-B
                                    (SEQ ID No: 119)
5'-NNNNNCCATGGCCCAGGTGCAGTTGGTGGAGT-3'

SiscFv-F
                                    (SEQ ID No: 120)
5'-NNNNNCCGCGGCACGTGGGGGTGCTTGTGGTGCACGTGCATGGGGAT
AACCATTCAGATCCTCTTCT-3'
```

PCR was performed by using a commercially available PCR kit (TAKARA BIO INC, LA-Tag kit) in accordance with a protocol recommended by a supplier.

(b) The resultant PCR product was subjected to 2% agarose electrophoresis. Next, about 400 bp of PCR fragments were obtained from the gel through rough purification by using a gel extraction kit (Promega). The sequence confirmed that the fragments had a target base sequence.

(c) pUT-scFv (7s4) and the PCR fragments obtained in (b) above were cleaved by using NotI/SacII. Next, agarose electrophoresis was performed to purify the target fragments on each of a Vector side and an Insert side.

(d) The purified nucleic acid fragments obtained in (c) above were mixed at a ratio of Vector:Insert=1:5, and then a ligation reaction was performed in the same manner as in Example 1.

Hereinafter, transformation, collection of plasmids, and confirmation of inserts were performed in the same manner as in Example 6.

(3) Expression and Purification of Protein

The expression and purification of a protein were performed in the same manner as in Example 10 by using the plasmids for expression obtained as described above, to thereby obtain a target protein.

Example 18

Acquisition of Gold- and HEL-Binding Protein (1) Adjustment of Gold-Binding VH Code Nucleic Acid Fragment The following primers

```
gVH-B
                                    (SEQ ID No: 121)
5'-NNNNN CCATGG CCGAC CAGG TGCAG TTGGT GGAGT CT-3' gVH-F
                                    (SEQ ID No: 122)
5'-NNNNN GCTAG C GGAGA CGG TGACCAGGGT-3'
``` were used in order to prepare a gold-binding VH (hereinafter, referred to as VHg) for introducing a vector having a restriction enzyme NcoI cleavage site arranged on a 5' terminal side of a gold-binding VH (SEQ ID No: 61) and a restriction enzyme NheI arranged on a 3' terminal side thereof. Then, PCR was performed by using a commercially available PCR kit at a proportion recommended by a supplier to obtain about 350 bp of base pairs. The above VHB-F was used to perform a BigDye-PCR reaction by using a commercially available sequencing reaction kit and a reaction solution composition. A temperature cycle was set to 96° C.×3 min→(94° C.×1 min→50° C.×1 min→68° C.×4 min)×30 cycle→4° C. to confirm that fragments each having a base sequence encoding a target VH were obtained.

(2) Adjustment of Gold-Binding VL Code Nucleic Acid Fragments

Nucleic acid fragments were obtained in the same manner as in (1) except that the following primers

```
gVL-B
                                    (SEQ ID No: 123)
NNNNN GCTAGC GGTGGCGGTGGCTCT GAAATTGTGTT GACGCAGTC
T,
and gVL-F
                                    (SEQ ID No: 124)
NNNNN CCGCG GCACG TTTAA TCTCC AGTCG TGT
``` were used in order to prepare a gold-binding VL (hereinafter, referred to as VLg) (SEQ ID No: 99) for inserting a vector having the restriction enzyme NheI cleavage site and a nucleic acid encoding a linker (GGGGS) arranged on a 5' terminal side of a gold-binding VL (SEQ ID No: 76) and His×6 and a restriction enzyme SacII cleavage site arranged on a 3' terminal side thereof, to thereby confirm that the fragments each having a base sequence of a target VL were obtained.

(3) Adjustment of HEL-Binding VH Code Nucleic Acid Fragments

Nucleic acid fragments were obtained in the same manner as in (1) except that the following primers

```
hVH-B
                                    (SEQ ID No: 126)
5'-NNNNN CCATGG CCGAC GATATCCAGCTGCAGGAGTCGGGCCC-
3',
and hVH-F
                                    (SEQ ID No: 127)
5'NNNNN GCTAG C GGAGA CGG TGACGTCTGT-3
``` were used in order to prepare a HEL-binding VH (hereinafter, referred to as VHh) for introducing a vector having a restriction enzyme NcoI cleavage site arranged on a 5' terminal side of a HEL-binding VH (SEQ ID No: 125) and a restriction enzyme NheI arranged on a 3' terminal side thereof, to thereby confirm that the fragments had a base sequence of the target VL.

(4) Adjustment of HEL-Binding VL Code Nucleic Acid Fragments

Nucleic acid fragments were obtained in the same manner as in (1) except that the following primers

```
hVL-B
                                    (SEQ ID No: 129)
NNNNNGCTAGCGGTGGCGGTGGCTCTGATATCGTCCTGACCCAGAG,
and hVL-F
                                    (SEQ ID No: 130)
NNNNN CCGCG GCCTT GATCT CCAGC TTGGT GC
``` were used in order to prepare an HEL-binding VL (hereinafter, referred to as VLh) for introducing a vector having the restriction enzyme NheI cleavage site and a nucleic acid encoding a linker (GGGGS) arranged on a 5' terminal side of an HEL-binding VL (SEQ ID No: 128) and His×6 and the restriction enzyme SacII cleavage site arranged on a 3' terminal side thereof, to thereby confirm that the fragments had a base sequence of the target VL.

Example 19

Preparation of Expression Vector

The above 4 kinds of nucleic acid fragments were used to constitute 2 expression vectors according to the following configurations.

(1) Preparation of Vector for Expressing VHg-VLh (PGHEL) (FIG. 15)

(i) Insertion of VHg

The plasmid pUT-XX was cleaved with restriction enzyme NcoI/NheI (each manufactured by New England Biolabs) and subjected to spin column 400HR (Amasham Science). Next, VHg was similarly cleaved with the restriction enzyme NcoI/NheI, and the cleaved fragments were purified by using a commercially available gel purification kit (SV Gel and PCR Clean-up system: Promega). The above 2 fragments were mixed with a commercially available T4 ligase kit (Roche) in accordance with a method recommended by a supplier, followed by ligation.

The ligation solution was transformed into 40 μL of JM109 competent cell (Promega) by means of heat shock. The resultant was inoculated on an LB/ampicillin (amp.) plate, and the whole was left standing at 37° C. overnight.

Next, an arbitrary colony on the plate was subcultured in 3 mL of a liquid medium, and the whole was cultured with shaking at 37° C. overnight. After that, plasmids were collected by using a commercially available MiniPreps kit (Plus Minipreps DNA Purification System: Promega).

The base sequence of the resultant plasmid was confirmed by means of the sequence method by using gVH-F. Thus, it was confirmed that the target fragments were inserted.

(ii) Insertion of VLH

The plasmid pUT-VHg obtained in 1) above was cleaved with a restriction enzyme NheI/SacII and subjected to spin column 400HR (Amasham Science). Next, VLh was similarly cleaved with the restriction enzyme NheI/SacII. Next, ligation was performed in the same manner as in (a) above to confirm that a plasmids for expressing VHg-VLH were obtained (the primer for confirmation was hVL-F).

Figure 16:
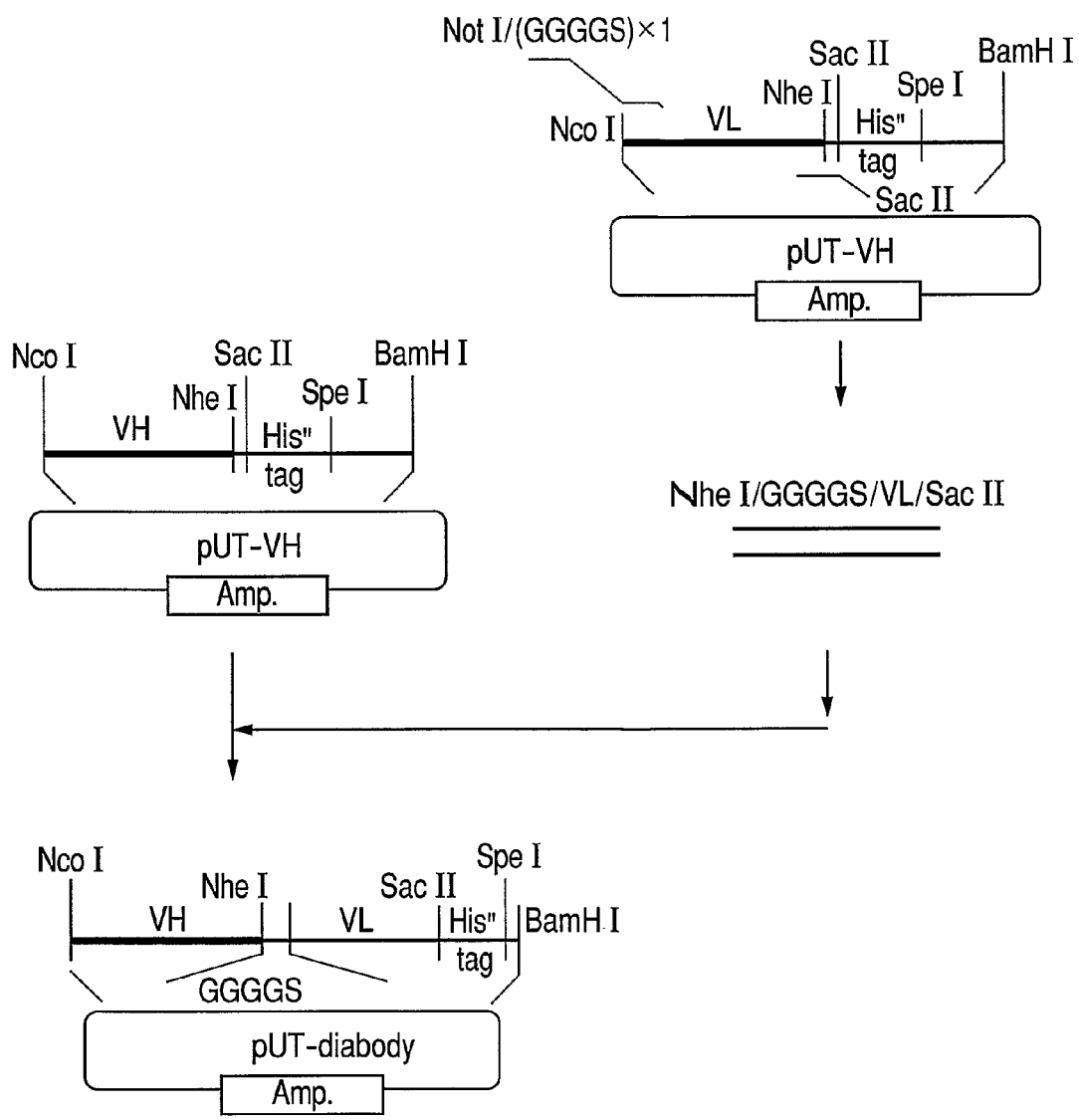
FIG. 16 is a schematic diagram of a vector for illustrating Examples of the present invention.

(2) Preparation of Vector for Expressing VHh-VLg (pH-GOLD) (FIG. 16)

(iii) Insertion of VHh

VHh was inserted into a plasmid pUT in the same manner as in (i) above to confirm that the resultant plasmids were the target plasmids (the primer for confirmation was hVH-F).

(iv) Insertion of VLg

VLg was inserted into the plasmids obtained in (iii) above in the same manner as in (b) above to confirm that the resultant plasmids were the target vector pHGOLD for expressing VHH-VLg in the same manner as in 1) (the primer for confirmation was gVL-F).

Example 20

Expression and Purification of Protein

Expression vectors for expressing the polypeptides of VHg-VLh obtained in (ii) of Example 19 and of VHh-VLg obtained in (iv) of Example 19 were treated in individual systems in a step of expressing and purifying a protein to be described later, and were obtained as polypeptide chains VHg-VLh and VHh-VLg.

1) Transformation

The above expression vectors were used to transform different 40 μL of BL21 (DE3) competent cell solutions. The transformation was performed under such a condition that heat shock was performed in ice→42° C.×90 sec→in ice. 750 μL of LB medium were added to the BL21 solution transformed by heat shock, and the whole was cultured with shaking for 1 hour at 37° C. After that, centrifugation was performed at 6,000 rpm×5 min, and 650 μL of the culture supernatant were discarded. The remaining culture supernatant and a cell fraction as a precipitate were stirred and inoculated on an LB/amp. plate, and the whole was left standing at 37° C. overnight.

2) Preculture

A colony on the plate was selected at random and was cultured with shaking at 28° C. overnight with 3.0 mL of an LB/amp. medium.

3) Main Culture

The preculture solution was subcultured in 750 ML of a 2×YT medium, and the culture was continued at 28° C. When $OD_{600}$ exceeded 0.8, IPTG was added to have a final concentration of 1 mM, and culture was performed at 28° C. overnight.

4) Purification

A target polypeptide chain was purified from an insoluble granule fraction through the following step.

(i) Collection of Insoluble Granule

The culture solution obtained in 3) above was centrifuged at 6,000 rpm×30 min to obtain a precipitate as a bacterial fraction. The resultant was suspended in 15 ml of a Tris solution (20 mM Tris/500 mM NaCl) in ice. The resultant suspension was homogenized with a French press to obtain a bacterial homogenized solution. Next, the bacterial homogenized solution was centrifuged at 12,000 rpm×15 min, and the supernatant was removed to obtain a precipitate as an insoluble granule fraction.

(ii) Solubilization of Insoluble Granule Fraction

The insoluble fraction obtained in (i) above was added with and immersed in 10 mL of a 6 M guanidine hydrochloride/Tris solution overnight. Next, the resultant was centrifuged at 12,000 rpm×10 min to obtain a supernatant as a solubilized solution.

(iii) Metal Chelate Column

A His-Bind (manufactured by Novagen) was used as a metal chelate column carrier. Column adjustment, sample loading, and a washing step were performed at room temperature (20° C.) in accordance with the method recommended by the supplier. Elution of a His tag-fused polypeptide as a target was performed in a 60 mM imidazole/Tris solution. SDS-PAGE (acrylamide 15%) of the eluent confirmed that the eluent had a single band and was purified.

(iv) Dialysis

The eluent was dialyzed by using a 6 M guanidine hydrochloride/Tris solution as an external solution at 4° C. to remove imidazole in the eluent, thereby obtaining the above each polypeptide chain solution.

(v) Refolding

In the same manner as that described above, the polypeptide chain solutions of VHg-VLh and VHh-VLg were separately dialyzed (4° C.) according to the following steps by using dehydrochlorinated guanidine to perform refolding of the protein.

(a) A sample having a concentration of 7.5 μM (volume after dilution of 10 ml) was prepared by using a 6 M guanidine hydrochloride/Tris solution on the basis of the molar absorbance coefficient and ΔO.D. (280 nm-320 nm) of each polypeptide chain. Next, β-mercaptoethanol (reductant) was added to have a final concentration of 375 μM (50-fold protein concentration), followed by reduction at room temperature in a dark room for 4 hours. The sample solution was charged into a dialysis bag (NWCO: 14,000) and provided as a sample for dialysis.

(b) The sample for dialysis was immersed in a 6 M guanidine hydrochloride/Tris solution as an external solution, and was dialyzed for 6 hours while being gently stirred.

(c) The guanidine hydrochloride solution of the external solution was reduced to 3 M and then to 2 M in a stepwise manner. The sample was dialyzed at each concentration of the external solution for 6 hours.

(d) The Tris solution was added with oxidized glutathione (GSSG) to have a final concentration of 375 μM and with L-Arg to have a final concentration of 0.4 M), and then was added with the 2 M dialysis external solution in (c) above to have a guanidine hydrochloride concentration of 1 M. The sample was dialyzed in a solution whose pH had been adjusted to 8.0 (4° C.) with NaOH for 12 hours while being gently stirred.

(e) An L-Arg Tris solution having a guanidine hydrochloride concentration of 0.5 M was prepared by the same operation as that of (d), and dialysis was performed for an additional 12 hours.

(f) Finally, dialysis was performed for 12 hours in a Tris solution.

(g) After the completion of the dialysis, centrifugation was performed at 10,000 rpm for about 20 min to separate an aggregation and a supernatant.

(vi) Purification of Dimerized Fraction

The respective 5 μM polypeptide (VHg-VLh, VHh-VLg) solutions obtained in (v) above were mixed and left standing at 4° C. overnight. Next, a fraction corresponding to 60 kDa (about 18 minutes from the injection) dimerized in a Sephadex 75 column (column: buffer 20 mM Tris, 500 mM NaCl, flow rate: 1 ml/min) was obtained. This was provided as a sample for SPR measurement.

Example 21

Evaluation of Binding Affinity for Gold Through SPR Measurement

The binding affinity of the dimerized protein fraction obtained in Example 20 for gold was measured by means of SPR. A BIAcore 2000 (manufactured by BIAcore) was used as an SPR measuring device. A gold-deposited glass substrate SIA-kit Au of the same company was used as a gold substrate (to which the fraction was to be bound). Measurement was performed under the following conditions. 500 nM (calculated from the absorbance as described above) of the dimerized protein fraction obtained in Example 15 were used as a sample.

Figure 18:
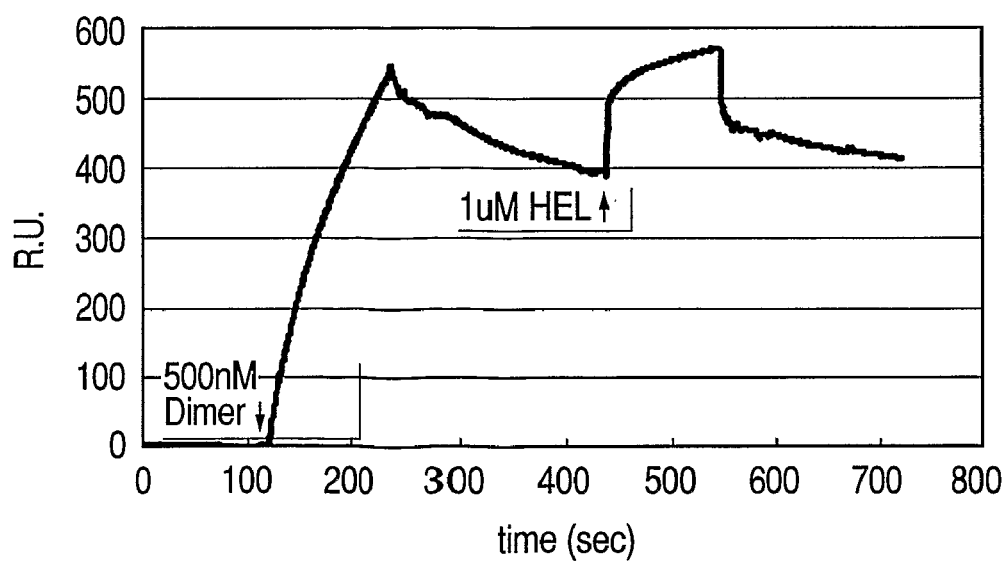
FIG. 18 is a SPR chart in Example 21.

Running buffer: 0.1% Tween 20/Tris solution:TBST
Temperature: 25° C.
Flow rate: 20 μL/min
Sample injection amount: 40 μL A binding curve showing the binding affinity for gold was obtained (FIG. 18).

Example 22

Evaluation of Binding Affinity to HEL Through SPR Measurement

Subsequent to the sample subjected to SPR evaluation of binding affinity for gold in Example 21, a 1 μM HEL solution was continuously injected to measure binding affinity of the gold-bound dimerized protein fraction to HEL by means of SPR. A binding curve showing the binding affinity to HEL was obtained (FIG. 18).

Example 23

Confirmation of Au Specificity

The gold substrate of an SPR chip obtained in Example 22 to which the gold-binding protein and HEI were bound was used to subsequently perform the following experiment. The gold substrate described above was injected with a 1 μM anti-HEL antibody/PBST solution. After that, the substrate was washed with PBST. Furthermore, the substrate was injected with a 1 μM rhodopsin-binding anti-IGg antibody/PBST solution. After that, the substrate was washed with PBST. The SPR chip described above was removed from an SPR device, and the substrate was observed with a fluorescence microscope. As a result, fluorescence was observed on a flow path of SPR on the gold substrate.

Comparative Example 2

The same operation as that of Example 23 was performed by using an unused gold-deposited substrate. As a result, no fluorescence was observed on the gold substrate.

Example 24

A rewound polypeptide chain VHg-VLh obtained through the steps as those of (i) to (v) in Example 20 was prepared, and a 5 μM VHg-VLh/Tris solution was obtained.

Example 25

The VHg-VLh/Tris solution obtained in Example 24 was diluted with a Tris solution to 500 nM, and the binding affinity to the gold substrate was evaluated in the same manner as in Example 20. Furthermore, a 1 μM HEL solution was continuously injected to measure the binding affinity of the gold-bound dimerized protein fraction to HEL. A binding curve showing binding affinity for gold and HEL was obtained.

Example 26

In Example 25, a 0.5 μM anti-HEL antibody VL/Tris solution was allowed to coexist, and the whole was left standing overnight to prepare a sample.

Example 27

The sample prepared in Example 26 was evaluated for binding affinity to the gold substrate by means of SPR in the same manner as in Example 15. Furthermore, in the same manner as in Example 16, a 1 μM HEL was continuously injected to measure binding affinity to the sample by means of SPR. A binding curve showing the binding affinity was obtained.

Example 28

Preparation of HEL Detecting Immunochromatography Device

An immunochromatography device for detecting HEL was prepared as an example of detecting method of the present invention.

1) Preparation of Porous Carrier for Immunochromatography on Which Anti-HEL Antibody is Immobilized A nitrocellulose sheet (BAS-85, manufactured by Schleicher & Schuell) was cut into a piece measuring 5 mm×30 mm. A 0.5 mg/mL of an anti-HEL antibody solution (manufactured by Nippon Biotest Labo) was linearly applied at a position 1.0 mm away from the end of the piece in an amount off 0.5 mg/mL, to thereby prepare a detection site. The sheet was left standing at room temperature for 2 hours to dry the liquid, whereby the antibody was fixed as a sheet. The sheet was shaken for 2 hours in a 1% skim milk (manufactured by Difco)/PBST solution and blocked. After that, the sheet was left standing at room temperature to prepare a carrier for immunochromatography.

2) Preparation of Gold-Labeled anti-HEL Antibody Fragment and Hold-Back Carrier (i) Preparation of Gold-Labeled Anti-HEL Antibody Fragment The fragment of this title was prepared according to the following step by using the gold/HEL bispecific antibody fragments prepared in Example 20.

A dispersion of gold fine particles (particle size 50 nm, manufactured by Tanaka Kikinzoku) was added and sufficiently mixed with the gold/HEL bispecific antibody fragments prepared in Example 20, and a reaction was performed at room temperature for 3 hours. The resultant was centrifuged at 12,000 rpm for 5 min in order to remove unreacted gold/HEL bispecific antibody fragments, and then the supernatant was removed to obtain a precipitate. The resultant precipitate was suspended in 1.0 mL of PBST. Furthermore, centrifugation was performed under the above conditions. The resultant precipitate was suspended in 1.0 mL of 1% BSA/PBST.

(ii) Preparation of Gold-Labeled Anti-HEL Antibody Fragment-Holding Carrier

A Bemliese non-woven fabric (manufactured by Asahi Kasei Corporation) measuring 5 mm×5 mm was impregnated with 5 μL of the gold-labeled anti-HEL antibody fragment solution and 5 μL of a 10% aqueous solution of various bases, and was air-dried to prepare a gold-labeled anti-HEL antibody fragment-holding carrier.

3) Preparation of Test Piece-Type Immunochromatography Device

The gold-labeled anti-HEL antibody fragment-holding carrier prepared in 2) (ii) above was allowed to overlap the carrier for immunochromatography prepared in 1) above up to a position 2.5 mm away from one end of the carrier for immunochromatography. Furthermore, a carrier for soaking a liquid sample (filter paper No. 526, manufactured by Advantec Toyo) was allowed to overlap the antibody fragment-holding carrier. In addition, a carrier for an excess sample-soaking portion (filter paper No. 526) was allowed to overlap the carrier for immunochromatography up to a position 5 mm away from the other end of the carrier for immunochromatography. Finally, a tape was attached to the rear side to stabilize the entirety, whereby a test piece-type immunochromatography device was prepared. A test using a standard HEL solution confirmed that an anti-HEL antibody-immobilized portion presented a red color.

Example 29

Preparation of Electrical Measuring Instrument

An example of a method of detecting a protein using a gold electrode is shown.

1) 2 gold electrodes were placed on a glass substrate. The distance between the electrodes was set to 20 μm. 20 μL of a 0.1% poly-L-lysin (Sigma-Aldrich) aqueous solution were dropped onto a space between the electrodes, and the whole was left standing for 3 hours.

Next, the substrate was washed with water. After that, the substrate was washed with ethanol 3 times and dried.

2) Next, an anti-HEL polyclonal antibody (ROCKLAND) was immobilized on the glass substrate obtained in (a) above on the basis of Proteomics, 3, pp 254 (2003).

3) The PBST solution of the gold/HEL bispecific antibody fragment prepared in Example 20 and 20-nm gold nanoparticles (manufactured by Tanaka Kikinzoku) were allowed to react with each other (PBST solution for comparison).

4) The anti-HEL antibody-immobilized substrate obtained in 1) was added with a 1 μM HEL/PBS solution.

5) Next, the product obtained in 3) was added with the gold-binding protein solution obtained in 2).

6) The substrate obtained in 4) was washed with a PBS solution 3 times. After that, the substrate was immersed in a silver enhancer solution (Sigma-Chemical) for 5 min, followed by washing with water. A reduction in electrical resistance between the electrodes as compared to that of only PBST as a comparative sample was confirmed.

Example 30

Preparation of Vector for Expressing VHg-VHh Protein in Yeast (1) Preparation of NheI-VHh-SacII Fragments VHh fragments having NheI/SacII at its terminals were prepared by PCR by using a pHGold prepared in Example 19 as a template.

The following primers were used.

```
NheI-VHh_f
                                    (SEQ ID No: 131)
NNNNNGCTAGCCAGGTGCAGTTGGTGGAGTCT

VHh-sacII_r
                                    (SEQ ID No: 132)
NNNNNCCCGCGGATGAGGAGACGGTGACCAGGGTT
```

The above primers were used to perform PCR of pfu-turbo in accordance with a method recommended by a supplier. The resultant PCR reaction solution was subjected to agarose gel (2%) electrophoresis to confirm that about 350 bp of fragments were obtained.

(2) Preparation of VHg-VHh DNA Fragments

The VHh fragments obtained in (1) above were introduced into a VLh portion of pGHEL prepared in Example 19.

The PCR fragments and pGHEL obtained in (1) were cleaved with NheI/SacII (each manufactured by TAKARA BIO INC.). A restriction enzyme reaction was performed in accordance with a method recommended by one skilled in the art. The resultant reaction solutions were subjected to agarose electrophoresis, followed by gel purification (PCR fragment: agarose 2%, pGHEL: agarose 1%). The above-described gel purification kit was used for the gel purification.

It was confirmed that the PCR fragments obtained after the restriction enzyme reaction as described above had about 350 bp of PCR fragments and 3,000 bp of plasmid fragments, and a novel plasmid were obtained hereinafter in the same manner as in Example 19.

The base sequence of the resultant plasmids was determined by means of a sequencer to confirm that the base sequence was a target base sequence (the plasmid was defined as pHgHh).

(3) Insertion of Yeast Expression Plasmids

PCR was performed in accordance with the same method that recommended by a supplier.

pPCIZαA (Invitrogen) was used as an yeast (*Pichia pastris*) expression plasmid. Target gene was introduced by using EcoRI and SacII at multicloning sites of the plasmid.

The gene to be introduced was prepared by PCR by using pHgHh obtained in (2) as a template. As a primer,

```
7s4-fW-EcoRIs
                                    (SEQ ID No: 133)
AAGCTGAATTCCAGGTGCAGTTGGTGGAGTCT

HELVH-SacII-r
                                    (SEQ ID No: 134)
NNNNNCCGCGGAGACGGTGACGAGGGT
```

The resultant PCR fragments and the pPCIZαA were sequentially cleaved with EcoRI and SacII, and each target fragment was obtained in the same manner as that described above through gel purification.

Ligation was performed in accordance with the method described above. A ligation reaction solution was transformed in the same manner as that described above and inoculated on an agar plate. The agar plate in this case was such that tryptophan 10 g/yeast extract 5 g/NaCl 5 g/agar 15 g/L were added with Zeocin to have a concentration of 25 μg/L. A colony selected by this condition was cultured in a liquid medium (tryptophan 10 g/yeast extract 5 g/NaCl 15 g, Zeocin 25 μg/L) at 37° C. overnight. After the collection of plasmids, a sequence was confirmed by using a sequencer to obtain a plasmid expressing VHg-VHh:VH_gold-linker (GGGGS)-VH_HEL as an object of this example (provided as pPCIZ-αHH).

Example 31

Expression/Purification of VHg-VHh Protein

The expression of VHg-VHh was performed by using an Easy Select *Pichia* Expression Kit Ver. G (Invitrogen). The preparation of a transformant and the preparation and purification of the protein (metal chelate column) were each performed in accordance with a method recommended by one skilled in the art. 5 mL of a 1 M imidazole eluted fraction obtained by a metal chelate column were dialyzed by using a Tris buffer (20 mM Tris/200 mM NaCl, 1 mM EGTA: pH 7.9) as an external solution at 4° C. The external solution was changed every 6 hours and a total of 3 times.

Figure 19:
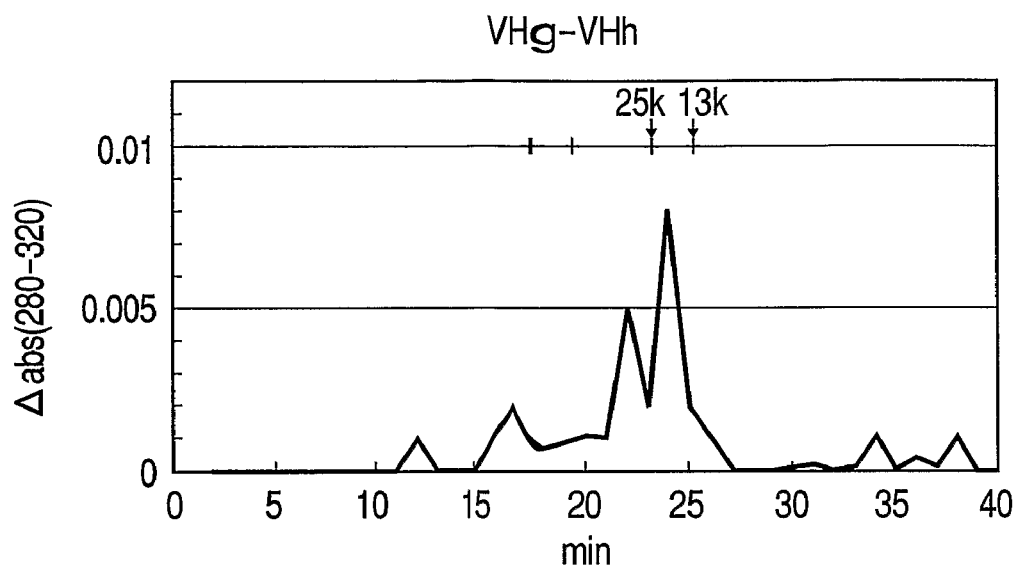
FIG. 19 is a GPC chart in Example 31.

Subsequently, by using a Sephadex 75 (Amasham Bioscience), purification based on gel filtration was performed at 4° C. (buffer condition: 50 mM Tris-HCl, 200 mM NaCl, 1 mM EDTA, pH 8.0, flow rate: 0.7 mL/min). After the resultant fraction had been concentrated, the same western Blotting as that described above was performed by using SDS-PAGE (acrylamide 17.5%) and HRP-fused anti-His antibody. Thus, a fraction of the target protein was specified and purified into a single band. A peak suggesting that the fraction was a monomer protein of about 25 kDa was fractionated, followed by the following evaluation (FIG. 19).

Example 32

Evaluation of Binding Affinity for Gold by Means of SPR

Figure 20:
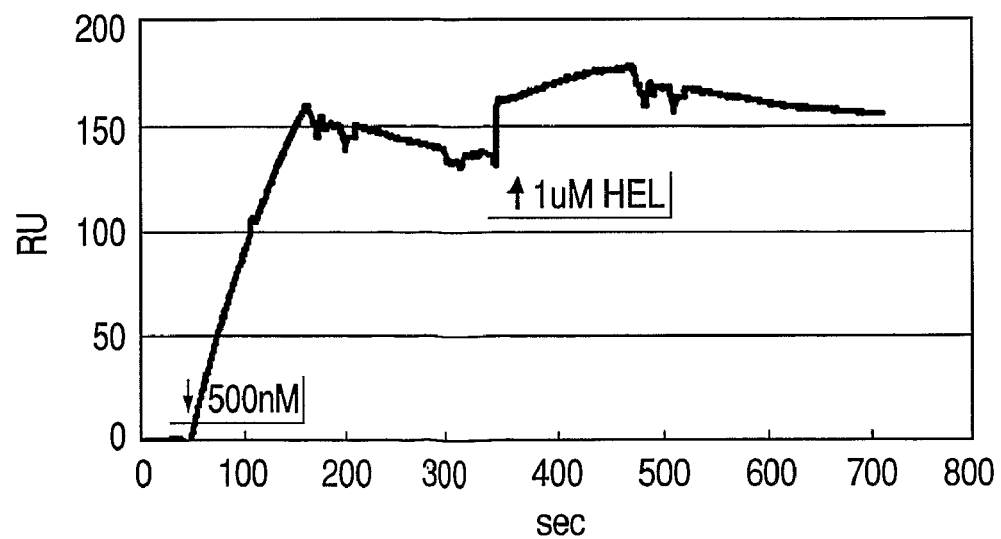
FIG. 20 is a SPR chart in Example 32.

The binding affinity of the protein fraction obtained in Example 31 for gold was measured by means of SPR. A BIAcore 2000 (manufactured by BIAcore) was used as an SPR measuring device. A gold-deposited glass substrate SIA-kit Au of the same company was used as a gold substrate to which the fraction was to be bound. Measurement was performed under the following conditions. 500 nM (calculated from the absorbance as described above) of the protein fraction obtained in Example 20 were used as a sample. The conditions of this example were the same as those Example 21. A binding curve showing binding affinity for gold was obtained (FIG. 20).

Example 33

Preparation of VHg-VHh Protein Variant −1

A QC kit (manufactured by STRATAGENE) was used with the plasmid pPCIZ-α7s4 obtained in Example 30 as a template to obtain a VHg variant (SEQ ID No: 135 or 136) to serve as V37L, G44E, and L45R of the gold-binding VH of Example 30. The following primers were used to obtain a target plasmid through 3 times of operation. Mutation was sequentially inserted for each operation into one site.

PCR primer for inserting mutation to a first site

```
V37F-f
                                         (SEQ ID No: 137)
TTACTGGATCAACTGGTTCCGCCAGATGCCCGG

V37F-r
                                         (SEQ ID No: 138)
CCGGGCATCTGGCGGAACCAGTTGATCCAGTAA
```

PCR primer for introducing mutation to a second site

```
G44E-f
                                         (SEQ ID No: 139)
CAGATGCCCGGCAAAGAACTGGAATGGATGGGG

G44E-r
                                         (SEQ ID No: 140)
CCCCATCCATTCCAGTTCTTTGCCGGGCATCTG
```

PCR primer for introducing mutation to a third site

```
L45F-f
                                         (SEQ ID No: 141)
GCCCGGCAAAGAAAGGGAATGGATGGGGATG

L45F-r
                                         (SEQ ID No: 142)
CATCCCCATCCATTCCCTTTCTTTGCCGGGC
```

Insertion of mutation was confirmed by a sequence. The procedure from the transformation to the expression of a protein was the same as that of Example 31. The following evaluation was performed by using a peak of a monomer protein of about 25 kDa.

Example 34

Evaluation of Binding Affinity for Gold by Means of SPR

Figure 21:
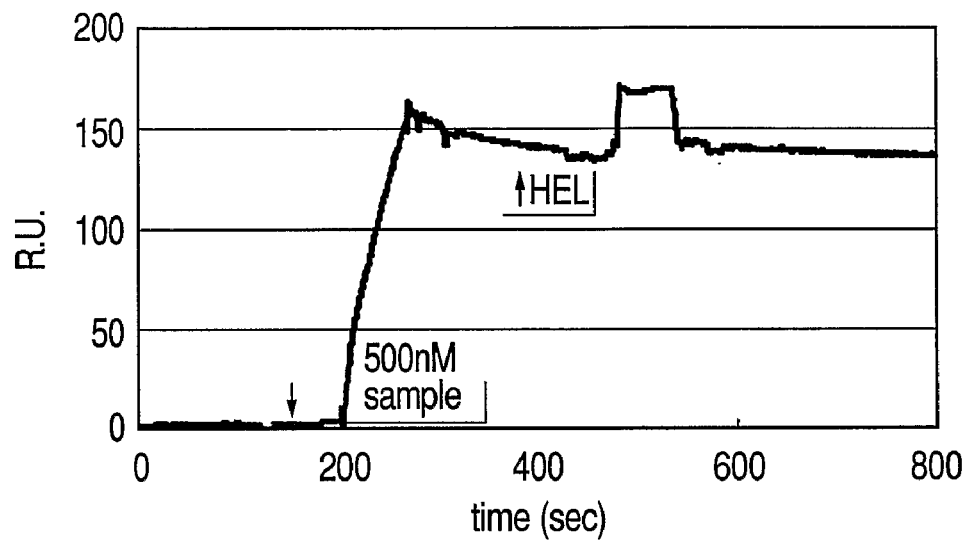
FIG. 21 is a SPR chart in Example 34.

The binding affinity of the protein fraction obtained in Example 33 for gold was measured by means of SPR. A BIAcore 2000 (manufactured by BIAcore) was used as an SPR measuring device. A gold-deposited glass substrate SIA-kit Au of the same company was used as a gold substrate to which the fraction was to be bound. Measurement was performed under the following conditions. 500 nM (calculated from the absorbance as described above) of the protein fraction obtained in Example 33 were used as a sample. The conditions of this example were the same as those Example 21. A binding curve showing binding affinity for gold was obtained (FIG. 21).

Example 35

Preparation of VHg-HEL scFv Protein Variant

Substitution was performed in such a manner that a protein fused with HEL-binding scFv (SEQ ID No: 143 or 144) instead of HEL-binding VH of Example 31 was obtained. DNA fragments encoding HEL-binding scFv was obtained by PCR with a plasmid to which an HEL-binding scFv coding gene was introduced, show in Journal of Biological chemistry, 2003, 279, pp 8979, as a template. PCR was performed in accordance with the same method as that recommended by one skilled in the art, and the following primers were used.

```
scFv-f
                                         (SEQ ID No: 145)
NNNNCCATGCCCGATATCGTCCTGACCCAG scFv-r
                                         (SEQ ID No: 146)
AGCTACCGCGGAGACGGTGACGAGGGT
```

The procedure subsequent to a restriction enzyme reaction was the same as that of Example 30, whereby a target plasmid was obtained.

It was confirmed by using a sequence that the resultant plasmid had a target gene sequence. The procedure from the transformation to the expression of a protein was the same as that of Example 31. Thus, a monomer protein of about 39 kDa was obtained.

Example 36

Evaluation of Double-Binding Affinity for Gold and HEL by Means of SPR

Figure 22:
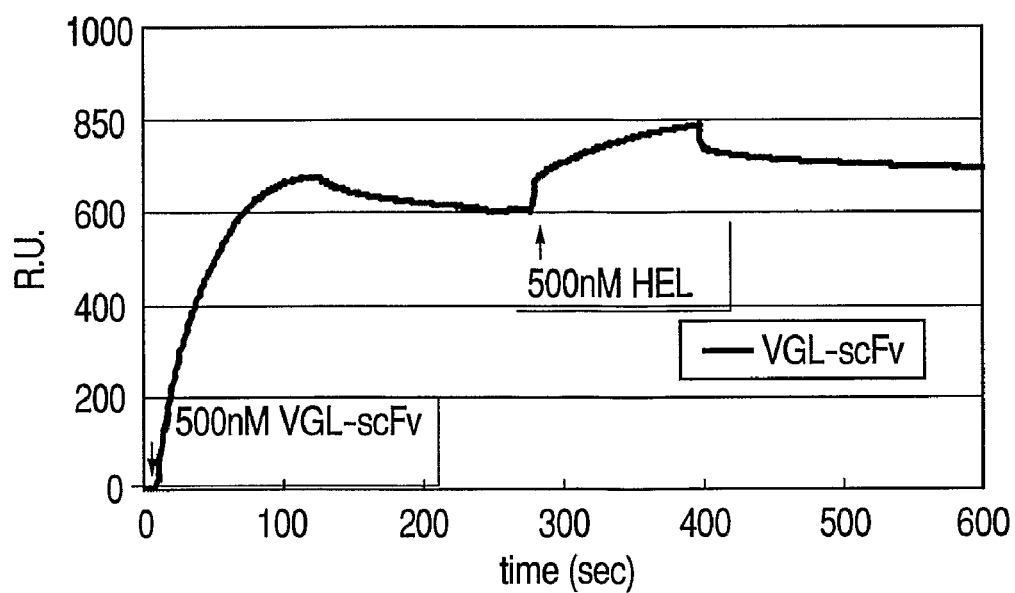
FIG. 22 is a SPR chart in Example 36.

The binding affinity of the protein fraction obtained in Example 35 for gold was measured by means of SPR. A BIAcore 2000 (manufactured by BIAcore) was used as an SPR measuring device. A gold-deposited glass substrate SIA-kit Au of the same company was used as a gold substrate to which the fraction was to be bound. Measurement was performed under the following conditions. 500 nM (calculated from the absorbance as described above) of the protein fraction obtained in Example 31 were used as a sample. The conditions of this example were the same as those Example 21 and 22. A binding curve showing binding affinity for gold was obtained (FIG. 22).

Example 37

Preparation of Plasmid for Expressing VHg Variant-VLh

A DNA sequence represented by SEQ ID No: 147 and 148 were introduced into a gold-binding VH code sequence of the plasmid for expression (pGHEL) obtained in Example 19. An insertion method involved the use of the Quick Change kit described above (Stratagene) with the pGHEL as a template above. It was confirmed that the resultant plasmid had a target sequence. Next, the resultant plasmid was used to perform the expression and purification of a protein and the dimerization with VHh-VLg in the same manner as in Example 20.

Figure 23:
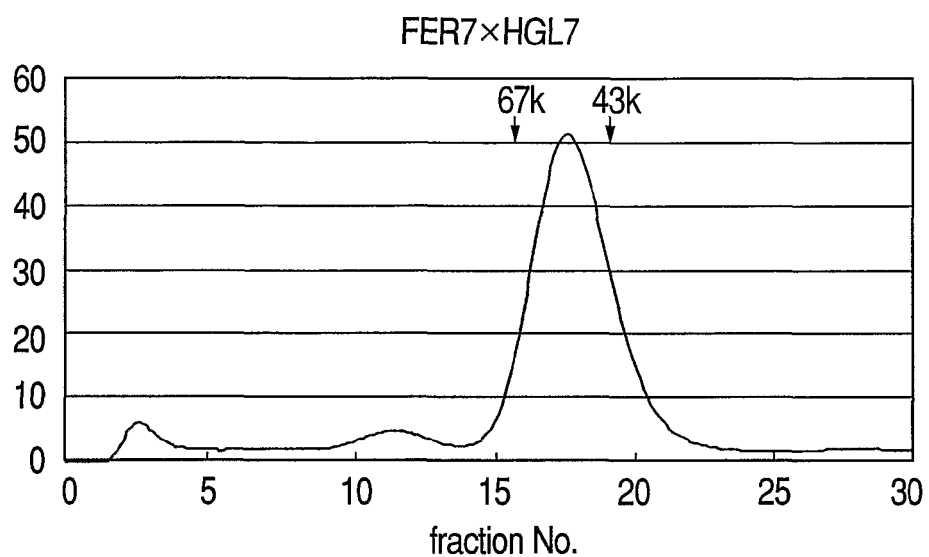
FIG. 23 is a GPC chart in Example 37.

A protein fraction having a molecular weight of about 50 kDa was fractionated by using a Sephadex G75 (FIG. 23).

```
A14P-f
                                        (SEQ ID No: 147)
GAGCAGAGGTGAAAAAGCCAGGGGAGTCTCTGAAG

A14P-r
                                        (SEQ ID No: 148)
CTTCAGAGACTCCCCTGGCTTTTTCACCTCTGCTC
```

Example 38

Evaluation of Double-Binding Affinity for Gold and HEL by Means of SPR

Figure 24:
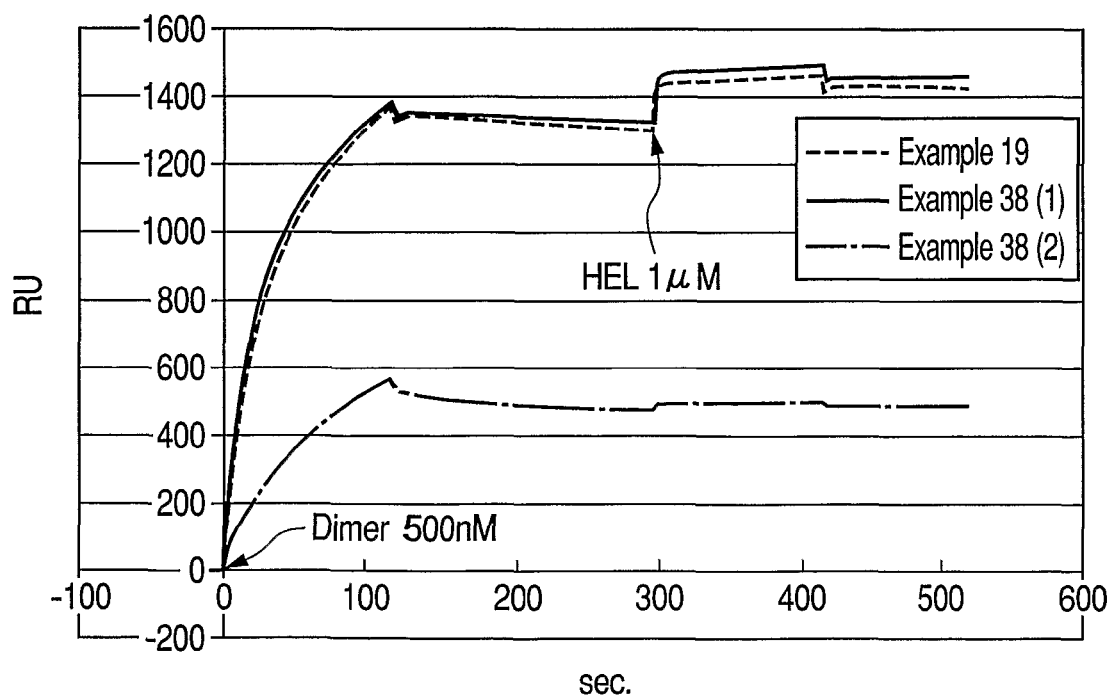
FIG. 24 is a SPR chart in Example 38.

The binding affinity of the protein fraction obtained in Example 37 for gold was measured by means of SPR. A BIAcore 2000 (manufactured by BIAcore) was used as an SPR measuring device. A gold-deposited glass substrate SIA-kit Au of the same company was used as a gold substrate to which the fraction was to be bound. Measurement was performed under the following conditions. 500 nM (calculated from the absorbance as described above) of the protein fraction obtained in Example 37 were used as a sample. The conditions of this example were the same as those Example 21. A binding curve showing binding affinity for gold was obtained (FIG. 24).

Example 39

Preparation of Plasmid Expressing VHg-VLg Tetramer pPCIZ-αVHg$^2$ was prepared in the same manner as in Example 30 except that VHh of Example 30 was changed to VHg coding gene fragments.

pRA2-7s4 obtained in Example 10 was used as a template for preparing a DNA fragments encoding the VHg to be used in the above operation, and the following primers

```
VHg-f
                                        (SEQ ID No: 149)
NNNNNGCTAGC GGCGGGGCGGTAGC CAGGTGCAGTTGGTGGAGTCT

VHg-r
                                        (SEQ ID No: 150)
NNNNNCCGCGGATGAGGAGACGGTGACCAGGGTT
``` were used as primers

It was confirmed by a sequence that a target plasmid was obtained.

Example 40

Preparation of VHg-VLg Protein

Figure 25:
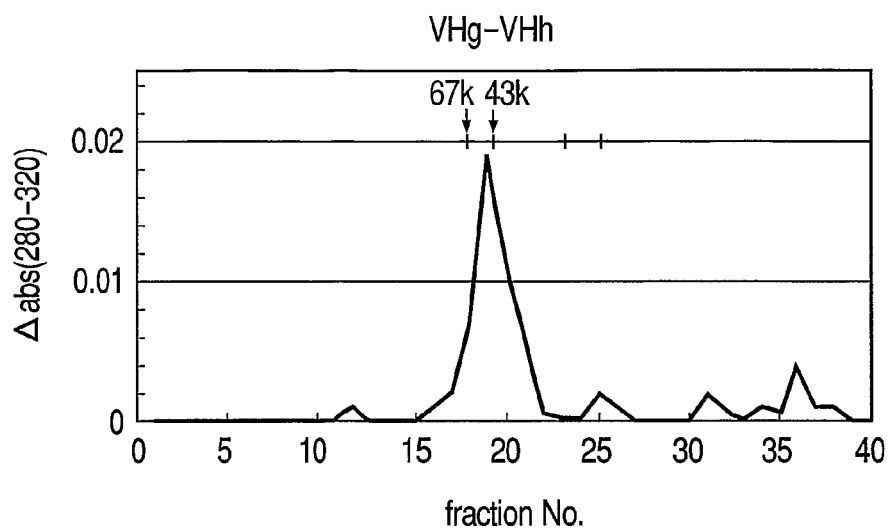
FIG. 25 is a GPC chart in Example 40.

A target protein was purified by the same procedure as that of Example 31. A protein composed of a dimer of VHg-VHg having a molecular weight of about 25 kDa was purified (FIG. 25).

Example 41

Preparation of Plasmid Expressing VHg-VLg Tetramer pPCIZ-αVHg$^4$ was prepared in the same manner as in Example 30 except that the linker GGGGS for linking VHg-VHg of Example 39 was changed to GS.

pRA2-7s4 obtained in Example 10 was used as a template for preparing a DNA fragment encoding the VHg to be used in the above operation, and the following primers

```
VHg4-f
                                        (SEQ ID No: 151)
NNNNNGCTAGC GGCAGC CAGGTGCAGTTGGTGGAGTCT

VHg4-r
                                        (SEQ ID No: 152)
NNNNNCCGCGGATGAGGAGACGGTGACCAGGGTT
``` were used as primers.

It was confirmed by a sequence that a target plasmid was obtained.

Example 42

Gold Fine Particles Agglutination Reaction

Figure 26:
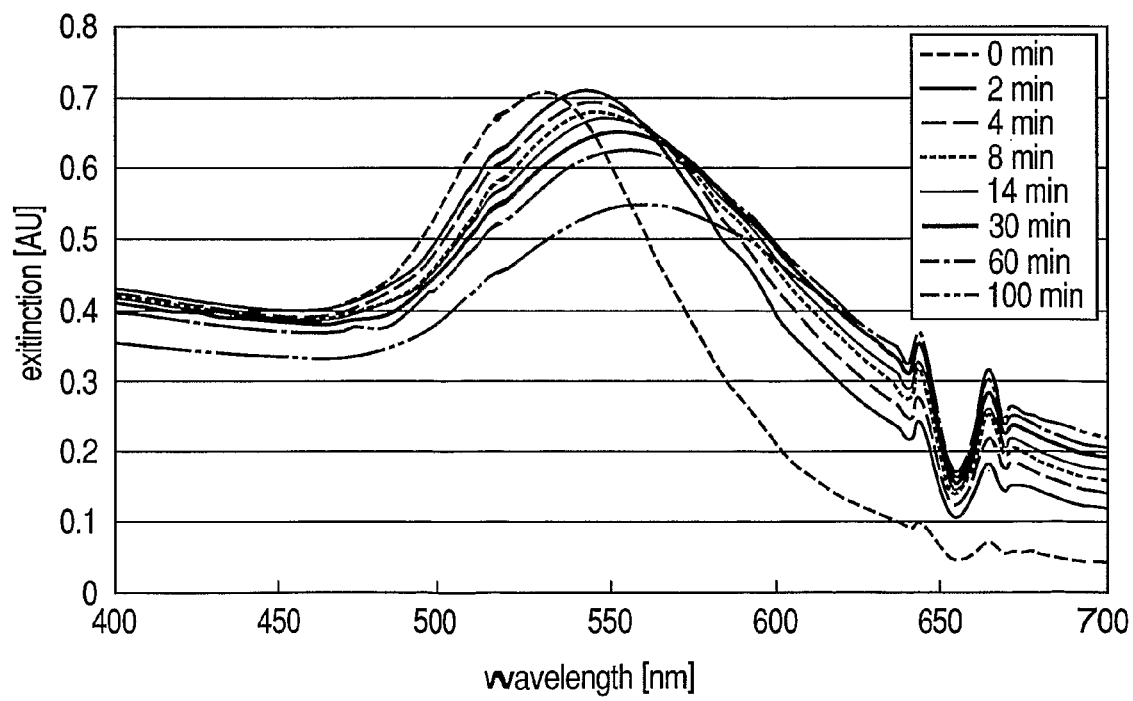
FIG. 26 is an absorption curve of a solution containing a gold fine particle in Example 42.

In a 500 μM/PBST solution of each of the proteins obtained in Examples 40 and 44, gold fine particles (20 nmφ: manufactured by Tanaka Kikinzoku) were incubated at room temperature. The agglutination of the gold fine particles was observed regardless of which protein was used. In addition, a spectrum (λmax) of a mixture of gold fine particles/a protein was observed to change with time, and a half band width was observed to expand. A result suggesting that the distance between gold fine particles was shortened was obtained (FIG. 26).

Comparative Example 3

Figure 27:
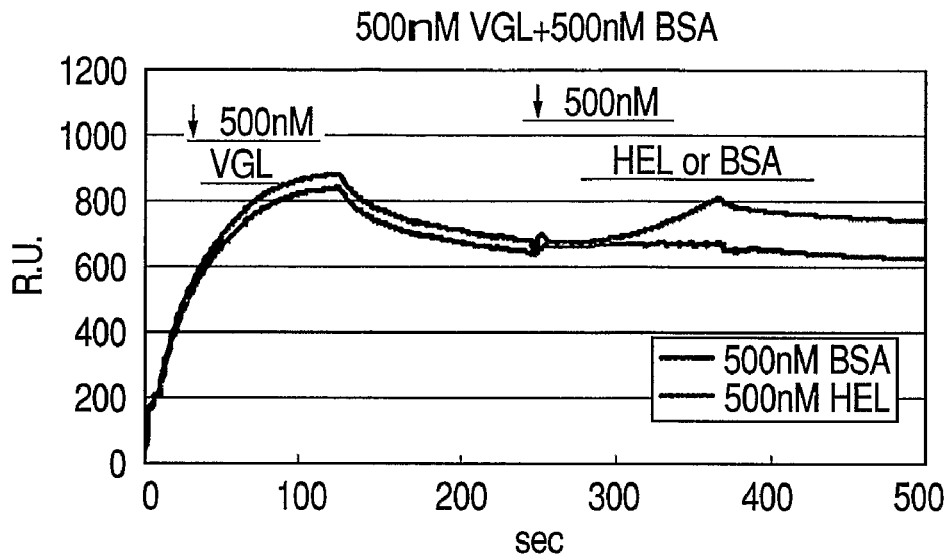
FIG. 27 is a SPR chart in Comparative Example 3.

The same operation as example 36 was performed by using 500 nM BSA instead of 500 nM HEL. Binding to BSA was not confirmed. It was shown that the protein for gold obtained in example 35 binds to HEL in a specific manner (FIG. 27).

Comparative Example 4

Binding ability of proteins immobilized directly on gold substrate was evaluated by anti-HEL antibody (manufactured by Rockland) using SPR measurement.

(1) Preparing 10 μM HEL in PBS (2) Injecting 100 μl of the solution obtained (1) at 1 μl/min. The signal of absorbed antibody was 1907 R. U.

(3) 1% casein in PBS was injected in the same manner as (2)

(4) Further, 40 μl of 1% casein in PBS was injected at 20 μl/ml and confirm that the gold substrate was blocked.

Figure 28:
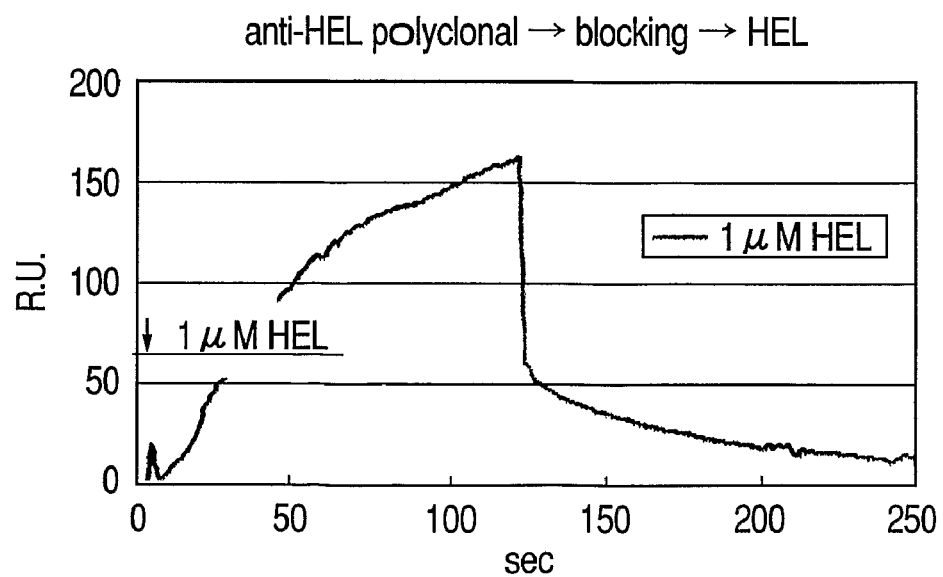
FIG. 28 is a SPR chart in comparative Example 4.

(5) Consequently, injecting 40 μl of 1 μM at 20 μl/min and obtaining the result shown in FIG. 28.

As the result, the signal of bond HEL molecule was 11 R. U., while that of antibody immobilized on gold substrate was 1907 R. U. Considering of configuration at immobilization and assuming that a single antibody molecule captured one antigen on a substrate, the rate of antibodies captured target substances was calculated to be about 6%.

In the other hand, it was shown that 20 to 40% of proteins in the present invention captured antigens by examples indicated above. Moreover, any special reagents or process was not required for the immobilization of proteins that are capturing molecules of sensors in the examples indicated above, implying that the immobilization method of the present invention is superior to conventional physical absorption.

INDUSTRIAL APPLICABILITY

The present invention provides: a gold-binding protein having one or more binding sites to gold and a binding site to a specific substance; a structure including a gold substrate on which the gold-binding protein is immobilized; and a detection device using the same.

In a detection device composed of a structure on which a gold-binding protein obtained by applying the present invention is immobilized, the protein is immobilized at a binding site specifically recognizing gold serving as a substrate. Therefore, the binding site of the protein recognizing a specific substance (target substance) is not immobilized on the substrate, and the protein is oriented while a distance from the substrate is ensured. As a result, a target substance binding site minimizes the influence of the substrate on its binding capacity, whereby the protein is immobilized on the substrate with efficiency and high orientation.

That is, it is suggested that the present invention can be utilized for improving the performance of products applying the functions of various biological substances which immobilize organic substances such as biological substances on substrate surfaces to utilize various physiological functions of the organic substances, the products being typified by a biosensor and a bioreactor.

Meanwhile, the present invention provides a connecting member for labeling a target substance, including: one or more sites binding to the target substance; and one or more sites binding to the labeled substance, characterized in that the respective binding sites bind to a substance to be bound independently from each other. The application of the present invention enables a target protein to be labeled without the use of a conventional chemical crosslinking method. As a result, influences on the binding affinities of various proteins to target substances, the influences being of concern at the time of labeling, can be minimized, and production efficiency can be increased. That is, the present invention can be utilized for improving the performance of products applying the functions of various biological substances, such as biosensor, which immobilize connecting members on substrate surface, and utilize various physiological functions of the connecting members.

This application claims priority from Japanese Patent Application No. 2004-108388 filed Mar. 31, 2004, which is hereby incorporated by reference herein.

The invention claimed is:

1. An isolated protein comprising at least an antibody heavy chain variable region (VH) or an antibody light chain variable region (VL),
wherein the antibody heavy chain variable region (VH) or the antibody light chain variable region (VL) comprises a region specifically binding to gold at $K_D=3.0\times10^{-7}$ M or less.

2. The protein of claim 1, wherein the protein comprises an antibody heavy chain variable region (VH) and an antibody light chain variable region (VL), and wherein each of the antibody heavy chain variable region (VH) and the antibody light chain variable region (VL) comprises a region specifically binding to gold at $K_D=3.0\times10^{-7}$ M or less.

3. A connecting member for labeling a target substance with a labeling agent, comprising:
one or more sites binding to the target substance and one or more sites binding to the labeling agent, wherein:
the site binding to the target substance and the site binding to the labeling agent each independently bind to a substance to be bound; and
at least one of the site binding to the labeling agent and the site binding the target substance contains an antibody heavy chain variable region (VH) and/or an antibody light chain variable region (VL) comprising a region that specifically binds to gold at $KD=3.0\times10^{-7}$ M or less.

4. A connecting member according to claim 3, wherein the labeling agent or the target substance has at least one or more of a metal, a metal oxide, and a semiconductor compound each containing gold.

5. A method of detecting a target substance, in which the target substance is bound and labeled with a labeling agent to detect the target substance bound with the labeling agent, comprising the step of:
binding the labeling agent to the target substance via a connecting member
comprising one or more sites binding to the target substance and one or more sites binding to the labeling agent, wherein:
the site binding to the target substance and the site binding to the labeling agent each independently bind to a substance to be bound; and
at least one of the site binding to the labeling agent and the site binding the target substance contains an antibody heavy chain variable region (VH) and/or an antibody light chain variable region (VL) comprising a region that specifically binds to gold at $KD=3.0\times10^{-7}$ M or less.

* * * * *